US011739372B2

(12) United States Patent
Frisen et al.

(10) Patent No.: US 11,739,372 B2
(45) Date of Patent: *Aug. 29, 2023

(54) SPATIALLY DISTINGUISHED, MULTIPLEX NUCLEIC ACID ANALYSIS OF BIOLOGICAL SPECIMENS

(71) Applicants: Spatial Transcriptomics AB, Stockholm (SE); Illumina, Inc., San Diego, CA (US)

(72) Inventors: Jonas Frisen, Stockholm (SE); Patrik Stahl, Stockholm (SE); Joakim Lundeberg, Lidingö (SE); Gordon M. Cann, San Diego, CA (US); Leila Bazargan, San Diego, CA (US); Alex Aravanis, San Diego, CA (US)

(73) Assignees: Spatial Transcriptomics AB, Stockholm (SE); Illumina, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/166,853

(22) Filed: Feb. 9, 2023

(65) Prior Publication Data

US 2023/0183785 A1    Jun. 15, 2023

Related U.S. Application Data

(60) Continuation of application No. 17/834,474, filed on Jun. 7, 2022, now Pat. No. 11,613,773, which is a continuation of application No. 17/693,116, filed on Mar. 11, 2022, now Pat. No. 11,390,912, which is a continuation of application No. 17/479,718, filed on Sep. 20, 2021, now Pat. No. 11,299,774, which is a continuation of application No. 17/237,670, filed on Apr. 22, 2021, now Pat. No. 11,162,132, which is a continuation of application No. 17/011,923, filed on Sep. 3, 2020, which is a division of application No. 15/565,637, filed as application No. PCT/EP2016/057355 on Apr. 10, 2015, now Pat. No. 10,774,374.

(60) Provisional application No. 62/145,874, filed on Apr. 10, 2015.

(51) Int. Cl.
| | | |
|---|---|---|
| *C12Q 1/6834* | (2018.01) | |
| *C12Q 1/6841* | (2018.01) | |
| *C12Q 1/6874* | (2018.01) | |
| *C12Q 1/6876* | (2018.01) | |
| *C12N 15/10* | (2006.01) | |

(52) U.S. Cl.
CPC ....... *C12Q 1/6834* (2013.01); *C12N 15/1065* (2013.01); *C12Q 1/6841* (2013.01); *C12Q 1/6874* (2013.01); *C12Q 1/6876* (2013.01)

(58) Field of Classification Search
CPC .. C12Q 1/6834; C12Q 1/6841; C12Q 1/6874; C12Q 1/6876; C12Q 2563/149; C12Q 2563/179; C12Q 2565/514; C12N 15/1065

See application file for complete search history.

(56) References Cited

U.S. PATENT DOCUMENTS

| | | |
|---|---|---|
| 4,514,388 A | 4/1985 | Psaledakis |
| 4,574,729 A | 3/1986 | Wells |
| 4,683,195 A | 7/1987 | Mullis |
| 4,683,202 A | 7/1987 | Mullis |
| 4,800,159 A | 1/1989 | Mullis |
| 4,883,867 A | 11/1989 | Lee |
| 4,965,188 A | 10/1990 | Mullis |
| 4,968,601 A | 11/1990 | Jacobson et al. |
| 4,988,617 A | 1/1991 | Landegren et al. |
| 5,002,882 A | 3/1991 | Lunnen |
| 5,061,049 A | 10/1991 | Hornbeck |
| 5,130,238 A | 7/1992 | Malek |
| 5,183,053 A | 2/1993 | Yeh et al. |
| 5,308,751 A | 5/1994 | Ohkawa |
| 5,321,130 A | 6/1994 | Yue |
| 5,410,030 A | 4/1995 | Yue |
| 5,436,134 A | 7/1995 | Haugland |
| 5,455,166 A | 10/1995 | Walker |

(Continued)

FOREIGN PATENT DOCUMENTS

| | | |
|---|---|---|
| AU | 2003200718 | 10/2006 |
| CN | 1273609 | 11/2000 |

(Continued)

OTHER PUBLICATIONS

U.S. Appl. No. 16/353,937, filed Mar. 14, 2019, Frisen et al.

(Continued)

*Primary Examiner* — David C Thomas
(74) *Attorney, Agent, or Firm* — Fish & Richardson P.C.

(57) ABSTRACT

A method for spatially tagging nucleic acids of a biological specimen, including steps of (a) providing a solid support comprising different nucleic acid probes that are randomly located on the solid support, wherein the different nucleic acid probes each includes a barcode sequence that differs from the barcode sequence of other randomly located probes on the solid support; (b) performing a nucleic acid detection reaction on the solid support to locate the barcode sequences on the solid support; (c) contacting a biological specimen with the solid support that has the randomly located probes; (d) hybridizing the randomly located probes to target nucleic acids from portions of the biological specimen; and (e) modifying the randomly located probes that are hybridized to the target nucleic acids, thereby producing modified probes that include the barcode sequences and a target specific modification, thereby spatially tagging the nucleic acids of the biological specimen.

30 Claims, 9 Drawing Sheets

(56) References Cited

U.S. PATENT DOCUMENTS

| | | |
|---|---|---|
| 5,472,881 A | 12/1995 | Beebe et al. |
| 5,494,810 A | 2/1996 | Barany et al. |
| 5,503,980 A | 4/1996 | Cantor |
| 5,512,439 A | 4/1996 | Hornes |
| 5,512,462 A | 4/1996 | Cheng |
| 5,559,032 A | 9/1996 | Pomeroy |
| 5,582,977 A | 12/1996 | Yue |
| 5,589,173 A | 12/1996 | O'Brien |
| 5,599,675 A | 2/1997 | Brenner |
| 5,610,287 A | 3/1997 | Nikiforov et al. |
| 5,641,658 A | 6/1997 | Adams |
| 5,648,245 A | 7/1997 | Fire et al. |
| 5,658,751 A | 8/1997 | Yue |
| 5,695,940 A | 12/1997 | Drmanac et al. |
| 5,716,825 A | 2/1998 | Hancock et al. |
| 5,750,341 A | 5/1998 | Macevicz |
| 5,763,175 A | 6/1998 | Brenner |
| 5,807,522 A | 9/1998 | Brown et al. |
| 5,830,711 A | 11/1998 | Barany et al. |
| 5,837,832 A | 11/1998 | Chee et al. |
| 5,837,860 A | 11/1998 | Anderson et al. |
| 5,854,033 A | 12/1998 | Lizardi |
| 5,863,753 A | 1/1999 | Haugland |
| 5,866,377 A | 2/1999 | Kim et al. |
| 5,871,921 A | 2/1999 | Landegren et al. |
| 5,912,148 A | 6/1999 | Eggerding |
| 5,919,626 A | 7/1999 | Shi et al. |
| 5,925,545 A | 7/1999 | Reznikoff et al. |
| 5,928,906 A | 7/1999 | Koester et al. |
| 5,958,775 A | 9/1999 | Wickstrom et al. |
| 5,965,443 A | 10/1999 | Reznikoff et al. |
| 6,013,440 A | 1/2000 | Lipshutz |
| 6,027,889 A | 2/2000 | Barany et al. |
| 6,054,274 A | 4/2000 | Sampson et al. |
| 6,060,240 A | 5/2000 | Kamb et al. |
| 6,083,761 A | 7/2000 | Kedar et al. |
| 6,130,073 A | 10/2000 | Eggerding |
| 6,136,592 A | 10/2000 | Leighton |
| 6,143,496 A | 11/2000 | Brown |
| 6,153,389 A | 11/2000 | Haarer |
| 6,159,736 A | 12/2000 | Reznikoff et al. |
| 6,165,714 A | 12/2000 | Lane et al. |
| 6,172,218 B1 | 1/2001 | Brenner |
| 6,210,891 B1 | 4/2001 | Nyren |
| 6,210,894 B1 | 4/2001 | Brennan |
| 6,214,587 B1 | 4/2001 | Dattagupta |
| 6,221,591 B1 | 4/2001 | Aerts |
| 6,221,654 B1 | 4/2001 | Quake |
| 6,251,639 B1 | 6/2001 | Kurn |
| 6,258,558 B1 | 7/2001 | Szostak |
| 6,258,568 B1 | 7/2001 | Nyren |
| 6,261,804 B1 | 7/2001 | Szostak |
| 6,265,552 B1 | 7/2001 | Schatz |
| 6,266,459 B1 | 7/2001 | Walt |
| 6,268,148 B1 | 7/2001 | Barany et al. |
| 6,274,320 B1 | 8/2001 | Rothberg |
| 6,281,804 B1 | 8/2001 | Haller |
| 6,291,180 B1 | 9/2001 | Chu |
| 6,291,187 B1 | 9/2001 | Kingsmore et al. |
| 6,300,063 B1 | 10/2001 | Lipshutz et al. |
| 6,306,597 B1 | 10/2001 | Macevicz |
| 6,309,824 B1 | 10/2001 | Drmanac |
| 6,323,009 B1 | 11/2001 | Lasken et al. |
| 6,337,472 B1 | 1/2002 | Garner et al. |
| 6,344,316 B1 | 2/2002 | Lockhart |
| 6,344,329 B1 | 2/2002 | Lizardi et al. |
| 6,355,431 B1 | 3/2002 | Chee |
| 6,368,801 B1 | 4/2002 | Faruqi |
| 6,391,937 B1 | 5/2002 | Beuhler et al. |
| 6,401,267 B1 | 6/2002 | Drmanac |
| 6,404,907 B1 | 6/2002 | Gilchrist |
| 6,416,950 B1 | 7/2002 | Lohse |
| 6,432,360 B1 | 8/2002 | Church et al. |
| 6,485,982 B1 | 11/2002 | Charlton |
| 6,503,713 B1 | 1/2003 | Rana |
| 6,506,561 B1 | 1/2003 | Cheval et al. |
| 6,518,018 B1 | 2/2003 | Szostak |
| 6,534,266 B1 | 3/2003 | Singer |
| 6,544,732 B1 | 4/2003 | Chee |
| 6,544,790 B1 | 4/2003 | Sabatini |
| 6,565,727 B1 | 5/2003 | Shenderov |
| 6,573,043 B1 | 6/2003 | Cohen et al. |
| 6,579,695 B1 | 6/2003 | Lambalot |
| 6,620,584 B1 | 9/2003 | Chee |
| 6,632,641 B1 | 10/2003 | Brennan |
| 6,673,620 B1 | 1/2004 | Loeffler |
| 6,677,160 B1 | 1/2004 | Stockman et al. |
| 6,699,710 B1 | 3/2004 | Kononen |
| 6,737,236 B1 | 5/2004 | Pieken et al. |
| 6,770,441 B2 | 8/2004 | Dickinson |
| 6,773,566 B2 | 8/2004 | Shenderov |
| 6,773,886 B2 | 8/2004 | Kaufman |
| 6,787,308 B2 | 9/2004 | Balasubramanian |
| 6,797,470 B2 | 9/2004 | Barany et al. |
| 6,800,453 B2 | 10/2004 | Labaer |
| 6,812,005 B2 | 11/2004 | Fan et al. |
| 6,828,100 B1 | 12/2004 | Ronaghi |
| 6,833,246 B2 | 12/2004 | Balasubramanian |
| 6,852,487 B1 | 2/2005 | Barany et al. |
| 6,859,570 B2 | 2/2005 | Walt |
| 6,864,052 B1 | 3/2005 | Drmanac |
| 6,867,028 B2 | 3/2005 | Janulaitis |
| 6,872,816 B1 | 3/2005 | Hall et al. |
| 6,875,572 B2 | 4/2005 | Prudent et al. |
| 6,878,515 B1 | 4/2005 | Landegren |
| 6,890,741 B2 | 5/2005 | Fan et al. |
| 6,897,023 B2 | 5/2005 | Fu |
| 6,911,132 B2 | 6/2005 | Pamula |
| 6,911,345 B2 | 6/2005 | Quake |
| 6,913,881 B1 | 7/2005 | Aizenstein et al. |
| 6,913,921 B2 | 7/2005 | Fischer |
| 6,942,968 B1 | 9/2005 | Dickinson et al. |
| 6,969,488 B2 | 11/2005 | Bridgham |
| 6,969,589 B2 | 11/2005 | Patil |
| 6,977,033 B2 | 12/2005 | Becker |
| 7,001,792 B2 | 2/2006 | Sauer et al. |
| 7,011,944 B2 | 3/2006 | Prudent et al. |
| 7,052,244 B2 | 5/2006 | Fouillet |
| 7,057,026 B2 | 6/2006 | Barnes |
| 7,083,980 B2 | 8/2006 | Reznikoff et al. |
| 7,098,041 B2 | 8/2006 | Kaylor et al. |
| 7,115,400 B1 | 10/2006 | Adessi |
| 7,118,883 B2 | 10/2006 | Inoue |
| 7,128,893 B2 | 10/2006 | Leamon et al. |
| 7,163,612 B2 | 1/2007 | Sterling |
| 7,166,431 B2 | 1/2007 | Chee et al. |
| 7,192,735 B2 | 3/2007 | Lambalot |
| 7,211,414 B2 | 5/2007 | Hardin |
| 7,223,371 B2 | 5/2007 | Hayenga et al. |
| 7,229,769 B2 | 6/2007 | Kozlov |
| 7,244,559 B2 | 7/2007 | Rothberg |
| 7,255,994 B2 | 8/2007 | Lao |
| 7,258,976 B2 | 8/2007 | Mitsuhashi |
| 7,259,258 B2 | 8/2007 | Kozlov et al. |
| 7,264,929 B2 | 9/2007 | Rothberg |
| 7,270,950 B2 | 9/2007 | Szostak |
| 7,282,328 B2 | 10/2007 | Kong et al. |
| 7,297,518 B2 | 11/2007 | Quake |
| 7,315,019 B2 | 1/2008 | Turner |
| 7,328,979 B2 | 2/2008 | Decre |
| 7,329,492 B2 | 2/2008 | Hardin |
| 7,358,047 B2 | 4/2008 | Hafner et al. |
| 7,361,488 B2 | 4/2008 | Fan et al. |
| 7,375,234 B2 | 5/2008 | Sharpless et al. |
| 7,378,242 B2 | 5/2008 | Hurt |
| 7,393,665 B2 | 7/2008 | Brenner |
| 7,405,281 B2 | 7/2008 | Xu |
| 7,407,757 B2 | 8/2008 | Brenner |
| 7,427,678 B2 | 9/2008 | Pieken et al. |
| 7,462,449 B2 | 12/2008 | Quake |
| 7,473,767 B2 | 1/2009 | Dimitrov |
| 7,499,806 B2 | 3/2009 | Kermani et al. |
| 7,501,245 B2 | 3/2009 | Quake |
| 7,534,991 B2 | 5/2009 | Miller et al. |

(56) References Cited

U.S. PATENT DOCUMENTS

| | | |
|---|---|---|
| 7,537,897 B2 | 5/2009 | Brenner |
| 7,544,473 B2 | 6/2009 | Brennan |
| 7,547,380 B2 | 6/2009 | Velev |
| 7,555,155 B2 | 6/2009 | Levenson et al. |
| 7,563,576 B2 | 7/2009 | Chee |
| 7,579,153 B2 | 8/2009 | Brenner |
| 7,582,420 B2 | 9/2009 | Oliphant et al. |
| 7,595,883 B1 | 9/2009 | El Gamal |
| 7,601,492 B2 | 10/2009 | Fu et al. |
| 7,601,498 B2 | 10/2009 | Mao |
| 7,608,434 B2 | 10/2009 | Reznikoff et al. |
| 7,611,869 B2 | 11/2009 | Fan |
| 7,635,566 B2 | 12/2009 | Brenner |
| 7,641,779 B2 | 1/2010 | Becker |
| 7,655,898 B2 | 2/2010 | Miller |
| 7,666,612 B2 | 2/2010 | Johnsson |
| 7,674,589 B2 | 3/2010 | Cohen et al. |
| 7,674,752 B2 | 3/2010 | He |
| 7,700,286 B2 | 4/2010 | Stroun et al. |
| 7,709,198 B2 | 5/2010 | Luo et al. |
| 7,754,429 B2 | 7/2010 | Rigatti |
| 7,776,547 B2 | 8/2010 | Roth |
| 7,776,567 B2 | 8/2010 | Mao |
| 7,785,869 B2 | 8/2010 | Belgrader et al. |
| 7,803,943 B2 | 9/2010 | Mao |
| 7,844,940 B2 | 11/2010 | Shin et al. |
| 7,848,553 B2 | 12/2010 | Hertel et al. |
| 7,858,321 B2 | 12/2010 | Glezer |
| 7,888,009 B2 | 2/2011 | Barany et al. |
| 7,892,747 B2 | 2/2011 | Barany et al. |
| 7,910,304 B2 | 3/2011 | Drmanac |
| 7,914,981 B2 | 3/2011 | Barany et al. |
| 7,941,279 B2 | 5/2011 | Hwang et al. |
| 7,955,794 B2 | 6/2011 | Shen et al. |
| 7,960,119 B2 | 6/2011 | Chee |
| 7,960,120 B2 | 6/2011 | Rigatti |
| 8,003,354 B2 | 8/2011 | Shen et al. |
| 8,030,477 B2 | 10/2011 | Cerrina et al. |
| 8,076,063 B2 | 12/2011 | Fan |
| 8,092,784 B2 | 1/2012 | Mao |
| 8,124,751 B2 | 2/2012 | Pierce et al. |
| 8,148,068 B2 | 4/2012 | Brenner |
| 8,148,518 B2 | 4/2012 | Buchanan |
| 8,198,028 B2 | 6/2012 | Rigatti et al. |
| 8,199,999 B2 | 6/2012 | Hoyt et al. |
| 8,206,917 B2 | 6/2012 | Chee |
| 8,207,093 B2 | 6/2012 | Szostak |
| 8,268,554 B2 | 9/2012 | Schallmeiner |
| 8,278,034 B2 | 10/2012 | Muraca |
| 8,288,103 B2 | 10/2012 | Oliphant |
| 8,288,122 B2 | 10/2012 | O'Leary et al. |
| 8,330,087 B2 | 12/2012 | Domenicali |
| 8,337,851 B2 | 12/2012 | Aukerman |
| 8,343,500 B2 | 1/2013 | Wraith |
| 8,383,338 B2 | 2/2013 | Kitzman |
| 8,415,102 B2 | 4/2013 | Geiss et al. |
| 8,431,691 B2 | 4/2013 | McKernan et al. |
| 8,460,865 B2 | 6/2013 | Chee |
| 8,462,981 B2 | 6/2013 | Determan et al. |
| 8,481,257 B2 | 7/2013 | Van Eijk |
| 8,481,258 B2 | 7/2013 | Church et al. |
| 8,481,292 B2 | 7/2013 | Casbon |
| 8,481,698 B2 | 7/2013 | Lieberman et al. |
| 8,486,625 B2 | 7/2013 | Gunderson |
| 8,507,204 B2 | 8/2013 | Pierce et al. |
| 8,519,115 B2 | 8/2013 | Webster et al. |
| 8,551,710 B2 | 10/2013 | Bernitz et al. |
| 8,568,979 B2 | 10/2013 | Stuelpnagel et al. |
| RE44,596 E | 11/2013 | Stroun et al. |
| 8,586,310 B2 | 11/2013 | Mitra |
| 8,597,891 B2 | 12/2013 | Barany et al. |
| 8,603,743 B2 | 12/2013 | Liu et al. |
| 8,604,182 B2 | 12/2013 | Luo et al. |
| 8,614,073 B2 | 12/2013 | Van Eijk |
| 8,624,016 B2 | 1/2014 | Barany et al. |
| 8,637,242 B2 | 1/2014 | Shen |
| 8,658,361 B2 | 2/2014 | Wu et al. |
| 8,685,889 B2 | 4/2014 | Van Eijk |
| 8,741,564 B2 | 6/2014 | Seligmann |
| 8,741,606 B2 | 6/2014 | Casbon |
| 8,748,103 B2 | 6/2014 | Faham et al. |
| 8,771,950 B2 | 7/2014 | Church et al. |
| 8,778,849 B2 | 7/2014 | Bowen |
| 8,785,353 B2 | 7/2014 | Van Eijk |
| 8,790,873 B2 | 7/2014 | Namsaraev et al. |
| 8,809,238 B2 | 8/2014 | Livak et al. |
| 8,815,512 B2 | 8/2014 | Van Eijk |
| 8,835,358 B2 | 9/2014 | Fodor |
| 8,865,410 B2 | 10/2014 | Shendure |
| 8,895,249 B2 | 11/2014 | Shen |
| 8,906,626 B2 | 12/2014 | Oliphant et al. |
| 8,911,945 B2 | 12/2014 | Van Eijk |
| 8,936,912 B2 | 1/2015 | Mitra |
| 8,951,726 B2 | 2/2015 | Luo et al. |
| 8,951,728 B2 | 2/2015 | Rasmussen |
| 8,951,781 B2 | 2/2015 | Reed |
| 8,986,926 B2 | 3/2015 | Ferree et al. |
| 9,005,891 B2 | 4/2015 | Sinicropi et al. |
| 9,005,935 B2 | 4/2015 | Belyaev |
| 9,023,768 B2 | 5/2015 | Van Eijk |
| 9,062,348 B1 | 6/2015 | Van Eijk |
| 9,080,210 B2 | 7/2015 | Van Eijk |
| 9,085,798 B2 | 7/2015 | Chee |
| 9,121,069 B2 | 9/2015 | Lo |
| 9,163,283 B2 | 10/2015 | Chee et al. |
| 9,194,001 B2 | 11/2015 | Brenner |
| 9,201,063 B2 | 12/2015 | Sood et al. |
| 9,217,176 B2 | 12/2015 | Faham et al. |
| 9,273,349 B2 | 3/2016 | Nguyen et al. |
| 9,290,808 B2 | 3/2016 | Fodor |
| 9,290,809 B2 | 3/2016 | Fodor |
| 9,309,556 B2 | 4/2016 | Myllykangas et al. |
| 9,328,383 B2 | 5/2016 | Van Eijk |
| 9,334,536 B2 | 5/2016 | Van Eijk |
| 9,340,830 B2 | 5/2016 | Lipson |
| 9,371,563 B2 | 6/2016 | Geiss et al. |
| 9,371,598 B2 | 6/2016 | Chee |
| 9,376,716 B2 | 6/2016 | Van Eijk |
| 9,376,717 B2 | 6/2016 | Gao et al. |
| 9,376,719 B2 | 6/2016 | Van Eijk |
| 9,404,156 B2 | 8/2016 | Hicks |
| 9,416,409 B2 | 8/2016 | Hayden |
| 9,447,459 B2 | 9/2016 | Van Eijk |
| 9,453,256 B2 | 9/2016 | Van Eijk |
| 9,493,820 B2 | 11/2016 | Van Eijk |
| 9,506,061 B2 | 11/2016 | Brown |
| 9,512,422 B2 | 12/2016 | Barnard et al. |
| 9,512,487 B2 | 12/2016 | Faham et al. |
| 9,518,980 B2 | 12/2016 | Looger et al. |
| 9,541,504 B2 | 1/2017 | Hoyt |
| 9,557,330 B2 | 1/2017 | Siciliano et al. |
| 9,574,230 B2 | 2/2017 | Van Eijk |
| 9,582,877 B2 | 2/2017 | Fu |
| 9,593,365 B2 | 3/2017 | Frisen et al. |
| 9,598,728 B2 | 3/2017 | Barany et al. |
| 9,624,538 B2 | 4/2017 | Church et al. |
| 9,644,204 B2 | 5/2017 | Hindson et al. |
| 9,657,335 B2 | 5/2017 | Van Eijk |
| 9,670,542 B2 | 6/2017 | Van Eijk |
| 9,694,361 B2 | 7/2017 | Bharadwaj |
| 9,702,004 B2 | 7/2017 | Van Eijk |
| 9,714,446 B2 | 7/2017 | Webster et al. |
| 9,714,937 B2 | 7/2017 | Dunaway |
| 9,727,810 B2 | 8/2017 | Fodor et al. |
| 9,745,627 B2 | 8/2017 | Van Eijk |
| 9,777,324 B2 | 10/2017 | Van Eijk |
| 9,778,155 B2 | 10/2017 | Gradinaru et al. |
| 9,783,841 B2 | 10/2017 | Nolan et al. |
| 9,790,476 B2 | 10/2017 | Gloeckner et al. |
| 9,816,134 B2 | 11/2017 | Namsaraev |
| 9,834,814 B2 | 12/2017 | Peter et al. |
| 9,850,536 B2 | 12/2017 | Oliphant et al. |
| 9,856,521 B2 | 1/2018 | Stevens et al. |
| 9,868,979 B2 | 1/2018 | Chee et al. |

(56) References Cited

U.S. PATENT DOCUMENTS

| | | |
|---|---|---|
| 9,879,313 B2 | 1/2018 | Chee et al. |
| 9,889,422 B2 | 2/2018 | Smith et al. |
| 9,896,721 B2 | 2/2018 | Van Eijk |
| 9,898,576 B2 | 2/2018 | Van Eijk |
| 9,898,577 B2 | 2/2018 | Van Eijk |
| 9,902,950 B2 | 2/2018 | Church et al. |
| 9,902,991 B2 | 2/2018 | Sinicropi et al. |
| 9,909,167 B2 | 3/2018 | Samusik et al. |
| 9,938,566 B2 | 4/2018 | Shepard et al. |
| 9,957,550 B2 | 5/2018 | Yeakley et al. |
| 9,958,454 B2 | 5/2018 | Kozlov et al. |
| 9,975,122 B2 | 5/2018 | Masquelier et al. |
| 10,002,316 B2 | 6/2018 | Fodor et al. |
| 10,011,872 B1 | 7/2018 | Belgrader et al. |
| 10,023,907 B2 | 7/2018 | Van Eijk |
| 10,030,261 B2 | 7/2018 | Frisen et al. |
| 10,032,064 B2 | 7/2018 | Hoyt |
| 10,035,992 B2 | 7/2018 | Gloeckner et al. |
| 10,041,949 B2 | 8/2018 | Bendall et al. |
| 10,049,770 B2 | 8/2018 | Madabhushi et al. |
| 10,053,723 B2 | 8/2018 | Hindson et al. |
| 10,059,989 B2 | 8/2018 | Giresi et al. |
| 10,059,990 B2 | 8/2018 | Boyden et al. |
| 10,071,377 B2 | 9/2018 | Bharadwaj et al. |
| 10,072,104 B2 | 9/2018 | Winnik et al. |
| 10,078,895 B2 | 9/2018 | Madabhushi et al. |
| 10,095,832 B2 | 10/2018 | Van Eijk |
| 10,126,242 B2 | 11/2018 | Miller et al. |
| 10,138,509 B2 | 11/2018 | Church et al. |
| 10,144,966 B2 | 12/2018 | Cantor |
| 10,179,932 B2 | 1/2019 | Church et al. |
| 10,196,691 B2 | 2/2019 | Harkin et al. |
| 10,221,461 B2 | 3/2019 | Robins et al. |
| 10,227,639 B2 | 3/2019 | Levner et al. |
| 10,246,700 B2 | 4/2019 | Dunaway et al. |
| 10,246,752 B2 | 4/2019 | Faham et al. |
| 10,266,874 B2 | 4/2019 | Weissleder et al. |
| 10,266,876 B2 | 4/2019 | Cai et al. |
| 10,266,888 B2 | 4/2019 | Daugharthy et al. |
| 10,267,808 B2 | 4/2019 | Cai |
| 10,273,541 B2 | 4/2019 | Hindson et al. |
| 10,308,982 B2 | 6/2019 | Chee |
| 10,309,879 B2 | 6/2019 | Chen et al. |
| 10,317,321 B2 | 6/2019 | Tillberg et al. |
| 10,357,771 B2 | 7/2019 | Bharadwaj |
| 10,364,457 B2 | 7/2019 | Wassie et al. |
| 10,370,698 B2 | 8/2019 | Nolan et al. |
| 10,405,750 B2 | 9/2019 | Wang et al. |
| 10,415,080 B2 | 9/2019 | Dunaway et al. |
| 10,457,980 B2 | 10/2019 | Cai et al. |
| 10,465,235 B2 | 11/2019 | Gullberg et al. |
| 10,472,669 B2 | 11/2019 | Chee |
| 10,480,022 B2 | 11/2019 | Chee |
| 10,480,029 B2 | 11/2019 | Bent et al. |
| 10,494,662 B2 | 12/2019 | Church et al. |
| 10,494,667 B2 | 12/2019 | Chee |
| 10,495,554 B2 | 12/2019 | Deisseroth et al. |
| 10,501,777 B2 | 12/2019 | Beechem et al. |
| 10,501,791 B2 | 12/2019 | Church et al. |
| 10,510,435 B2 | 12/2019 | Cai et al. |
| 10,526,649 B2 | 1/2020 | Chen et al. |
| 10,544,403 B2 | 1/2020 | Gloeckner et al. |
| 10,545,075 B2 | 1/2020 | Deisseroth et al. |
| 10,550,429 B2 | 2/2020 | Harada et al. |
| 10,580,128 B2 | 3/2020 | Miller |
| 10,612,079 B2 | 4/2020 | Chee |
| 10,619,196 B1 | 4/2020 | Chee |
| 10,633,648 B2 | 4/2020 | Seelig et al. |
| 10,640,816 B2 | 5/2020 | Beechem et al. |
| 10,640,826 B2 | 5/2020 | Church et al. |
| 10,655,163 B2 | 5/2020 | Weissleder et al. |
| 10,662,467 B2 | 5/2020 | Chee |
| 10,662,468 B2 | 5/2020 | Chee |
| 10,669,569 B2 | 6/2020 | Gullberg et al. |
| 10,697,013 B1 | 6/2020 | Brenner et al. |
| 10,724,078 B2 | 7/2020 | Van Driel et al. |
| 10,725,027 B2 | 7/2020 | Bell |
| 10,746,981 B2 | 8/2020 | Tomer et al. |
| 10,767,223 B1 | 9/2020 | Brenner et al. |
| 10,774,372 B2 | 9/2020 | Chee et al. |
| 10,774,374 B2 | 9/2020 | Frisen et al. |
| 10,787,701 B2 | 9/2020 | Chee |
| 10,794,802 B2 | 10/2020 | Gradinaru et al. |
| 10,802,262 B2 | 10/2020 | Tomer et al. |
| 10,815,519 B2 | 10/2020 | Husain et al. |
| 10,829,803 B2 | 11/2020 | Terbrueggen et al. |
| 10,844,426 B2 | 11/2020 | Daugharthy et al. |
| 10,858,698 B2 | 12/2020 | Church et al. |
| 10,858,702 B2 | 12/2020 | Lucero et al. |
| 10,872,679 B2 | 12/2020 | Cai et al. |
| 10,913,975 B2 | 2/2021 | So et al. |
| 10,914,730 B2 | 2/2021 | Chee et al. |
| 10,927,403 B2 | 2/2021 | Chee et al. |
| 10,961,566 B2 | 3/2021 | Chee |
| 10,962,532 B2 | 3/2021 | Chee |
| 10,964,001 B2 | 3/2021 | Miller |
| 10,982,268 B2 | 4/2021 | Chee |
| 10,983,113 B2 | 4/2021 | Chee |
| 10,995,361 B2 | 5/2021 | Chen et al. |
| 10,996,219 B2 | 5/2021 | Chee et al. |
| 11,001,878 B1 | 5/2021 | Chee et al. |
| 11,001,879 B1 | 5/2021 | Chee et al. |
| 11,008,607 B2 | 5/2021 | Chee |
| 11,008,608 B2 | 5/2021 | Samusik et al. |
| 11,046,996 B1 | 6/2021 | Chee et al. |
| 11,067,567 B2 | 7/2021 | Chee |
| 11,104,936 B2 | 8/2021 | Zhang et al. |
| 11,118,216 B2 | 9/2021 | Koshinsky et al. |
| 11,156,603 B2 | 10/2021 | Chee |
| 11,162,132 B2 | 11/2021 | Frisen et al. |
| 11,168,350 B2 | 11/2021 | Nolan et al. |
| 11,208,684 B2 | 12/2021 | Chee |
| 11,286,515 B2 | 3/2022 | Chee et al. |
| 11,293,917 B2 | 4/2022 | Chee |
| 11,299,774 B2 | 4/2022 | Frisen et al. |
| 11,313,856 B2 | 4/2022 | Chee |
| 11,332,790 B2 | 5/2022 | Chell et al. |
| 11,352,659 B2 | 6/2022 | Frisen et al. |
| 11,352,667 B2 | 6/2022 | Hauling et al. |
| 11,359,228 B2 | 6/2022 | Chee et al. |
| 11,365,442 B2 | 6/2022 | Chee |
| 11,371,086 B2 | 6/2022 | Chee |
| 11,384,386 B2 | 7/2022 | Chee |
| 11,390,912 B2 | 7/2022 | Frisen et al. |
| 11,401,545 B2 | 8/2022 | Chee |
| 11,407,992 B2 | 8/2022 | Dadhwal |
| 11,408,029 B2 | 8/2022 | Katiraee et al. |
| 11,434,524 B2 | 9/2022 | Ramachandran Iyer et al. |
| 11,447,807 B2 | 9/2022 | Church et al. |
| 11,479,809 B2 | 10/2022 | Frisen et al. |
| 11,479,810 B1 | 10/2022 | Chee |
| 11,492,612 B1 | 11/2022 | Dadhwal |
| 11,505,828 B2 | 11/2022 | Chell et al. |
| 11,512,308 B2 | 11/2022 | Gallant et al. |
| 11,519,022 B2 | 12/2022 | Chee |
| 11,519,033 B2 | 12/2022 | Schnall-Levin et al. |
| 11,530,438 B2 | 12/2022 | Persson et al. |
| 11,535,887 B2 | 12/2022 | Gallant et al. |
| 11,542,543 B2 | 1/2023 | Chee |
| 11,549,138 B2 | 1/2023 | Chee |
| 11,560,587 B2 | 1/2023 | Chee |
| 11,560,592 B2 | 1/2023 | Chew et al. |
| 11,560,593 B2 | 1/2023 | Chell et al. |
| 11,592,447 B2 | 2/2023 | Uytingco et al. |
| 11,608,498 B2 | 3/2023 | Gallant et al. |
| 11,608,520 B2 | 3/2023 | Galonska et al. |
| 11,613,773 B2 | 3/2023 | Frisen et al. |
| 11,618,897 B2 | 4/2023 | Kim et al. |
| 11,618,918 B2 | 4/2023 | Chee et al. |
| 11,624,063 B2 | 4/2023 | Dadhwal |
| 11,624,086 B2 | 4/2023 | Uytingco et al. |
| 11,634,756 B2 | 4/2023 | Chee |
| 11,649,485 B2 | 5/2023 | Yin et al. |
| 11,661,626 B2 | 5/2023 | Katiraee et al. |

(56) References Cited

U.S. PATENT DOCUMENTS

| | | |
|---|---|---|
| 2001/0039029 A1 | 11/2001 | Nemori et al. |
| 2001/0055764 A1 | 12/2001 | Empendocles et al. |
| 2002/0006477 A1 | 1/2002 | Shishido et al. |
| 2002/0040275 A1 | 4/2002 | Cravatt |
| 2002/0045169 A1 | 4/2002 | Shoemaker et al. |
| 2002/0045272 A1 | 4/2002 | McDevitt et al. |
| 2002/0048766 A1 | 4/2002 | Doyle et al. |
| 2002/0051986 A1 | 5/2002 | Baez et al. |
| 2002/0055100 A1 | 5/2002 | Kawashima |
| 2002/0058250 A1 | 5/2002 | Firth |
| 2002/0064779 A1 | 5/2002 | Landegren |
| 2002/0086441 A1 | 7/2002 | Baranov et al. |
| 2002/0132246 A1 | 9/2002 | Kallioniemi et al. |
| 2002/0137031 A1 | 9/2002 | Wolber |
| 2002/0150909 A1 | 10/2002 | Stuelpnagel |
| 2002/0164611 A1 | 11/2002 | Bamdad |
| 2002/0168645 A1 | 11/2002 | Taylor |
| 2003/0017451 A1 | 1/2003 | Wang et al. |
| 2003/0022207 A1 | 1/2003 | Balasubramanian |
| 2003/0040035 A1 | 2/2003 | Slamon |
| 2003/0064398 A1 | 4/2003 | Barnes |
| 2003/0073086 A1 | 4/2003 | Guire et al. |
| 2003/0087232 A1 | 5/2003 | Christians |
| 2003/0096323 A1 | 5/2003 | James |
| 2003/0113713 A1 | 6/2003 | Glezer |
| 2003/0124595 A1 | 7/2003 | Lizardi |
| 2003/0134279 A1 | 7/2003 | Isola et al. |
| 2003/0138879 A1 | 7/2003 | Lambalot |
| 2003/0148335 A1 | 8/2003 | Shen et al. |
| 2003/0153850 A1 | 8/2003 | Davis et al. |
| 2003/0162216 A1 | 8/2003 | Gold |
| 2003/0165948 A1 | 9/2003 | Alsmadi et al. |
| 2003/0170637 A1 | 9/2003 | Pirrung et al. |
| 2003/0175844 A1 | 9/2003 | Nadler et al. |
| 2003/0175947 A1 | 9/2003 | Liu et al. |
| 2003/0190744 A1 | 10/2003 | McGarry et al. |
| 2003/0205632 A1 | 11/2003 | Kim et al. |
| 2003/0215936 A1 | 11/2003 | Kallioniemi et al. |
| 2003/0224419 A1 | 12/2003 | Corcoran |
| 2003/0232348 A1 | 12/2003 | Jones et al. |
| 2003/0232382 A1 | 12/2003 | Brennan |
| 2003/0235535 A1 | 12/2003 | Zhou |
| 2003/0235852 A1 | 12/2003 | Roberts |
| 2003/0235854 A1 | 12/2003 | Chan et al. |
| 2004/0002090 A1 | 1/2004 | Mayer et al. |
| 2004/0019005 A1 | 1/2004 | Van Ness |
| 2004/0023320 A1 | 2/2004 | Steiner et al. |
| 2004/0033499 A1 | 2/2004 | Ilsley et al. |
| 2004/0050699 A1 | 3/2004 | Goncalves |
| 2004/0067492 A1 | 4/2004 | Peng et al. |
| 2004/0067493 A1 | 4/2004 | Matsuzaki |
| 2004/0082059 A1 | 4/2004 | Webb |
| 2004/0096853 A1 | 5/2004 | Mayer |
| 2004/0106110 A1 | 6/2004 | Balasubramanian |
| 2004/0112442 A1 | 6/2004 | Maerkl |
| 2004/0121456 A1 | 6/2004 | Fischer |
| 2004/0175822 A1 | 9/2004 | Timperman et al. |
| 2004/0219588 A1 | 11/2004 | Furuta |
| 2004/0224326 A1 | 11/2004 | Kim et al. |
| 2004/0235103 A1 | 11/2004 | Reznikoff et al. |
| 2004/0248325 A1 | 12/2004 | Bukusoglu et al. |
| 2004/0259105 A1 | 12/2004 | Fan et al. |
| 2005/0003431 A1 | 1/2005 | Wucherpfennig |
| 2005/0014203 A1 | 1/2005 | Darfler et al. |
| 2005/0019776 A1 | 1/2005 | Callow et al. |
| 2005/0019842 A1 | 1/2005 | Prober et al. |
| 2005/0026188 A1 | 2/2005 | Van Kessel |
| 2005/0037362 A1 | 2/2005 | Remacle et al. |
| 2005/0037393 A1 | 2/2005 | Gunderson et al. |
| 2005/0042695 A1 | 2/2005 | Meares et al. |
| 2005/0048580 A1 | 3/2005 | Labaer |
| 2005/0064460 A1 | 3/2005 | Holliger et al. |
| 2005/0079520 A1 | 4/2005 | Wu |
| 2005/0095627 A1 | 5/2005 | Kolman et al. |
| 2005/0100900 A1 | 5/2005 | Kawashima et al. |
| 2005/0116161 A1 | 6/2005 | Hafeman et al. |
| 2005/0130173 A1 | 6/2005 | Leamon et al. |
| 2005/0130188 A1 | 6/2005 | Walt |
| 2005/0136414 A1 | 6/2005 | Gunderson et al. |
| 2005/0164292 A1 | 7/2005 | Farooqui |
| 2005/0179746 A1 | 8/2005 | Roux et al. |
| 2005/0191656 A1 | 9/2005 | Drmanac et al. |
| 2005/0191698 A1 | 9/2005 | Chee et al. |
| 2005/0196786 A1 | 9/2005 | Levy |
| 2005/0202433 A1 | 9/2005 | Van Beuningen |
| 2005/0227271 A1 | 10/2005 | Kwon |
| 2005/0239119 A1 | 10/2005 | Tsukada et al. |
| 2005/0239192 A1 | 10/2005 | Nasarabadi et al. |
| 2005/0244850 A1 | 11/2005 | Huang |
| 2005/0255548 A1 | 11/2005 | Lipovsek et al. |
| 2005/0257284 A1 | 11/2005 | Nakajima et al. |
| 2005/0260653 A1 | 11/2005 | LaBaer |
| 2005/0266417 A1 | 12/2005 | Barany et al. |
| 2006/0003394 A1 | 1/2006 | Song |
| 2006/0039823 A1 | 2/2006 | Yamakawa et al. |
| 2006/0046313 A1 | 3/2006 | Roth |
| 2006/0063160 A1 | 3/2006 | West et al. |
| 2006/0079453 A1 | 4/2006 | Sidney et al. |
| 2006/0084078 A1 | 4/2006 | Zhao |
| 2006/0105352 A1 | 5/2006 | Qiao et al. |
| 2006/0110739 A1 | 5/2006 | Heyduk |
| 2006/0134669 A1 | 6/2006 | Casasanta |
| 2006/0154286 A1 | 7/2006 | Kong et al. |
| 2006/0164490 A1 | 7/2006 | Kim et al. |
| 2006/0183150 A1 | 8/2006 | Cohen et al. |
| 2006/0188875 A1 | 8/2006 | Cox et al. |
| 2006/0188901 A1 | 8/2006 | Barnes et al. |
| 2006/0188906 A1 | 8/2006 | Kim et al. |
| 2006/0194331 A1 | 8/2006 | Pamula et al. |
| 2006/0199183 A1 | 9/2006 | Valat et al. |
| 2006/0199207 A1 | 9/2006 | Matysiak |
| 2006/0211001 A1 | 9/2006 | Yu et al. |
| 2006/0216721 A1 | 9/2006 | Kozlov et al. |
| 2006/0216775 A1 | 9/2006 | Burkart et al. |
| 2006/0228758 A1 | 10/2006 | Muchhal et al. |
| 2006/0240439 A1 | 10/2006 | Smith et al. |
| 2006/0263789 A1 | 11/2006 | Kincaid |
| 2006/0275782 A1 | 12/2006 | Gunderson et al. |
| 2006/0275799 A1 | 12/2006 | Banetjee et al. |
| 2006/0281109 A1 | 12/2006 | Barr Ost et al. |
| 2007/0003954 A1 | 1/2007 | Kodadek et al. |
| 2007/0014810 A1 | 1/2007 | Baker et al. |
| 2007/0020625 A1 | 1/2007 | Duchaud et al. |
| 2007/0020640 A1 | 1/2007 | McCloskey et al. |
| 2007/0020669 A1 | 1/2007 | Ericsson |
| 2007/0023292 A1 | 2/2007 | Kim et al. |
| 2007/0026430 A1 | 2/2007 | Andersen et al. |
| 2007/0036511 A1 | 2/2007 | Lundquist et al. |
| 2007/0048812 A1 | 3/2007 | Moravec et al. |
| 2007/0054288 A1 | 3/2007 | Su et al. |
| 2007/0087360 A1 | 4/2007 | Boyd |
| 2007/0099208 A1 | 5/2007 | Drmanac et al. |
| 2007/0116612 A1 | 5/2007 | Williamson |
| 2007/0128624 A1 | 6/2007 | Gormley et al. |
| 2007/0128656 A1 | 6/2007 | Agrawal |
| 2007/0134723 A1 | 6/2007 | Kozlov et al. |
| 2007/0141718 A1 | 6/2007 | Bui et al. |
| 2007/0161020 A1 | 7/2007 | Luo et al. |
| 2007/0161029 A1 | 7/2007 | Li et al. |
| 2007/0166705 A1 | 7/2007 | Milton et al. |
| 2007/0166725 A1 | 7/2007 | McBride et al. |
| 2007/0172873 A1 | 7/2007 | Brenner et al. |
| 2007/0178503 A1 | 8/2007 | Jiang |
| 2007/0207482 A1 | 9/2007 | Church et al. |
| 2007/0215466 A1 | 9/2007 | Okada |
| 2007/0231823 A1 | 10/2007 | McKernan |
| 2007/0243634 A1 | 10/2007 | Pamula et al. |
| 2007/0251824 A1 | 11/2007 | Patton |
| 2007/0254305 A1 | 11/2007 | Paik et al. |
| 2007/0264656 A1 | 11/2007 | Kawamura |
| 2007/0269805 A1 | 11/2007 | Hogers |
| 2007/0280517 A1 | 12/2007 | De La Torre-Bueno et al. |
| 2008/0003586 A1 | 1/2008 | Hyde et al. |
| 2008/0009420 A1 | 1/2008 | Schroth et al. |

(56) References Cited

U.S. PATENT DOCUMENTS

| | | |
|---|---|---|
| 2008/0032301 A1 | 2/2008 | Rank et al. |
| 2008/0038734 A1 | 2/2008 | Sorge et al. |
| 2008/0047835 A1 | 2/2008 | MacConnell |
| 2008/0071071 A1 | 3/2008 | LaBaer et al. |
| 2008/0108082 A1 | 5/2008 | Rank et al. |
| 2008/0108804 A1 | 5/2008 | Hayashizaki et al. |
| 2008/0124252 A1 | 5/2008 | Marchand et al. |
| 2008/0124810 A1 | 5/2008 | Terbrueggen et al. |
| 2008/0128627 A1 | 6/2008 | Lundquist et al. |
| 2008/0132429 A1 | 6/2008 | Perov et al. |
| 2008/0145616 A1 | 6/2008 | Gharib et al. |
| 2008/0153086 A1 | 6/2008 | Wong |
| 2008/0160580 A1 | 7/2008 | Adessi et al. |
| 2008/0199929 A1 | 8/2008 | Yeung et al. |
| 2008/0220434 A1 | 9/2008 | Thomas |
| 2008/0220981 A1 | 9/2008 | McGregor |
| 2008/0261204 A1 | 10/2008 | Lexow |
| 2008/0280773 A1 | 11/2008 | Fedurco et al. |
| 2008/0286795 A1 | 11/2008 | Kawashima et al. |
| 2008/0293046 A1 | 11/2008 | Allawi et al. |
| 2008/0293591 A1 | 11/2008 | Taussig et al. |
| 2008/0312103 A1 | 12/2008 | Nemoto et al. |
| 2009/0005252 A1 | 1/2009 | Drmanac et al. |
| 2009/0006002 A1 | 1/2009 | Honisch et al. |
| 2009/0018024 A1 | 1/2009 | Church et al. |
| 2009/0026082 A1 | 1/2009 | Rothberg et al. |
| 2009/0036323 A1 | 2/2009 | van Eijk et al. |
| 2009/0062148 A1 | 3/2009 | Goldberg |
| 2009/0082212 A1 | 3/2009 | Williams |
| 2009/0099041 A1 | 4/2009 | Church et al. |
| 2009/0105959 A1 | 4/2009 | Braverman et al. |
| 2009/0117573 A1 | 5/2009 | Fu et al. |
| 2009/0127589 A1 | 5/2009 | Rothberg et al. |
| 2009/0155781 A1 | 6/2009 | Drmanac et al. |
| 2009/0169089 A1 | 7/2009 | Hunt et al. |
| 2009/0170713 A1 | 7/2009 | van Eijk et al. |
| 2009/0192044 A1 | 7/2009 | Fouillet |
| 2009/0197326 A1 | 8/2009 | El Gamal et al. |
| 2009/0202998 A1 | 8/2009 | Schlumpberger et al. |
| 2009/0215633 A1 | 8/2009 | van Eijk et al. |
| 2009/0233802 A1 | 9/2009 | Bignell et al. |
| 2009/0239232 A1 | 9/2009 | Kurn |
| 2009/0253163 A1 | 10/2009 | Xie et al. |
| 2009/0253581 A1 | 10/2009 | van Eijk et al. |
| 2009/0253582 A1 | 10/2009 | Pena et al. |
| 2009/0264299 A1 | 10/2009 | Drmanac et al. |
| 2009/0280487 A1 | 11/2009 | Hung et al. |
| 2009/0283407 A1 | 11/2009 | Van Eijk |
| 2009/0289184 A1 | 11/2009 | Deininger |
| 2009/0291854 A1 | 11/2009 | Weisinger-Mayr et al. |
| 2009/0305237 A1 | 12/2009 | Cantor et al. |
| 2009/0312193 A1 | 12/2009 | Kim et al. |
| 2009/0321262 A1 | 12/2009 | Adachi et al. |
| 2010/0009871 A1 | 1/2010 | Reed et al. |
| 2010/0014537 A1 | 1/2010 | Jacquet et al. |
| 2010/0035249 A1 | 2/2010 | Hayashizaki et al. |
| 2010/0055733 A1 | 3/2010 | Lutolf et al. |
| 2010/0069263 A1 | 3/2010 | Shendure et al. |
| 2010/0096266 A1 | 4/2010 | Kim et al. |
| 2010/0099103 A1 | 4/2010 | Hsieh et al. |
| 2010/0105052 A1 | 4/2010 | Drmanac et al. |
| 2010/0105112 A1 | 4/2010 | Heltze et al. |
| 2010/0111768 A1 | 5/2010 | Banerjee et al. |
| 2010/0113302 A1 | 5/2010 | Williams |
| 2010/0120043 A1 | 5/2010 | Sood et al. |
| 2010/0120097 A1 | 5/2010 | Matz et al. |
| 2010/0120098 A1 | 5/2010 | Grunenwald et al. |
| 2010/0126862 A1 | 5/2010 | Sabin et al. |
| 2010/0129874 A1 | 5/2010 | Mitra et al. |
| 2010/0137143 A1 | 6/2010 | Rothberg et al. |
| 2010/0145037 A1 | 6/2010 | Makarov et al. |
| 2010/0151464 A1 | 6/2010 | Stuelpnagel et al. |
| 2010/0151511 A1 | 6/2010 | Gereenizer et al. |
| 2010/0159446 A1 | 6/2010 | Haff et al. |
| 2010/0173384 A1 | 7/2010 | Johnsson et al. |
| 2010/0184614 A1 | 7/2010 | Ye et al. |
| 2010/0184618 A1 | 7/2010 | Namsaraev et al. |
| 2010/0210475 A1 | 8/2010 | Lee et al. |
| 2010/0227329 A1 | 9/2010 | Cuppens |
| 2010/0267590 A1 | 10/2010 | Grudzien et al. |
| 2010/0273219 A1 | 10/2010 | May et al. |
| 2010/0273679 A1 | 10/2010 | Cuppoletti et al. |
| 2010/0282617 A1 | 11/2010 | Rothberg et al. |
| 2010/0303722 A1 | 12/2010 | Jin et al. |
| 2011/0024511 A1 | 2/2011 | Rietzler et al. |
| 2011/0027772 A1 | 2/2011 | Ahn et al. |
| 2011/0028685 A1 | 2/2011 | Purkayastha et al. |
| 2011/0033854 A1 | 2/2011 | Drmanac et al. |
| 2011/0045462 A1 | 2/2011 | Fu et al. |
| 2011/0048951 A1 | 3/2011 | Wu |
| 2011/0059436 A1 | 3/2011 | Hardin et al. |
| 2011/0059865 A1 | 3/2011 | Smith et al. |
| 2011/0086774 A1 | 4/2011 | Dunaway |
| 2011/0111409 A1 | 5/2011 | Sinicropi et al. |
| 2011/0151451 A1 | 6/2011 | Lemaire et al. |
| 2011/0152111 A1 | 6/2011 | Fan et al. |
| 2011/0172115 A1 | 7/2011 | Thompson et al. |
| 2011/0177518 A1 | 7/2011 | Kartalov et al. |
| 2011/0201515 A1 | 8/2011 | Webster et al. |
| 2011/0207134 A1 | 8/2011 | Faham et al. |
| 2011/0223613 A1 | 9/2011 | Gut |
| 2011/0244448 A1 | 10/2011 | Shirai et al. |
| 2011/0245101 A1 | 10/2011 | Chee et al. |
| 2011/0245111 A1 | 10/2011 | Chee |
| 2011/0275077 A1 | 11/2011 | James |
| 2011/0287435 A1 | 11/2011 | Grunenwald et al. |
| 2012/0021930 A1 | 1/2012 | Schoen et al. |
| 2012/0046175 A1 | 2/2012 | Rodesch et al. |
| 2012/0046178 A1 | 2/2012 | Van Den Boom et al. |
| 2012/0065081 A1 | 3/2012 | Chee |
| 2012/0077693 A1 | 3/2012 | Cazalis et al. |
| 2012/0129248 A1 | 5/2012 | Chee et al. |
| 2012/0135871 A1 | 5/2012 | van Eijk et al. |
| 2012/0142014 A1 | 6/2012 | Cai |
| 2012/0156728 A1 | 6/2012 | Li et al. |
| 2012/0157322 A1 | 6/2012 | Myllykangas |
| 2012/0160683 A1 | 6/2012 | Ye et al. |
| 2012/0195810 A1 | 8/2012 | Cohen et al. |
| 2012/0196297 A1 | 8/2012 | Yost et al. |
| 2012/0202698 A1 | 8/2012 | van Eijk et al. |
| 2012/0202704 A1 | 8/2012 | Fan et al. |
| 2012/0220479 A1 | 8/2012 | Ericsson et al. |
| 2012/0245053 A1 | 9/2012 | Shirai et al. |
| 2012/0252702 A1 | 10/2012 | Muratani et al. |
| 2012/0258871 A1 | 10/2012 | Kozlov et al. |
| 2012/0270305 A1 | 10/2012 | Reed et al. |
| 2012/0270748 A1 | 10/2012 | Chee et al. |
| 2012/0279954 A1 | 11/2012 | Ceremony et al. |
| 2012/0289414 A1 | 11/2012 | Mitra et al. |
| 2012/0301925 A1 | 11/2012 | Belyaev |
| 2012/0322099 A1 | 12/2012 | Lapen et al. |
| 2013/0005594 A1 | 1/2013 | Terbrueggen et al. |
| 2013/0005600 A1 | 1/2013 | Olek |
| 2013/0035239 A1 | 2/2013 | Kong et al. |
| 2013/0052331 A1 | 2/2013 | Kram et al. |
| 2013/0065768 A1 | 3/2013 | Zheng et al. |
| 2013/0065788 A1 | 3/2013 | Glezer et al. |
| 2013/0079232 A1 | 3/2013 | Kain et al. |
| 2013/0096033 A1 | 4/2013 | Routenberg |
| 2013/0109595 A1 | 5/2013 | Routenberg |
| 2013/0122516 A1 | 5/2013 | Hong et al. |
| 2013/0171621 A1 | 7/2013 | Luo et al. |
| 2013/0202718 A1 | 8/2013 | Pepin et al. |
| 2013/0211249 A1 | 8/2013 | Barnett et al. |
| 2013/0244884 A1 | 9/2013 | Jacobson et al. |
| 2013/0260372 A1 | 10/2013 | Buermann et al. |
| 2013/0261019 A1 | 10/2013 | Lin et al. |
| 2013/0296174 A1 | 11/2013 | Peumans |
| 2013/0302801 A1 | 11/2013 | Asbury et al. |
| 2013/0338042 A1 | 12/2013 | Shen et al. |
| 2014/0065609 A1 | 3/2014 | Hicks et al. |
| 2014/0066318 A1 | 3/2014 | Frisen et al. |
| 2014/0079923 A1 | 3/2014 | George et al. |
| 2014/0080715 A1 | 3/2014 | Lo et al. |

(56) References Cited

U.S. PATENT DOCUMENTS

| | | |
|---|---|---|
| 2014/0121118 A1 | 5/2014 | Warner |
| 2014/0155274 A1 | 6/2014 | Xie et al. |
| 2014/0155295 A1 | 6/2014 | Hindson et al. |
| 2014/0213533 A1 | 7/2014 | Suthanthiran et al. |
| 2014/0227705 A1 | 8/2014 | Vogelstein et al. |
| 2014/0243224 A1 | 8/2014 | Barnard et al. |
| 2014/0270435 A1 | 9/2014 | Dunn |
| 2014/0274731 A1 | 9/2014 | Raymond et al. |
| 2014/0296081 A1 | 10/2014 | Diehn et al. |
| 2014/0323330 A1 | 10/2014 | Glezer et al. |
| 2014/0342921 A1 | 11/2014 | Weiner |
| 2014/0378345 A1 | 12/2014 | Hindson et al. |
| 2015/0000854 A1 | 1/2015 | Gann-Fetter et al. |
| 2015/0005447 A1 | 1/2015 | Berti et al. |
| 2015/0051085 A1 | 2/2015 | Vogelstein et al. |
| 2015/0072867 A1 | 3/2015 | Soldatov |
| 2015/0087027 A1 | 3/2015 | Makarov et al. |
| 2015/0125053 A1 | 5/2015 | Vieveli et al. |
| 2015/0148239 A1 | 5/2015 | Jon |
| 2015/0219618 A1 | 8/2015 | Krishnan et al. |
| 2015/0246336 A1 | 9/2015 | Somoza et al. |
| 2015/0292988 A1 | 10/2015 | Bharadwaj et al. |
| 2015/0344942 A1 | 12/2015 | Frisen et al. |
| 2015/0376609 A1 | 12/2015 | Hindson et al. |
| 2016/0003812 A1 | 1/2016 | Porreca et al. |
| 2016/0019337 A1 | 1/2016 | Roberts et al. |
| 2016/0024555 A1 | 1/2016 | Church et al. |
| 2016/0024576 A1 | 1/2016 | Chee |
| 2016/0033496 A1 | 2/2016 | Chou et al. |
| 2016/0108458 A1 | 4/2016 | Frei et al. |
| 2016/0122817 A1 | 5/2016 | Jarosz et al. |
| 2016/0138091 A1 | 5/2016 | Chee et al. |
| 2016/0145677 A1 | 5/2016 | Chee et al. |
| 2016/0194692 A1 | 7/2016 | Gore et al. |
| 2016/0253584 A1 | 9/2016 | Fodor et al. |
| 2016/0289669 A1 | 10/2016 | Fan et al. |
| 2016/0289740 A1 | 10/2016 | Fu et al. |
| 2016/0298180 A1 | 10/2016 | Chee |
| 2016/0299165 A1 | 10/2016 | Zhou |
| 2016/0304952 A1 | 10/2016 | Boyden et al. |
| 2016/0305856 A1 | 10/2016 | Boyden et al. |
| 2016/0333403 A1 | 11/2016 | Chee |
| 2016/0369329 A1 | 12/2016 | Cai et al. |
| 2016/0376642 A1 | 12/2016 | Landegren et al. |
| 2017/0009278 A1 | 1/2017 | Söderberg et al. |
| 2017/0016053 A1 | 1/2017 | Beechem et al. |
| 2017/0016909 A1 | 1/2017 | Beechem et al. |
| 2017/0029872 A1 | 2/2017 | Bhattacharyya et al. |
| 2017/0029875 A1 | 2/2017 | Zhang et al. |
| 2017/0058339 A1 | 3/2017 | Chee |
| 2017/0058340 A1 | 3/2017 | Chee |
| 2017/0058345 A1 | 3/2017 | Chee |
| 2017/0067096 A1 | 3/2017 | Wassie et al. |
| 2017/0081489 A1 | 3/2017 | Rodriques et al. |
| 2017/0088881 A1 | 3/2017 | Chee |
| 2017/0089811 A1 | 3/2017 | Tillberg et al. |
| 2017/0101672 A1 | 4/2017 | Luo et al. |
| 2017/0166962 A1 | 6/2017 | van Eijk et al. |
| 2017/0220733 A1 | 8/2017 | Zhuang et al. |
| 2017/0233722 A1 | 8/2017 | Seelig et al. |
| 2017/0241911 A1 | 8/2017 | Rockel et al. |
| 2017/0242020 A1 | 8/2017 | Yamauchi et al. |
| 2017/0253918 A1 | 9/2017 | Kohman |
| 2017/0275669 A1 | 9/2017 | Weissleder et al. |
| 2017/0283860 A1 | 10/2017 | Kool et al. |
| 2017/0335297 A1 | 11/2017 | Ha et al. |
| 2017/0335410 A1 | 11/2017 | Driscoll et al. |
| 2017/0343545 A1 | 11/2017 | Hadrup et al. |
| 2017/0349940 A1 | 12/2017 | Morin et al. |
| 2018/0051322 A1 | 2/2018 | Church et al. |
| 2018/0052081 A1 | 2/2018 | Kohman |
| 2018/0057873 A1 | 3/2018 | Zhou et al. |
| 2018/0074039 A1 | 3/2018 | Soper et al. |
| 2018/0080876 A1 | 3/2018 | Rockel et al. |
| 2018/0094316 A1 | 4/2018 | Scott et al. |
| 2018/0095067 A1 | 4/2018 | Huff et al. |
| 2018/0104694 A1 | 4/2018 | Huff et al. |
| 2018/0105808 A1 | 4/2018 | Mikkelsen et al. |
| 2018/0112209 A1 | 4/2018 | Eshoo |
| 2018/0112261 A1 | 4/2018 | Van Driel et al. |
| 2018/0114316 A1 | 4/2018 | Lele et al. |
| 2018/0127817 A1 | 5/2018 | Borchert et al. |
| 2018/0156784 A1 | 6/2018 | Usmani et al. |
| 2018/0163265 A1 | 6/2018 | Zhang et al. |
| 2018/0179591 A1 | 6/2018 | van Eijk |
| 2018/0180601 A1 | 6/2018 | Pedersen et al. |
| 2018/0201925 A1 | 7/2018 | Steemers et al. |
| 2018/0201980 A1 | 7/2018 | Chee et al. |
| 2018/0208967 A1 | 7/2018 | Larman et al. |
| 2018/0216161 A1 | 8/2018 | Chen et al. |
| 2018/0216162 A1 | 8/2018 | Belhocine et al. |
| 2018/0217094 A1 | 8/2018 | Herr et al. |
| 2018/0237864 A1 | 8/2018 | Imler et al. |
| 2018/0245142 A1 | 8/2018 | So et al. |
| 2018/0247017 A1 | 8/2018 | van Eijk et al. |
| 2018/0251825 A1 | 9/2018 | Stoeckius |
| 2018/0251833 A1 | 9/2018 | Daugharthy et al. |
| 2018/0257075 A1 | 9/2018 | Yellen et al. |
| 2018/0282803 A1 | 10/2018 | Belgrader et al. |
| 2018/0291439 A1 | 10/2018 | van Eijk et al. |
| 2018/0305681 A1 | 10/2018 | Jovanovich et al. |
| 2018/0320226 A1 | 11/2018 | Church et al. |
| 2019/0017106 A1 | 1/2019 | Frisen et al. |
| 2019/0024153 A1 | 1/2019 | Frisen et al. |
| 2019/0024154 A1 | 1/2019 | Frisen et al. |
| 2019/0032121 A1 | 1/2019 | Daugharthy et al. |
| 2019/0055594 A1 | 2/2019 | Samusik et al. |
| 2019/0064173 A1 | 2/2019 | Bharadwaj et al. |
| 2019/0071796 A1 | 3/2019 | Parikh et al. |
| 2019/0085324 A1 | 3/2019 | Regev et al. |
| 2019/0112599 A1 | 4/2019 | Church et al. |
| 2019/0119735 A1 | 4/2019 | Deisseroth et al. |
| 2019/0135774 A1 | 5/2019 | Orbai |
| 2019/0155835 A1 | 5/2019 | Daugharthy et al. |
| 2019/0177718 A1 | 6/2019 | Church et al. |
| 2019/0177777 A1 | 6/2019 | Chee |
| 2019/0177778 A1 | 6/2019 | Chee |
| 2019/0177789 A1 | 6/2019 | Hindson et al. |
| 2019/0177800 A1 | 6/2019 | Boutet et al. |
| 2019/0194709 A1 | 6/2019 | Church et al. |
| 2019/0203275 A1 | 7/2019 | Friesen et al. |
| 2019/0218276 A1 | 7/2019 | Regev et al. |
| 2019/0218608 A1 | 7/2019 | Daugharthy et al. |
| 2019/0262831 A1 | 8/2019 | West et al. |
| 2019/0264268 A1 | 8/2019 | Frisen et al. |
| 2019/0264270 A1 | 8/2019 | Zhuang et al. |
| 2019/0271028 A1 | 9/2019 | Khafizov et al. |
| 2019/0271030 A1 | 9/2019 | Chee |
| 2019/0271031 A1 | 9/2019 | Chee |
| 2019/0276881 A1 | 9/2019 | Zhuang et al. |
| 2019/0300943 A1 | 10/2019 | Chee et al. |
| 2019/0300944 A1 | 10/2019 | Chee et al. |
| 2019/0300945 A1 | 10/2019 | Chee et al. |
| 2019/0309353 A1 | 10/2019 | Chee |
| 2019/0309354 A1 | 10/2019 | Chee |
| 2019/0309355 A1 | 10/2019 | Chee |
| 2019/0323071 A1 | 10/2019 | Chee |
| 2019/0330617 A1 | 10/2019 | Church et al. |
| 2019/0338353 A1 | 11/2019 | Belgrader et al. |
| 2019/0367982 A1 | 12/2019 | Belhocine et al. |
| 2019/0367997 A1 | 12/2019 | Bent et al. |
| 2020/0002763 A1 | 1/2020 | Belgrader et al. |
| 2020/0002764 A1 | 1/2020 | Belgrader et al. |
| 2020/0010891 A1 | 1/2020 | Beechem et al. |
| 2020/0024641 A1 | 1/2020 | Nolan et al. |
| 2020/0040382 A1 | 2/2020 | Beechem et al. |
| 2020/0048690 A1 | 2/2020 | Chee |
| 2020/0049599 A1 | 2/2020 | Alexander et al. |
| 2020/0061064 A1 | 2/2020 | Maciejewski et al. |
| 2020/0063195 A1 | 2/2020 | Chee |
| 2020/0063196 A1 | 2/2020 | Chee |
| 2020/0080136 A1 | 3/2020 | Zhang et al. |
| 2020/0109443 A1 | 4/2020 | Chee |
| 2020/0140920 A1 | 5/2020 | Pierce et al. |

(56) References Cited

U.S. PATENT DOCUMENTS

| | | |
|---|---|---|
| 2020/0140934 A1 | 5/2020 | Chee |
| 2020/0140935 A1 | 5/2020 | Chee |
| 2020/0208205 A1 | 7/2020 | Chee |
| 2020/0208206 A1 | 7/2020 | Chee |
| 2020/0224244 A1 | 7/2020 | Nilsson et al. |
| 2020/0224256 A1 | 7/2020 | Chee |
| 2020/0239946 A1 | 7/2020 | Dewal |
| 2020/0256867 A1 | 8/2020 | Hennek et al. |
| 2020/0277663 A1 | 9/2020 | Ramachandran Iyer et al. |
| 2020/0277664 A1 | 9/2020 | Frenz |
| 2020/0283852 A1 | 9/2020 | Oliphant et al. |
| 2020/0299757 A1 | 9/2020 | Chee et al. |
| 2020/0325531 A1 | 10/2020 | Chee |
| 2020/0332368 A1 | 10/2020 | Ferree et al. |
| 2020/0354774 A1 | 11/2020 | Church et al. |
| 2020/0370106 A1 | 11/2020 | Chee |
| 2020/0399687 A1 | 12/2020 | Frisen et al. |
| 2020/0407781 A1 | 12/2020 | Schnall-Levin et al. |
| 2021/0002713 A1 | 1/2021 | Chee et al. |
| 2021/0010068 A1 | 1/2021 | Chee et al. |
| 2021/0010070 A1 | 1/2021 | Schnall-Levin et al. |
| 2021/0017583 A1 | 1/2021 | Chee et al. |
| 2021/0017586 A1 | 1/2021 | Chee |
| 2021/0017587 A1 | 1/2021 | Cai et al. |
| 2021/0062249 A1 | 3/2021 | Chee |
| 2021/0123095 A1 | 4/2021 | Chee |
| 2021/0130883 A1 | 5/2021 | Chee et al. |
| 2021/0130884 A1 | 5/2021 | Chee et al. |
| 2021/0140982 A1 | 5/2021 | Uytingco |
| 2021/0172007 A1 | 6/2021 | Chee et al. |
| 2021/0189475 A1 | 6/2021 | Tentori et al. |
| 2021/0190770 A1 | 6/2021 | Delaney et al. |
| 2021/0198741 A1 | 7/2021 | Williams |
| 2021/0199660 A1 | 7/2021 | Williams et al. |
| 2021/0207202 A1 | 7/2021 | Chee |
| 2021/0214785 A1 | 7/2021 | Stoeckius |
| 2021/0222235 A1 | 7/2021 | Chee |
| 2021/0222241 A1 | 7/2021 | Bharadwaj |
| 2021/0222242 A1 | 7/2021 | Ramachandran Iyer |
| 2021/0222253 A1 | 7/2021 | Uytingco |
| 2021/0223227 A1 | 7/2021 | Stoeckius |
| 2021/0230681 A1 | 7/2021 | Patterson et al. |
| 2021/0230692 A1 | 7/2021 | Daugharthy et al. |
| 2021/0237022 A1 | 8/2021 | Bava |
| 2021/0238664 A1 | 8/2021 | Bava |
| 2021/0238675 A1 | 8/2021 | Bava |
| 2021/0238680 A1 | 8/2021 | Bava |
| 2021/0247316 A1 | 8/2021 | Bava |
| 2021/0255175 A1 | 8/2021 | Chee et al. |
| 2021/0262019 A1 | 8/2021 | Alvarado Martinez et al. |
| 2021/0269864 A1 | 9/2021 | Chee |
| 2021/0270822 A1 | 9/2021 | Chee |
| 2021/0285036 A1 | 9/2021 | Yin et al. |
| 2021/0285046 A1 | 9/2021 | Chell et al. |
| 2021/0292748 A1 | 9/2021 | Frisen et al. |
| 2021/0292822 A1 | 9/2021 | Frisen et al. |
| 2021/0317510 A1 | 10/2021 | Chee et al. |
| 2021/0317524 A1 | 10/2021 | Lucero et al. |
| 2021/0324457 A1 | 10/2021 | Ramachandran Iyer et al. |
| 2021/0332424 A1 | 10/2021 | Schnall-Levin |
| 2021/0332425 A1 | 10/2021 | Pfeiffer et al. |
| 2021/0348221 A1 | 11/2021 | Chell et al. |
| 2022/0002791 A1 | 1/2022 | Frisen et al. |
| 2022/0003755 A1 | 1/2022 | Chee |
| 2022/0010367 A1 | 1/2022 | Ramachandran Iyer et al. |
| 2022/0017951 A1 | 1/2022 | Ramachandran Iyer et al. |
| 2022/0025446 A1 | 1/2022 | Shah |
| 2022/0025447 A1 | 1/2022 | Tentori et al. |
| 2022/0033888 A1 | 2/2022 | Schnall-Levin et al. |
| 2022/0049293 A1 | 2/2022 | Frenz et al. |
| 2022/0049294 A1 | 2/2022 | Uytingco et al. |
| 2022/0064630 A1 | 3/2022 | Bent et al. |
| 2022/0081728 A1 | 3/2022 | Williams |
| 2022/0090058 A1 | 3/2022 | Frisen et al. |
| 2022/0090175 A1 | 3/2022 | Uytingco et al. |
| 2022/0090181 A1 | 3/2022 | Gallant et al. |
| 2022/0098576 A1 | 3/2022 | Dadhwal |
| 2022/0098661 A1 | 3/2022 | Chew et al. |
| 2022/0106632 A1 | 4/2022 | Galonska et al. |
| 2022/0106633 A1 | 4/2022 | Engblom et al. |
| 2022/0112486 A1 | 4/2022 | Ramachandran Iyer et al. |
| 2022/0112545 A1 | 4/2022 | Chee |
| 2022/0119869 A1 | 4/2022 | Ramachandran Iyer et al. |
| 2022/0127659 A1 | 4/2022 | Frisen et al. |
| 2022/0127666 A1 | 4/2022 | Katiraee et al. |
| 2022/0127672 A1 | 4/2022 | Stoeckius |
| 2022/0145361 A1 | 5/2022 | Frenz et al. |
| 2022/0154255 A1 | 5/2022 | Chee et al. |
| 2022/0170083 A1 | 6/2022 | Khaled et al. |
| 2022/0195422 A1 | 6/2022 | Gallant et al. |
| 2022/0195505 A1 | 6/2022 | Frisen et al. |
| 2022/0196644 A1 | 6/2022 | Chee |
| 2022/0213526 A1 | 7/2022 | Frisen et al. |
| 2022/0241780 A1 | 8/2022 | Tentori et al. |
| 2022/0267844 A1 | 8/2022 | Ramachandran Iyer et al. |
| 2022/0282329 A1 | 9/2022 | Chell et al. |
| 2022/0290217 A1 | 9/2022 | Frenz et al. |
| 2022/0290219 A1 | 9/2022 | Chee |
| 2022/0298560 A1 | 9/2022 | Frisen et al. |
| 2022/0325325 A1 | 10/2022 | Chee et al. |
| 2022/0326251 A1 | 10/2022 | Uytingco et al. |
| 2022/0333171 A1 | 10/2022 | Chee |
| 2022/0333192 A1 | 10/2022 | Uytingco |
| 2022/0333195 A1 | 10/2022 | Schnall-Levin et al. |
| 2022/0334031 A1 | 10/2022 | Delaney et al. |
| 2022/0348905 A1 | 11/2022 | Dadhwal |
| 2022/0348992 A1 | 11/2022 | Stoeckius et al. |
| 2022/0356464 A1 | 11/2022 | Kim et al. |
| 2022/0364163 A1 | 11/2022 | Stahl et al. |
| 2022/0389491 A1 | 12/2022 | Chee |
| 2022/0389504 A1 | 12/2022 | Chew et al. |
| 2022/0403455 A1 | 12/2022 | Ramachandran Iyer et al. |
| 2022/0404245 A1 | 12/2022 | Chell et al. |
| 2023/0002812 A1 | 1/2023 | Stoeckius et al. |
| 2023/0014008 A1 | 1/2023 | Shastry |
| 2023/0033960 A1 | 2/2023 | Gallant et al. |
| 2023/0034039 A1 | 2/2023 | Shahjamali |
| 2023/0034216 A1 | 2/2023 | Bava |
| 2023/0040363 A1 | 2/2023 | Chee |
| 2023/0042088 A1 | 2/2023 | Chee |
| 2023/0042817 A1 | 2/2023 | Mignardi |
| 2023/0047782 A1 | 2/2023 | Tentori et al. |
| 2023/0056549 A1 | 2/2023 | Dadhwal |
| 2023/0064372 A1 | 3/2023 | Chell et al. |
| 2023/0069046 A1 | 3/2023 | Chew et al. |
| 2023/0077364 A1 | 3/2023 | Patterson et al. |
| 2023/0080543 A1 | 3/2023 | Katiraee et al. |
| 2023/0081381 A1 | 3/2023 | Chew et al. |
| 2023/0100497 A1 | 3/2023 | Frisen et al. |
| 2023/0107023 A1 | 4/2023 | Chee |
| 2023/0111225 A1 | 4/2023 | Chew et al. |
| 2023/0113230 A1 | 4/2023 | Kim et al. |
| 2023/0135010 A1 | 5/2023 | Tentori et al. |
| 2023/0143569 A1 | 5/2023 | Iyer et al. |
| 2023/0145575 A1 | 5/2023 | Gallant et al. |
| 2023/0151412 A1 | 5/2023 | Chee |
| 2023/0159994 A1 | 5/2023 | Chee |
| 2023/0159995 A1 | 5/2023 | Iyer et al. |
| 2023/0160008 A1 | 5/2023 | Chell et al. |

FOREIGN PATENT DOCUMENTS

| | | |
|---|---|---|
| CN | 1425133 | 6/2003 |
| CN | 1537953 | 10/2004 |
| CN | 1680604 | 10/2005 |
| CN | 1749752 | 3/2006 |
| CN | 1898398 | 1/2007 |
| CN | 1981188 | 6/2007 |
| CN | 101142325 | 3/2008 |
| CN | 101221182 | 7/2008 |
| CN | 101522915 | 9/2009 |
| CN | 102851369 | 1/2013 |
| CN | 104513785 | 4/2015 |
| EP | 0901631 | 3/1999 |

(56) References Cited

FOREIGN PATENT DOCUMENTS

| | | |
|---|---|---|
| EP | 0961110 | 12/1999 |
| EP | 1782737 | 5/2007 |
| EP | 1878502 | 1/2008 |
| EP | 1910562 | 4/2008 |
| EP | 1923471 | 5/2008 |
| EP | 1929039 | 6/2008 |
| EP | 1966393 | 9/2008 |
| EP | 2002017 | 12/2008 |
| EP | 2292788 | 3/2011 |
| EP | 2302070 | 3/2011 |
| EP | 2350648 | 8/2011 |
| EP | 2363504 | 9/2011 |
| EP | 2580351 | 4/2013 |
| EP | 2789696 | 10/2014 |
| EP | 2881465 | 6/2015 |
| EP | 2963127 | 1/2016 |
| EP | 3013984 | 5/2016 |
| EP | 3045544 | 7/2016 |
| EP | 3239304 | 11/2017 |
| EP | 3541956 | 9/2019 |
| EP | 3425053 | 8/2020 |
| GB | 2520765 | 6/2015 |
| JP | 2007-014297 | 1/2007 |
| JP | 2007-074967 | 3/2007 |
| JP | 2009-036694 | 2/2009 |
| JP | 2011-182702 | 9/2011 |
| JP | 2013-544498 | 12/2013 |
| JP | 2014-217381 | 11/2014 |
| KR | 10-2009-0000812 | 1/2009 |
| KR | 10-2009-0081260 | 7/2009 |
| RU | 2145635 | 2/2000 |
| RU | 2270254 | 2/2006 |
| RU | 2410439 C1 | 1/2011 |
| WO | WO 1989/010977 | 11/1989 |
| WO | WO 1991/006678 | 5/1991 |
| WO | WO 1993/004199 | 3/1993 |
| WO | WO 1995/023875 | 9/1995 |
| WO | WO 1995/025116 | 9/1995 |
| WO | WO 1995/035505 | 12/1995 |
| WO | WO 1997/031256 | 8/1997 |
| WO | WO 1998/044151 | 10/1998 |
| WO | WO 1999/032654 | 7/1999 |
| WO | WO 1999/044062 | 9/1999 |
| WO | WO 1999/044063 | 9/1999 |
| WO | WO 1999/063385 | 12/1999 |
| WO | WO 2000/017390 | 3/2000 |
| WO | WO 2000/018957 | 4/2000 |
| WO | WO 2000/024940 | 5/2000 |
| WO | WO 2001/006012 | 1/2001 |
| WO | WO 2001/007915 | 2/2001 |
| WO | WO 2001/009363 | 2/2001 |
| WO | WO 2001/012862 | 2/2001 |
| WO | WO 2001/042796 | 6/2001 |
| WO | WO 2001/046402 | 6/2001 |
| WO | WO 2001/059161 | 8/2001 |
| WO | WO 2001/090415 | 11/2001 |
| WO | WO 2001/096608 | 12/2001 |
| WO | WO 2002/024952 | 3/2002 |
| WO | WO 2002/040874 | 5/2002 |
| WO | WO 2002/059355 | 8/2002 |
| WO | WO 2002/059364 | 8/2002 |
| WO | WO 2002/077283 | 10/2002 |
| WO | WO 2002/088396 | 11/2002 |
| WO | WO 2003/002979 | 1/2003 |
| WO | WO 2003/003810 | 1/2003 |
| WO | WO 2003/008538 | 1/2003 |
| WO | WO 2003/010176 | 2/2003 |
| WO | WO 2003/102233 | 12/2003 |
| WO | WO 2003/106973 | 12/2003 |
| WO | WO 2004/015080 | 2/2004 |
| WO | WO 2004/028955 | 4/2004 |
| WO | WO 2004/055159 | 7/2004 |
| WO | WO 2004/067759 | 8/2004 |
| WO | WO 2004/081225 | 9/2004 |
| WO | WO 2004/108268 | 12/2004 |
| WO | WO 2005/007814 | 1/2005 |
| WO | WO 2005/010145 | 2/2005 |
| WO | WO 2005/026387 | 3/2005 |
| WO | WO 2005/042759 | 5/2005 |
| WO | WO 2005/065814 | 7/2005 |
| WO | WO 2005/067648 | 7/2005 |
| WO | WO 2005/113804 | 12/2005 |
| WO | WO 2006/020515 | 2/2006 |
| WO | WO 2006/056861 | 6/2006 |
| WO | WO 2006/064199 | 6/2006 |
| WO | WO 2006/065597 | 6/2006 |
| WO | WO 2006/074351 | 7/2006 |
| WO | WO 2006/084130 | 8/2006 |
| WO | WO 2006/117541 | 11/2006 |
| WO | WO 2006/124771 | 11/2006 |
| WO | WO 2006/137733 | 12/2006 |
| WO | WO 2007/000669 | 1/2007 |
| WO | WO 2007/010251 | 1/2007 |
| WO | WO 2007/030373 | 3/2007 |
| WO | WO 2007/037678 | 4/2007 |
| WO | WO 2007/041689 | 4/2007 |
| WO | WO 2007/060599 | 5/2007 |
| WO | WO 2007/073165 | 6/2007 |
| WO | WO 2007/073171 | 6/2007 |
| WO | WO 2007/073271 | 6/2007 |
| WO | WO 2007/076128 | 7/2007 |
| WO | WO 2007/076726 | 7/2007 |
| WO | WO 2007/114693 | 10/2007 |
| WO | WO 2007/120241 | 10/2007 |
| WO | WO 2007/139766 | 12/2007 |
| WO | WO 2007/145612 | 12/2007 |
| WO | WO 2008/022332 | 2/2008 |
| WO | WO 2008/069906 | 6/2008 |
| WO | WO 2008/157801 | 12/2008 |
| WO | WO 2009/032167 | 3/2009 |
| WO | WO 2009/036525 | 3/2009 |
| WO | WO 2009/152928 | 12/2009 |
| WO | WO 2009/156725 | 12/2009 |
| WO | WO 2010/019826 | 2/2010 |
| WO | WO 2010/027870 | 3/2010 |
| WO | WO 2010/053587 | 5/2010 |
| WO | WO 2010/126614 | 11/2010 |
| WO | WO 2010/127186 | 11/2010 |
| WO | WO 2011/008502 | 1/2011 |
| WO | WO 2011/014879 | 2/2011 |
| WO | WO 2011/062933 | 5/2011 |
| WO | WO 2011/068088 | 6/2011 |
| WO | WO 2011/071943 | 6/2011 |
| WO | WO 2011/094669 | 8/2011 |
| WO | WO 2011/102903 | 8/2011 |
| WO | WO 2011/127006 | 10/2011 |
| WO | WO 2011/127099 | 10/2011 |
| WO | WO 2011/143583 | 11/2011 |
| WO | WO 2011/155833 | 12/2011 |
| WO | WO 2012/022975 | 2/2012 |
| WO | WO 2012/048341 | 4/2012 |
| WO | WO 2012/049316 | 4/2012 |
| WO | WO 2012/058096 | 5/2012 |
| WO | WO 2012/071428 | 5/2012 |
| WO | WO 2012/083225 | 6/2012 |
| WO | WO 2012/129242 | 9/2012 |
| WO | WO 2012/139110 | 10/2012 |
| WO | WO 2012/140224 | 10/2012 |
| WO | WO 2012/142213 | 10/2012 |
| WO | WO 2012/148477 | 11/2012 |
| WO | WO 2012/159089 | 11/2012 |
| WO | WO 2012/168003 | 12/2012 |
| WO | WO 2013/033271 | 3/2013 |
| WO | WO 2013/090390 | 6/2013 |
| WO | WO 2013/123442 | 8/2013 |
| WO | WO 2013/131962 | 9/2013 |
| WO | WO 2013/138510 | 9/2013 |
| WO | WO 2013/142389 | 9/2013 |
| WO | WO 2013/150082 | 10/2013 |
| WO | WO 2013/150083 | 10/2013 |
| WO | WO 2013/155119 | 10/2013 |
| WO | WO 2013/158936 | 10/2013 |
| WO | WO 2014/044724 | 3/2014 |
| WO | WO 2014/060483 | 4/2014 |

(56) References Cited

FOREIGN PATENT DOCUMENTS

| | | |
|---|---|---|
| WO | WO 2014/085725 | 6/2014 |
| WO | WO 2014/128129 | 8/2014 |
| WO | WO 2014/130576 | 8/2014 |
| WO | WO 2014/142841 | 9/2014 |
| WO | WO 2014/144713 | 9/2014 |
| WO | WO 2014/152397 | 9/2014 |
| WO | WO 2014/200767 | 12/2014 |
| WO | WO 2014/210223 | 12/2014 |
| WO | WO 2014/210225 | 12/2014 |
| WO | WO 2014/210233 | 12/2014 |
| WO | WO 2015/031691 | 3/2015 |
| WO | WO 2015/069374 | 5/2015 |
| WO | WO 2015/085275 | 6/2015 |
| WO | WO 2015/117163 | 8/2015 |
| WO | WO 2015/128272 | 9/2015 |
| WO | WO 2015/161173 | 10/2015 |
| WO | WO 2016/040476 | 3/2016 |
| WO | WO 2016/044313 | 3/2016 |
| WO | WO 2016/057552 | 4/2016 |
| WO | WO 2016/077763 | 5/2016 |
| WO | WO 2016/126871 | 8/2016 |
| WO | WO 2016/138496 | 9/2016 |
| WO | WO 2016/138500 | 9/2016 |
| WO | WO 2016/162309 | 10/2016 |
| WO | WO 2016/166128 | 10/2016 |
| WO | WO 2016/168825 | 10/2016 |
| WO | WO 2016/172362 | 10/2016 |
| WO | WO 2017/015097 | 1/2017 |
| WO | WO 2017/015099 | 1/2017 |
| WO | WO 2017/019456 | 2/2017 |
| WO | WO 2017/019481 | 2/2017 |
| WO | WO 2017/027367 | 2/2017 |
| WO | WO 2017/027368 | 2/2017 |
| WO | WO 2017/048871 | 3/2017 |
| WO | WO 2017/075265 | 5/2017 |
| WO | WO 2017/075293 | 5/2017 |
| WO | WO 2017/112957 | 6/2017 |
| WO | WO 2017/096158 | 7/2017 |
| WO | WO 2017/124101 | 7/2017 |
| WO | WO 2017/144338 | 8/2017 |
| WO | WO 2017/147483 | 8/2017 |
| WO | WO 2017/156336 | 9/2017 |
| WO | WO 2017/177308 | 10/2017 |
| WO | WO 2017/184984 | 10/2017 |
| WO | WO 2017/192633 | 11/2017 |
| WO | WO 2017/222453 | 12/2017 |
| WO | WO 2018/022809 | 2/2018 |
| WO | WO 2018/023068 | 2/2018 |
| WO | WO 2018/045181 | 3/2018 |
| WO | WO 2018/045186 | 3/2018 |
| WO | WO 2018/057999 | 3/2018 |
| WO | WO 2018/064640 | 4/2018 |
| WO | WO 2018/075436 | 4/2018 |
| WO | WO 2018/075693 | 4/2018 |
| WO | WO 2018/085599 | 5/2018 |
| WO | WO 2018/091676 | 5/2018 |
| WO | WO 2018/102577 | 6/2018 |
| WO | WO 2018/107054 | 6/2018 |
| WO | WO 2018/136397 | 7/2018 |
| WO | WO 2018/136856 | 7/2018 |
| WO | WO 2018/144582 | 8/2018 |
| WO | WO 2018/148471 | 8/2018 |
| WO | WO 2020/053655 | 3/2020 |
| WO | WO 2020/061064 | 3/2020 |
| WO | WO 2020/061066 | 3/2020 |
| WO | WO 2020/061108 | 3/2020 |
| WO | WO 2020/076979 | 4/2020 |
| WO | WO 2020/123305 | 6/2020 |
| WO | WO 2020/123309 | 6/2020 |
| WO | WO 2020/123311 | 6/2020 |
| WO | WO 2020/123316 | 6/2020 |
| WO | WO 2020/123317 | 6/2020 |
| WO | WO 2020/123318 | 6/2020 |
| WO | WO 2020/123319 | 6/2020 |
| WO | WO 2016/126882 | 8/2020 |
| WO | WO 2020/167862 | 8/2020 |
| WO | WO 2020/176788 | 9/2020 |
| WO | WO 2020/176882 | 9/2020 |
| WO | WO 2020/190509 | 9/2020 |
| WO | WO 2020/198071 | 10/2020 |
| WO | WO 2020/219901 | 10/2020 |
| WO | WO 2021/091611 | 5/2021 |
| WO | WO 2021/092433 | 5/2021 |
| WO | WO 2021/097255 | 5/2021 |
| WO | WO 2021/133842 | 7/2021 |
| WO | WO 2021/133849 | 7/2021 |
| WO | WO 2021/142233 | 7/2021 |
| WO | WO 2021/168261 | 8/2021 |
| WO | WO 2021/168278 | 8/2021 |
| WO | WO 2021/207610 | 10/2021 |
| WO | WO 2021/216708 | 10/2021 |
| WO | WO 2021/225900 | 11/2021 |
| WO | WO 2021/236625 | 11/2021 |
| WO | WO 2021/236929 | 11/2021 |
| WO | WO 2021/237056 | 11/2021 |
| WO | WO 2021/237087 | 11/2021 |
| WO | WO 2021/242834 | 12/2021 |
| WO | WO 2021/247543 | 12/2021 |
| WO | WO 2021/247568 | 12/2021 |
| WO | WO 2021/252499 | 12/2021 |
| WO | WO 2021/252576 | 12/2021 |
| WO | WO 2021/252591 | 12/2021 |
| WO | WO 2021/263111 | 12/2021 |
| WO | WO 2022/025965 | 2/2022 |
| WO | WO 2022/060798 | 3/2022 |
| WO | WO 2022/060953 | 3/2022 |
| WO | WO 2022/087273 | 4/2022 |
| WO | WO 2022/098810 | 5/2022 |
| WO | WO 2022/099037 | 5/2022 |
| WO | WO 2022/103712 | 5/2022 |
| WO | WO 2022/109181 | 5/2022 |
| WO | WO 2022/140028 | 6/2022 |
| WO | WO 2022/147005 | 7/2022 |
| WO | WO 2022/147296 | 7/2022 |
| WO | WO 2022/164615 | 8/2022 |
| WO | WO 2022/178267 | 8/2022 |
| WO | WO 2022/198068 | 9/2022 |
| WO | WO 2022/221425 | 10/2022 |
| WO | WO 2022/226057 | 10/2022 |
| WO | WO 2022/236054 | 11/2022 |
| WO | WO 2022/256503 | 12/2022 |
| WO | WO 2022/271820 | 12/2022 |
| WO | WO 2023/287765 | 1/2023 |
| WO | WO 2023/018799 | 2/2023 |
| WO | WO 2023/034489 | 3/2023 |
| WO | WO 2023/086880 | 5/2023 |

OTHER PUBLICATIONS

U.S. Appl. No. 17/707,189, filed Mar. 29, 2022, Chell et al.
U.S. Appl. No. 60/416,118, filed Oct. 3, 2002, Fan et al.
U.S. Appl. No. 61/839,313, filed Jun. 25, 2013, Chee et al.
U.S. Appl. No. 61/839,320, filed Jun. 25, 2013, Chee et al.
U.S. Appl. No. 61/902,105, filed Nov. 8, 2013, Kozlov et al.
U.S. Appl. No. 62/839,575, filed Apr. 26, 2019, Bent et al.
[No Author Listed], "HuSNP Mapping Assay User's Manual," Affymetrix Part No. 90094 (Affymetrix, Santa Clara, Calif,), GeneChip, 2000, 104 pages.
[No Author Listed], "Microarray technologies have excellent possibilities in genomics-related researches," Science Tools From Amersham Pharmacia Biotech, 1998, 3(4): 8 pages (with English Translation).
[No Author Listed], "Proseek® Multiplex 96x96 User Manual," Olink Proteomics, Olink Bioscience, Uppsala, Sweden, 2017, 20 pages.
Abaan et al., "The exomes of the NCI-60 panel: a genomic resource for cancer biology and systems pharmacology," Cancer Res., Jul. 2013, 73(14):4372-82.
Adamson et al., "A Multiplexed Single-Cell CRISPR Screening Platform Enables Systematic Dissection of the Unfolded Protein Response," Cell, Dec. 2016, 167(7):1867-1882.e21.
Adessi et al., "Solid phase DNA amplification: characterisation of primer attachment and amplification mechanisms," Nucl. Acids Res., Oct. 2000, 28(20):E87, 8 pages.

(56) References Cited

OTHER PUBLICATIONS

Adiconis et al., "Comparative analysis of RNA sequencing methods for degraded or low-input samples," Nat Methods, Jul. 2013, 10(7):623-9.

Affymetrix, "GeneChip Human Genome U133 Set," retrieved from the Internet: on the World Wide Web at affymetrix.com/support/technical/datasheets/hgu133_datasheet.pdf, retrieved on Feb. 26, 2003.

Affymetrix, "Human Genome U95Av2," Internet Citation, retrieved from the internet: on the World Wide Web affymetrix.com, retrieved on Oct. 2, 2002.

Agasti et al., "Photocleavable DNA Barcode-Antibody Conjugates Allow Sensitive and Multiplexed Protein Analysis in Single Cells," Journal of the American Chemical Society, Oct. 23, 2012, 134(45):18499-18502.

Agbavwe et al., "Efficiency, error and yield in light-directed maskless synthesis of DNA microarrays," Journal of Nanobiotechnology, Dec. 2011, 9:57, 17 pages.

Agilent.com [online], "The First Comprehensive Methylation Discovery System," Dec. 2015, retrieved on Jan. 21, 2022, retrieved from URL<https://www.agilent.com/cs/library/datasheets/Public/SureselectXTHumanMethyl-Seq-5990-9856EN.pdf>, 2 pages.

Ahern et al., "Biochemical, Reagents Kits Offer Scientists Good Return on Investment," The Scientist, 1995, 9(15):20, 7 pages.

Ahern, "Biochemical, Reagents Kits Offer Scientists Good Return on Investment," The Scientist, Jul. 1995, 9(15):20, 7 pages.

Ahlfen et al., "Determinants of RNA quality from FFPE samples," PLoS One, Dec. 2007, 2(12):e1261, 7 pages.

Ahmed et al., "Hydrogel: Preparation, characterization, and applications: A review," J Adv Res., Mar. 2015, 6(2):105-21.

Akeroyd, "Click chemistry for the preparation of advanced macromolecular architectures," Stellenbosch University, PhD Dissertation, Mar. 2010, 138 pages.

Albretsen et al., "Applications of magnetic beads with covalently attached oligonucleotides in hybridization: Isolation and detection of specific measles virus mRNA from a crude cell lysate", Anal. Biochem. 189: 40-50, 1990.

Albretsen et al., "Optimal conditions for hybridization with oligonucleotides: a study with myc-oncogene DNA probes," Anal Biochem., Apr. 1988, 170(1):193-202.

Ali et al., "Patterns of Immune Infiltration in Breast Cancer and Their Clinical Implications: A Gene-Expression-Based Retrospective Study," PLoS Med., Dec. 2016, 13(12):e1002194, 24 pages.

Allawi and SantaLucia, "Thermodynamics and NMR of Internal G·T Mismatches in DNA," Biochemistry, 1996, 36:10581-10594.

Altaras et al., "Production and formulation of adenovirus vectors," Adv Biochem Eng Biotechnol., Nov. 2005, 99:193-260.

Altschul et al., "Basic local alignment search tool," J. Mol. Biol., Oct. 5, 1990, 215(3):403-410.

Amidzadeh et al., "Assessment of different permeabilization methods of minimizing damage to the adherent cells for detection of intracellular RNA by flow cytometry," Avicenna J Med Biotechnol., Jan. 2014, 6(1):38-46.

Anderson et al., "Microarrayed Compound Screening to Identify Activators and Inhibitors of AMP-Activated Protein Kinase," J. of Biomolecular Screening, 2004, 9:112.

Andersson et al., "Analysis of protein expression in cell microarrays: a tool for antibody-based proteomics.," J Histochem Cytochem., 4(12): 1413-1423, 2006.

Andresen et al., "Deciphering the Antibodyome—Peptide Arrays for Serum Antibody Biomarker Diagnostics," Current Proteomics, 6(1), 1-12, 2009.

Andresen et al., "Helicase-dependent amplification: use in OnChip amplification and potential for point-of-care diagnostics," Expert Rev Mol Diagn., Oct. 2009, 9(7):645-650.

Angenendt et al., "Cell-free Protein expression and functional assay in a nanowell chip format," Analytical Chemistry, 2004, 76(7):1844-49.

Angenendt et al., "Generation of High Density Protein Microarrays by Cell-free in Situ Expression of Unpurified PCR Products," Molecular and Cellular Proteomics, (2006) Ch. 5.9, pp. 1658-1666.

Appella, "Non-natural nucleic acids for synthetic biology," Current Opinion in Chemical Biology, Dec. 2009, 13(5-6): 687-696.

Archer et al., "Selective and flexible depletion of problematic sequences from RNA-seq libraries at the cDNA stage," BMC Genomics, May 2014, 15(1):401, 9 pages.

Armani et al., "2D-PCR: a method of mapping DNA in tissue sections," Lab on a Chip, 2009, 9(24):3526-34.

Arslan et al., "Engineering of a superhelicase through conformational control (Supplementary Materials)," Science, Apr. 17, 2015, 348(6232):344-347 18 pages.

Arslan et al., "Engineering of a superhelicase through conformational control," Science, Apr. 17, 2015, 348(6232):344-347.

Asp et al., "Spatial detection of fetal marker genes expressed at low level in adult human heart tissue", Scientific Reports, 7: 12941, 10 pages, 2017.

Atkinson and Wells, "An Updated Protocol for High Throughput Plant Tissue Sectioning.", Front Plant Sci, 8: 1721, 2017.

Atkinson, Overview of Translation: Lecture Manuscript, U of Texas (2000) DD. 6.1-6.8.

Azioune et al., "Simple and rapid process for single cell micropatterning," Lab Chip, Jun. 2009, 9(11):1640-1642.

Bains et al, "A Novel Method for Nucleic Acid Sequence Determination", Journal of Theoretical Biology, 1988, 135(3), 303-7.

Baird et al., "Rapid SNP Discovery and Genetic Mapping Using Sequenced RAD markers," PLOS One, 2008, 3(10):e3376.

Bajar et al., "A Guide to Fluorescent Protein FRET Pairs," Sensors (Basel), Sep. 2016, 16(9):1488, 24 pages.

Balakrishnan et al., "Flap endonuclease 1," Annu Rev Biochem., Jun. 2013, 82:119-138.

Baner et al., "Signal amplification of padlock probes by rolling circle replication," Nucleic Acids Res., 1998, 26(22):5073-5078.

Banerjee et al., "Viral glycoproteins: biological role and application in diagnosis," Virusdisease, Mar. 2016, 27(1):1-11.

Barbie et al., "Systematic RNA interference reveals that oncogenic KRAS-driven cancers require TBK1," Nature, Nov. 2009, 462(7269):108-12.

Barnes, "PCR amplification of up to 35-kb DNA with high fidelity and high yield from lambda bacteriophage templates.," Proc. Natl. Acad. Sci USA, 91: 2216-2220, 1994.

Baugh et al., "Quantitative analysis of mRNA amplification by in vitro transcription," Nucleic Acids Res., 2001, 29:5:e29.

Beattie et al., "Advances in genosensor research," Clin Chem., May 1995, 41(5):700-6.

Bechara et al., "Cell-penetrating peptides: 20 years later, where do we stand?," FEBS Lett., Jun. 2013, 587(12):1693-702.

Beier et al., "Versatile derivatisation of solid support media for covalent bonding on DNA-microchips," Nucleic Acids Res., May 1999, 27(9):1970-7.

Bell, "A Simple Way to Treat PCR Products Prior to Sequencing Using ExoSAP-IT," Biotechniques, 2008, vol. 44, No. 6.

Bentley et al, "Accurate whole human genome sequencing using reversible terminator chemistry", Nature, 2008, 456:53-59.

Berger et al., "Universal bases for hybridization, replication and chain termination," Nucleic Acid Res., Aug. 2000, 28(15):2911-2914.

Bielas et al., "Human cancers express a mutator phenotype," Proc. Natl. Acad. Sci. USA, 2006, 103(48): 18238-18242.

Bielas et al., "Quantification of random genomic mutations," Nat. Methods, 2005, 2(4):285-290.

Biol.wwu.edu [online], "Principles of Di-Base Sequencing and the Advantages of Color Space Analysis in the SOLiD System," 2008, retrieved on Mar. 11, 2022, retrieved from URL<https://biol.wwu.edu//young/470/stuff/abi-solid.pdf>, 4 pages.

Birney, et al, "Identification and analysis of functional elements in 1% of the human genome by the ENCODE pilot project," Nature, 2007, 447:799-816.

Blair et al., "Microarray temperature optimization using hybridization kinetics," Methods Mol Biol., 2009, 529:171-96.

Blanchard et al., "High-density oligonucleotide arrays," Biosensors & Bioelectronics, 1996, 11(6-7):687-690.

(56) References Cited

OTHER PUBLICATIONS

Blanco et al., "A practical approach to FRET-based PNA fluorescence in situ hybridization," Methods, Dec. 2010, 52(4):343-51.
Blandini et al., "Animal models of Parkinson's disease," FEBS J., Apr. 2012, 279(7):1156-66.
Blokzijl et al., "Profiling protein expression and interactions: proximity ligation as a tool for personalized medicine," J Intern. Med., 2010, 268:232-245.
Blow, "Tissue Issues," Nature, 448(23), 959-962, 2007.
Boeke et al., "Transcription and reverse transcription of retrotransposons," Annu Rev Microbiol, 1989, 43:403-34.
Bolotin et al., "MiXCR: software for comprehensive adaptive immunity profiling," Nat Methods., May 2015, 12(5):380-1.
Bonfield et al., "The application of numerical estimates of base calling accuracy to DNA sequencing projects," Nucleic Acids Research, 1995, 23(8):1406-1410.
Bootman et al., "Loading fluorescent Ca2+ indicators into living cells," Cold Spring Harb Protoc., Feb. 2013, 2013(2):122-5.
Bos et al., "In Vitro Evaluation of DNA-DNA Hybridization as a Two-Step Approach in Radioimmunotherapy of Cancer," Cancer Res., Jul. 1, 1994, 54(13):3479-3486.
Boulé et al., "Terminal deoxynucleotidyl transferase indiscriminately incorporates ribonucleotides and deoxyribonucleotides," J Biol Chem., Aug. 2001, 276(33):31388-93.
Boulgakov et al., "From Space to Sequence and Back Again: Iterative DNA Proximity Ligation and its Applications to DNA-Based Imaging", bioRxiv, 24 pages, 2018.
Boutros et al., "The art and design of genetic screens: RNA interference," Nat Rev Genet., Jul. 2008, 9(7):554-66.
Bowtell, "The genesis and evolution of high-grade serous ovarian cancer," Nat. Rev. Cancer, 2010, (11 ):803-808 Abstract.
Brandon et al., "Mitochondrial mutations in cancer," Oncogene, 2006, 25(34):4647-4662.
Brenner et al, "In vitro cloning of complex mixtures of DNA on microbeads: physical separation of differentially expressed cDNAs," Proc. Natl. Acad. Sci. USA, 2000, 97, 1665-1670.
Brenner et al., "Gene expression analysis by massively parallel signature sequencing (MPSS) on microbead arrays", Nat. Biotech, 18: 630-634, 2000.
Brockman et al., "Quality scores and SNP detection in sequencing-by-synthesis systems," Methods, 2008, 18:763-770.
Brow, "35—The Cleavase I enzyme for mutation and polymorphism scanning," PCR Applications Protocols for Functional Genomics, 1999, pp. 537-550.
Brown et al., "Retroviral integration: structure of the initial covalent product and its precursor, and a role for the viral IN protein," Proc Natl Acad Sci USA, Apr. 1989, 86(8):2525-9.
Buenrostro et al., "Transposition of native chromatin for multimodal regulatory analysis and personal epigenomics," Nat Methods, Dec. 2013, 10(12):1213-1218.
Bugada et al., "Inflammation-based scores: a new method for patient-targeted strategies and improved perioperative outcome in cancer patients," Biomed Res Int., 2014, 2014:142425, 12 pages.
Bullard et al., "Direct comparison of nick-joining activity of the nucleic acid ligases from bacteriophage T4," Biochem. J. 2006, 398:135-144.
Burgess, "A space for transcriptomics", Nature Reviews Genetics | Published online Jul. 15, 2016; doi:10.1038/nrg.2016.94.
Burgess, "Finding structure in gene expression", Nature Reviews Genetics | Published online Apr. 13, 2018; doi:10.1038/nrg.2018.19.
Burns et al., "Well-less, gel-permeation formats for ultra-HTS," DDT, 2001, 6(12):S40-S47.
Burton et al., "Coverslip Mounted-Immersion Cycled in Situ RT-PCR for the Localization of mRNA in Tissue Sections," Biotechniques, 1998, 24; pp. 92-100.
Cabrera-Fuentes et al., "RNase1 prevents the damaging interplay between extracellular RNA and tumour necrosis factor-α in cardiac ischaemia/reperfusion injury," Thromb Haemost., Dec. 2014, 112(6):1110-9.
Caliari et al., "A practical guide to hydrogels for cell culture," Nat Methods., Apr. 2016, 13(5):405-14.
Calvert, "Materials science. Printing cells," Science, Oct. 2007, 318(5848):208-209.
Camacho et al., "Small mammalian animal models of heart disease," Am. J Cardiovasc. Dis., Sep. 2016, 6(3):70-80.
Cancernetwork.com, [online], Allison et al., "Heterogeneity and cancer," Oncology (Williston Park), Sep. 15, 2014, 28(9):772-8, via Internet Archive: Wayback Machine URL<The Wayback Machine— https://web.archive.org/web/20190129000357/http://www.cancernetwork.com:80/oncology-journal/heterogeneity-and-cancer>, retrieved on Oct. 21, 2021, URL<http://www.cancernetwork.com:80/oncology-journal/heterogeneity-and-cancer>, 3 pages.
Cardona et al., "TrakEM2 0.9a User Manual," Sep. 8, 2011, retrieved on Jul. 29, 2022, retrieved from URL <https://www.ini.uzh.ch/~acardona/trakem2_manual.html>, 38 pages.
Carlson et al., "Function and Structure of a Prokaryotic Formylglycine-generating Enzyme," J. of Biological Chemistry, 2008, 283(29):20117-125.
Carter et al., "Stabilization of an optical microscope to 0.1 nm in three dimensions," Applied Optics, 2007, 46:421-427.
Carter, "Porphyrin-phospholipid liposomes premeablizied by near-infrared light," Nat. Commun., Apr. 2014, 5:3546, p. 1-11.
Cerritelli et al., "Ribonuclease H: the enzymes in eukaryotes," FEBS Journal, Mar. 2009, 276(6):1494-505.
Cerutti et al., "Generation of sequence-specific, high affinity anti-DNA antibodies," Journal of Biological Chemistry, 2001, 276(16):12769-12773.
Cha et al., "Specificity, Efficiency and Fidelity of PCR," Genome Res., 1993, 3:518-29.
Chandra et al., "Cell-free synthesis-based protein microarrays and their applications," Proteomics, 2009, 5(6):717-30.
Chatterjee et al., "Protein Microarray on-Demand: A Novel Protein Microarray System," PLos One, 2008, 3(9):e3265.
Chatterjee, et al., "Mitochondrial DNA mutations in human cancer. Oncogene," 2006, 25(34):4663-4674.
Chen et al., "A Homogeneous, Ligase-mediated DNA diagnostic test," Genome research, 1998, 8(5):549-556.
Chen et al., "DNA hybridization detection in a microfluidic Channel using two fluorescently labelled nucleic acid probes," Biosensors and Bioelectronics, 2008, 23:1878-1882.
Chen et al., "ExpansionMicroscopy," 2015, Science. 347(6221):543-548.
Chen et al., "Fusion protein linkers: Property, design and functionality," Advanced Drug Delivery Reviews, Oct. 15, 2013, 65(10):1357-1369, 32 pages.
Chen et al., "Geometric control of cell life and death," Science, May 1997, 276(5317):1425-1428.
Chen et al., "Gray-scale photolithography using microfluidic photomasks," PNAS, Feb. 2003, 100(4):1499-1504.
Chen et al., "High PLTP activity is associated with depressed left ventricular systolic function," Atherosclerosis, Jun. 2013, 228(2):438-42.
Chen et al., "Nanoscale imaging of RNA with expansion microscopy," Nat Methods, Aug. 2016, 13(8):679-84.
Chen et al., "Parallel single nucleotide polymorphism genotyping by surface invasive cleavage with universal detection," Anal Chem., Apr. 2005, 77(8):2400-5.
Chen et al., "RNA imaging. Spatially resolved, highly multiplexed RNA profiling in single cells," Science, Apr. 2015, 348(6233):aaa6090, 21 pages.
Chen et al., "Spatially resolved, highly multiplexed RNA profiling in single cells", Science 348(6233), 36 pages, 2015.
Chen et al., "ATAC-see reveals the accessible genome by transposase-mediated imaging and sequencing," Nature Methods, Dec. 2016, 13(12):1013-1024.
Cheng et al., "Sensitive Detection of Small Molecules by Competitive Immunomagnetic-Proximity Ligation Assay," Anal Chem, 2012, 84:2129-2132.
Cheng, "The Contrast Formation in Optical Microscopy," Handbook of Biological Confocal Microscopy, 2006, Chapter 8, pp. 162-206.

(56) References Cited

OTHER PUBLICATIONS

Chester et al., "Dimethyl sulfoxide-mediated primer Tm reduction: a method for analyzing the role of renaturation temperature in the polymerase chain reaction," Anal Biochem, Mar. 1993, 209(2):284-90.
Cheung et al., "Chitosan: An Update on Potential Biomedical and Pharmaceutical Applications," Mar Drugs, Aug. 2015, 13(8):5156-86.
Chial, "DNA Sequencing Technologies Key to the Human Genome Project," Nature Education, 2008, 1(1):219, 7 pages.
Chiang et al., "NFkappaB translocation in human microvessel endothelial cells using a four-compartment subcellular protein redistribution assay," J Biochem Biophys Methods, Nov. 2000, 46(1-2):53-68.
Chrisey et al., "Covalent attachment of synthetic DNA to self-assembled monolayer films," Nucleic Acids Res., Aug. 1996, 24(15):3031-9.
Chung et al., "Imaging single-cell signaling dynamics with a deterministic high-density single-cell trap array," Anal Chem, Sep. 2011, 83(18):7044-7052.
Chung et al., "Structural and molecular interrogation of intact biological systems," Nature, May 16, 2013, 497:332-337.
Ciaccio et al., "Systems analysis of EGF receptor signaling dynamics with microwestern arrays," Nat Methods, Feb. 2010, 7(2):148-55.
Clevers, "Modeling Development and Disease with Organoids," Cell, Jun. 2016, 165(7):1586-1597.
Cockroft et al., "A single-molecule nanopore device detects DNA polymerase activity with single-nucleotide resolution," J Am Chem Soc., Jan. 2008, 130(3):818-20.
Colegio et al., "In vitro transposition system for efficient generation of random mutants of Campylobacter jejuni," J Bacteriol., Apr. 2001, 183(7):2384-8.
Colin et al., "Enzyme engineering in biomimetic compartments," Curr Opin Street Biol., Aug. 2015, 33:42-51.
Collins et al., "Two-dimensional single-cell patterning with one cell per well driven by surface acoustic waves," Nature Communications, Nov. 2015, 6:8686, 11 pages.
Condina et al., "A sensitive magnetic bead method for the detection and identification of tyrosine phosphorylation in proteins by MALDI-TOF/TOF MS," Proteomics, 2009, 9:3047-3057.
Constantine et al., "Use of genechip high-density oligonucleotide arrays for gene expression monitoring," Life Sceience News, Amersham Life Science; 11-14, 1998.
Cook et al., "The effects of secondary structure and O2 on the formation of direct strand breaks upon UV irradiation of 5-bromodeoxyuridine-containing oligonucleotides," Chem Biol., Jul. 1999, 6(7):451-9.
Copeland et al., "Mitochondrial DNA Alterations in Cancer," Cancer Invest., 2002, 557-569.
Corces et al., "An improved ATAC-seq protocol reduces background and enables interrogation of frozen tissues", Nat. Methods. vol. 14(10):959-962, 2017.
Corces et al., "Lineage-specific and single-cell chromatin accessibility charts human hematopoiesis and leukemia evolution," nature genetics, Oct. 2016, 48(10):1193-1203.
Cornett et al., "MALDI imaging mass spectrometry: molecular snapshots of biochemical systems," Nature Methods, 2007, 4(10):828-833.
Cox et al., "Tissue subcellular fractionation and protein extraction for use in mass-spectrometry-based proteomics," Nat Protoc., 2006, 1(4):1872-8.
Craig, "Transposon Tn7," Curr Top Microbiol Immunol., 1996, 204:27-48.
Craig, "V(D)J recombination and transposition: closer than expected," Science, Mar. 1996, 271(5255):1512, 1 page.
Crosetto et al, "Spatially resolved transcriptomics and beyond," Nature Review Genetics, 2015, 57-66.
Cujec et al. "Selection of v-abl tyrosine kinase substate sequences from randomized peptide and cellular proteomic libraries using mRNA display," Chemistry and Biology, 2002, 9:253-264.
Curtis et al., "Adhesion of cells to polystyrene surfaces," J Cell Biol., Nov. 1983, 97(5):1500-1506.
Czarnik, "Encoding methods for combinatorial chemistry," Curr Opin Chem Biol., Jun. 1997, 1(1):60-6.
Dahl et al., "Circle-to-circle amplification for precise and sensitive DNA analysis," Proc. Natl. Acad. Sci., 2004, 101:4548-4553.
Dalma-Weiszhausz et al., "The affymetrix GeneChip platform: an overview," Methods Enzymol., 2006, 410:3-28.
Dalmeijer et al., "Matrix Gla Protein Species and Risk of Cardiovascular Events in Type 2 Diabetic Patients," Diabetes Care, Nov. 2013, 36(11):3766-71.
Dandapani et al., "Selecting, Acquiring, and Using Small Molecule Libraries for High-Throughput Screening," Curr Protoc Chem Biol., Sep. 2012, 4:177-191.
Darmanis, et al., "ProteinSeq: High-Performance Proteomic Analyses by Proximity, Ligation and Next Generation Sequencing," PLos One, 2011, 6(9):e25583.
Darnell, Jr., "Reflections on the history of pre-mRNA processing and highlights of current knowledge: A unified picture," RNA, Feb. 2013, 19:443-460, 19 pages.
Datlinger et al., "Pooled CRISPR screening with single-cell transcriptome readout," Nat Methods, Mar. 2017, 14(3):297-301.
Daubendiek et al., "Rolling-Circle RNA Synthesis: Circular Oligonucleotides as Efficient Substrates for T7 RNA Polymerase," J. Am. Chem. Soc., 1995, 117:77818-7819.
Davies et al., "How best to identify chromosomal interactions: a comparison of approaches.", Nat. Methods 14, 125-134, 2017.
Dawson et al., "Genetic animal models of Parkinson's disease," Neuron, Jun. 2010, 66(5):646-661.
De Clercq et al., "Approved Antiviral Drugs over the Past 50 Years," Clinical Microbiology Reviews, Jul. 2016, 29(3):695-747.
De Clercq, "A 40-year journey in search of selective antiviral chemotherapy," Annu Rev Pharmacol Toxicol., 2011, 51:1-24.
Deamer et al., "Characterization of nucleic acids by nanopore analysis," Acc Chem Res., Oct. 2002, 35(10):817-25.
Deamer et al., "Nanopores and nucleic acids: prospects for ultrarapid sequencing," Trends Biotechnol., Apr. 2000, 18(4):147-51.
Dean et al., "Comprehensive human genome amplification using multiple displacement amplification," Proc Natl. Acad. Sci. USA 99:5261-66, 2002.
Dean et al., "Rapid Amplification of Plasmid and Phage DNA Using Phi29 DNA Polymerase and Multiply-Primed Rolling Circle Amplification," Genome Research, Jun. 2001, 11:1095-1099.
Deibel et al., "Biochemical properties of purified human terminal deoxynucleotidyltransferase," J Biol Chem., May 1980, 255(9):4206-12.
Deo et al., "Detection of mammalian microRNA expression by in situ hybridization with RNA oligonucleotides," Dev Dyn., Sep. 2006, 235(9):2538-48.
Devine et al., "Efficient integration of artificial transposons into plasmid targets in vitro: a useful tool for DNA mapping, sequencing and genetic analysis," Nucleic Acids Res., Sep. 1994, 22(18):3765-72.
Dhindsa et al., "Virtual Electrowetting Channels: Electronic Liquid Transport with Continuous Channel Functionality," Lab Chip, 2010, 10:832-836.
Diez-Roux et al., "A high-resolution anatomical atlas of the transcriptome in the mouse embryo," PLoS Biol., Jan. 2011, 9(1):e1000582, 14 pages.
Ding et al., "On-chip manipulation of single microparticles, cells, and organisms using surface acoustic waves," PNAS, Jul. 2012, 109(28):11105-11109.
Dixit et al., "Perturb-Seq: Dissecting Molecular Circuits with Scalable Single-Cell RNA Profiling of Pooled Genetic Screens," Cell, Dec. 2016, 167(7):1853-1866.e17.
Doddridge et al., "UV-induced strand break damage in single stranded bromodeoxyuridine-containing DNA oligonucleotides," Chem Commun., 1998, p. 1997-1998.
Doshi et al., "In vitro nanobody discovery for integral membrane protein targets," Scientific Reports, Oct. 4, 2014, 4:6760, 8 pages.

(56) References Cited

OTHER PUBLICATIONS

Dressman et al., "Transforming single DNA molecules into fluorescent magnetic particles for detection and enumeration of genetic variations," Proc. Natl. Acad. Sci. USA, 2003, 100:8817-8822.

Drmanac et al., "Accurate sequencing by hybridization for DNA diagnostics and individual genomics," Nature Biotechnology, 16:54-58, 1998.

Druley et al., "Quantification of rare allelic variants from pooled genomic DNA," Nat. Methods 6: 263-65, 2009.

Duhr et al., "Why molecules move along a temperature gradient," Proc Natl Acad Sci USA, Dec. 2006, 103(52): 19678-19682.

Duncan et al., "Affinity chromatography of a sequence-specific DNA binding protein using teflon-linked oligonucleotides", Anal. Biochem. 169: 104-108, 1988.

Dundas et al., "Reference genes for measuring mRNA expression," Theory Biosci., May 17, 2012, 131:215-223.

Eagen, "Principles of Chromosome Architecture Revealed by Hi-C", Trends in Biochemical Sciences, vol. 43, No. 6, 10 pages, 2018.

Eberwine et al., "Analysis of gene expression in single live neurons," Proc. Natl. Acad. Sci., USA 89, 3010-3014, 1992.

Eberwine, "Amplification of mRNA Populations Using aRNA Generated from Immobilized Qligo(dT)-T7 Primed cDNA," BioTechniques 20 (4), 584, 1996.

Ebihara et al., "Molecular detection of dermatophytes and nondermatophytes in onychomycosis by nested polymerase chain reaction based on 28S ribosomal RNA gene sequences," Br J Dermatol., Nov. 2009, 161(5):1038-44.

Eguiluz et al., "Multitissue array review: A chronological description of tissue array techniques, applications and procedures," Pathology Research and Practice, 2006, 202:561-568.

Eisenberg et al., "Corrigendum to: Human housekeeping genes, revisited: [Trends in Genetics 29 (2013), 569-574]," Trends in Gen., Mar. 2014, 30(3):119-20.

Ekins et al., "Microarrays: their origins and applications," Trends in Biotechnology, Jun. 1999, 17(6):217-218.

Eldridge et al. "An in vitro selection strategy for conferring protease resistance to ligand binding peptides," Protein Eng Des Sel., 22(11): 691-698, 2009.

Ellington et al., "Antibody-based protein multiplex platforms: technical and operational challenges," Clin Chem 56(2): 186-193, 2010.

Emmert-Buck et al., "Laser capture microdissection," Science, Nov. 1996, 274(5289):998-1001.

Eng et al., "Profiling the transcriptome by RNA SPOTs", Nat Methods., 14(12): 1153-1155, 2017.

Ergin et al., "Proteomic Analysis of PAXgene-Fixed Tissues," J Proteome Res., 2010, 9(10):5188-96.

Escholarship.org [online], "Methods and devices for fabricating and assembling DNA and protein arrays for high-throughput analyses [electronic resource]," 2010, retrieved on Jun. 8, 2022, retrieved from URL<https://escholarship.org/uc/item/6tf7p46s>, 155 pages.

Espina et al., "Laser-capture microdissection," Nat Protoc, 2006, 1(2):586-603.

Evers et al., "The effect of formaldehyde fixation on RNA: optimization of formaldehyde adduct removal," J Mol Diagn., May 2011, 13(3):282-8.

Extended European Search Report in European Appln. No. 19159432.4, dated Jul. 10, 2019, 6 pages.

Extended European Search Report in European Appln. No. 21164281.4, dated Sep. 9, 2021, 5 pages.

Extended European Search Report in European Appln. No. 21164322.6, dated Sep. 6, 2021, 5 pages.

Extended European Search Report in European Appln. No. 22190953.4, dated Jan. 27, 2023, 6 pages.

Extended European Search Report in European Appln. No. 22190961.7, dated Dec. 6, 2022, 6 pages.

Extended European Search Report issued in European Appln. No. 19159432.4, dated Jul. 19, 2019, 6 pages.

Fahy et al., "Design and synthesis of polyacrylamide-based oligonucleotide supports for use in nucleic acid diagnostics," Nucleic Acids Res., Apr. 1993, 21(8):1819-26.

Falconnet et al., "Surface engineering approaches to micropattern surfaces for cell-based assays," Biomaterials, Jun. 2006, 27(16):3044-3063.

Fan et al., "Highly parallel SNP genotyping," Cold Spring Symp. Quant. Biol., 68: 69-78, 2003.

Fang et al., "Fluoride-cleavable biotinylation phosphoramidite for 5'-end-labeling and affinity purification of synthetic oligonucleotides," Nucleic Acids Res., Jan. 2003, 31(2):708-715.

Faruqi et al., "High-throughput genotyping of single nucleotide polymorphisms with rolling circle amplification," BMC Genomics, Aug. 2001, 2:4, 10 pages.

Fehlmann et al., "cPAS-based sequencing on the BGISEQ-500 to explore small non-coding RNAs," Clin Epigenetics, Nov. 2016, 8:123, 11 pages.

Ferreira et al., "Photocrosslinkable Polymers for Biomedical Applications," Biomedical Engineering-Frontiers and Challenges, Prof. Reza, 2011, 22 pages.

Fire and Xu, "Rolling replication of short DNA circles," Proc. Natl. Acad. Sci., 92: 4641-4645, 1995.

Fischer et al., "Hematoxylin and eosin staining of tissue and cell sections," CSH Protoc., May 2008, 3(5):1-3.

Flanigon et al., "Multiplex protein detection with DNA readout via mass spectrometry," N. Biotechnol., 30(2): 153-158, 2013.

Flicek et al., "Ensembl 2014," Nucleic Acids Res., Jan. 2014, 42(Database issue):D749-D755.

Fluidigm, "Equivalence of Imaging Mass Cytometry and Immunofluorescence on FFPE Tissue Sections," White Paper, 2017, 12 pages.

Fodor et al., "Light-Directed, Spatially Addressable Parallel Chemical Synthesis," Science, 251(4995), 767-773, 1995.

Folch et al., "Microfabricated elastomeric stencils for micropatterning cell cultures," J Biomed Mater Res, Nov. 2000, 52(2):346-353.

Forcucci et al., "All-plastic miniature fluorescence microscope for point-of-care readout of bead-based bioassays.," J. Biomed Opt. 20 (10): 105010, 15 pages, 2015.

Fredriksson et al., "Multiplexed protein detection by proximity ligation for cancer detection," Nature Methods, 4(4): 327-29, 2007.

Fredriksson et al., "Multiplexed proximity ligation assays to profile putative plasma biomarkers relevant to pancreatic and ovarian cancer," Clin. Chem., 5(3): 582-89, 2008.

Fredriksson et al., "Protein detection using proximity-dependent DNA ligation assays," Nature Biotech., 20: 473-77, 2002.

Frese et al., "Formylglycine Aldehyde Tag-Protein Engineering through a Novel Posttranslational Modification," ChemBioChem., 10: 425-27, 2009.

Fu et al., "Counting individual DNA molecules by the stochastic attachment of diverse labels," PNAS, 108:9026-9031, 2011.

Fu et al., "Repeat subtraction-mediated sequence capture from a complex genome," Plant J., Jun. 2010, 62(5):898-909.

Fullwood et al., "Next-generation DNA sequencing of paired-end tags (PET) for transcriptome and genome analyses," Genome Res., 19: 521-532, 2009.

Galon et al., "The immune score as a new possible approach for the classification of cancer," J Transl Med., Jan. 2012, 10:1, 4 pages.

Gamper et al., "Gene expression profile of bladder tissue of patients with ulcerative interstitial cystitis," BMC Genomics, Apr. 28, 2009, 10(199):1-17.

Gans et al., "Inkjet Printing of Polymers: State of the Art and Future Developments," Advanced Materials, Feb. 2004, 16(3):203-213.

Gao et al., "High density peptide microarrays. In situ synthesis and applications," Molecular Diversity, 8, 177-187, 2004.

Gao et al., "Q&A: Expansion microscopy", BMC Biology, 15: 50, 9 pages, 2017.

Gaspar, "Strength in numbers: quantitative single-molecule RNA detection assays," Wiley Interdiscip Rev DevBiol., Mar.-Apr. 2015,4(2):135-50.

Geiss et al., "Direct multiplexed measurement of gene expression with color-coded probe pairs," nature biotechnology, 2008, 26(3):317-325.

Genbank Accession No. AC009495.1, "*Homo sapiens* clone NH0490I02, * Sequencing in Progress *, 12 unordered pieces," Aug. 24, 1999, 53 pages.

(56) References Cited

OTHER PUBLICATIONS

Genbank Accession No. AC009495.5, "*Homo sapiens* BAC clone RP11-49012 from 2, complete sequence," Apr. 21, 2005, 32 pages.
Genbank Accession No. AC037198.2, "*Homo sapiens* chromosome 15 clone CTD-2033D15 map 15ql4, * Sequencing in Progress *, 62 unordered pieces," Apr. 25, 2000, 39 pages.
Genbank Accession No. AC087379.2, "*Homo sapiens* chromosome 11 clone RP11-396020 map 11, * Sequencing in Progress *, 5 ordered pieces," Jul. 6, 2002, 47 pages.
Genbank Accession No. AC087741.1, "*Homo sapiens* chromosome 17 clone RP11-334C17 map 17, Low-Pass Sequence Sampling," Jan. 22, 2001, 18 pages.
Genbank Accession No. AC100826.1, "*Homo sapiens* chromosome 15 clone RP11-279F6 map 15, Low-Pass Sequence Sampling," Nov. 22, 2001, 21 pages.
Genbank Accession No. AL445433.14, "Human DNA sequence from clone RP11-234N17 on chromosome 1, complete sequence," Jan. 24, 2013, 32 pages.
Genbank Accession No. AL445524.1, "*Homo sapiens* chromosome 1 clone RP11-295G20, Working Draft Sequence, 19 unordered pieces," Oct. 14, 2000, 47 pages.
Gene@arrays[online], BeadArray Technology, available on or before Feb. 14, 2015, via Internet Archive: Wayback Machine URL <https://web.archive.org/web/20150214084616/http://geneaarrays.com/services/microarrays/illumina/beadarray-technology/>, [retrieved on Jan. 30, 2020], 3 pages.
Genome.ucsc.edu, [online], "Genome Browser Gateway," 2000, retrieved on Jun. 11, 2021, retrieved from URL<https://genome.ucsc.edu/cgi-bin/hgGateway>, 3 pages.
Gerard et al., "Excess dNTPs minimize RNA hydrolysis during reverse transcription," Biotechniques, Nov. 2002, 33(5):984, 986, 988, 990.
Gerdtsson et al., "Evaluation of Solid Supports for Slide- and Well-Based Recombinant Antibody Microarrays", Microarrays (2016) 5:16, 2016.
Giacomello et al., "Spatially resolved transcriptome profiling in model plant species", Nature Plants 3, 17061, 11 pages, 2017.
Giam et al., "Scanning probe-enabled nanocombinatorics define the relationship between fibronectin feature size and stem cell fate," PNAS, Mar. 2012, 109(12):4377-4382.
Gibson et al., "Enzymatic assembly of DNA molecules up to several hundred kilobases," Nat Methods., May 2009, 6(5):343-5.
Gibson-Corley et al., "Principles for valid histopathologic scoring in research," Vet Pathol., Nov. 2013, 50(6): 1007-15.
Gilar et al., "Study of phosphorothioate-modified oligonucleotide resistance to 3'-exonuclease using capillary electrophoresis," J Chromatogr B Biomed Sci Appl., Aug. 28, 1998, 714(1):13-20.
Gill et al., "Nucleic acid isothermal amplification technologies: a review," Nucleosides Nucleotides Nucleic Acids, Mar. 2008, 27(3):224-43.
Gilles et al., "Single nucleotide polymorphic discrimination by an electronic dot blot assay on semiconductor microchips," Nat Biotechnol, Apr. 1999, 17(4):365-70.
Glass et al., "SIMPLE: a sequential immunoperoxidase labeling and erasing method," J. Histochem. Cytochem., Oct. 2009, 57(10):899-905.
Gloor, "Gene targeting in *Drosophila*," Methods Mol Biol., 2004, 260:97-114.
Gnanapragasam, "Unlocking the molecular archive: the emerging use of formalin-fixed paraffin-embedded tissue for biomarker research in urological cancer," BJU International, 105, 274-278, 2009.
Goebl et al., "Development of a sensitive and specific in situ hybridization technique for the cellular localization of antisense oligodeoxynucleotide drugs in tissue sections," Toxicologic Pathology, Jun. 2007, 35(4):541-548.
Goldkom and Prockop, "A simple and efficient enzymatic method for covalent attachment of DNA to cellulose. Application for hybridization-restriction analysis and for in vitro synthesis of DNA probes.", Nucleic Acids Res. 14:9171-9191, 1986.

Goransson et al., "A single molecule array for digital targeted molecular analyses," Nucleic Acids Res., Nov. 25, 2009, 37(1):e7, 9 pages.
Goryshin et al., "Tn5 in vitro transposition," J Biol Chem., Mar. 1998, 273(13):7367-74.
Gotz et al., "Animal models of Alzheimer's disease and frontotemporal dementia," Nat Rev Neurosci., Jul. 2008, 9(7):532-44.
Govan et al., "Optochemical control of RNA interference in mammalian cells," Nucleic Acids Research, Dec. 2013, 41(22):10518-10528.
Grant et al., "Pathways and mechanisms of endocytic recycling," Nat. Rev. Mol. Cell Biol., Sep. 2009, 10(9):597-608.
Grokhovsky, "Specificity of DNA cleavage by ultrasound," Molecular Biology, 2006, 40(2):276-283.
Gross et al., "Technologies for Single-Cell Isolation," Int. J Mol. Sci., Jul. 2015, 16(8):16897-16919.
Grünweller et al., "Locked Nucleic Acid Oligonucleotides," BioDrugs, Jul. 2007, 21(4): 235-243.
Gu et al., "Multiplex single-molecule interaction profiling of DNA-barcoded proteins," Nature, Sep. 21, 2014, 515:554-557.
Gu et al., "Protein tag-mediated conjugation of oligonucleotides to recombinant affinity binders for proximity ligation," N Biotechnol., 30(2): 144-152, 2013.
Gudjonsson et al., "Myoepithelial cells: their origin and function in breast morphogenesis and neoplasia," J Mammary Gland Biol Neoplasia, Jul. 2005, 10(3):261-72.
Gunderson et al., "Decoding Randomly Ordered DNA Arrays," Genome Research 14: 870-877, 2004.
Guo et al., "Direct fluorescence analysis of genetic polymorphisms by hybridization with oligonucleotide arrays on glass supports," Nucleic Acids Res., Dec. 1994, 22(24):5456-65.
Guo et al., "RNA Sequencing of Formalin-Fixed, Paraffin-Embedded Specimens for Gene Expression Quantification and Data Mining," Int J Genomics, 2016, 2016:9837310, 11 pages.
Habib et al., "Div-Seq: Single-nucleus RNA-Seq reveals dynamics of rare adult newborn neurons," Science, Aug. 2016, 353(6302):925-8.
Hadley et al: "Determining composition of micron-scale protein deposits in neurodegenerative disease by spatially targeted optical microproteomics", ELIFE, Sep. 2015, 4(e09579): pp. 1-12.
Hafner et al., "Identification of microRNAs and other small regulatory RNAs using cDNA library sequencing," Methods, Jan. 2008, 44(1):3-12.
Hahnke et al., "Striptease on glass: validation of an improved stripping procedure for in situ microarrays," J Biotechnol., Jan. 2007, 128(1):1-13.
Hajduk et al., "Drug discovery: A question of library design," Nature, Feb. 2011, 470(7332):42-43.
Halova et al., "Mast cell chemotaxis—chemoattractants and signaling pathways," Front Immunol., May 2012, 3:119, 20 pages.
Hamaguchi et al., "Direct reverse transcription-PCR on oligo(dT)-immobilized polypropylene microplates after capturing total mRNA from crude cell lysates," Clin Chem., Nov. 1998, 44(11):2256-63.
Hammond et al., "Profiling cellular protein complexes by proximity ligation with dual tag microarray readout," PLoS ONE, 2012, 7(7):e40405.
Han et al., "3C and 3C-based techniques: the powerful tools for spatial genome organization deciphering", Molecular Cytogenetics (2018) 11:21, 10 pages, 2018.
Hanauer et al., "Separation of nanoparticles by gel electrophoresis according to size and shape," Nano Lett., Sep. 2007, 7(9):2881-5.
Hardenbol et al., "Highly multiplexed molecular inversion probe genotyping: over 10,000 targeted SNPs genotyped in a single tube assay," Genome Res., Feb. 2005, 15(2):269-75.
Hardenbol et al., "Multiplexed genotyping with sequence-tagged molecular inversion probes," Nature Biotechnol., Jun. 2003, 21(6):673-678.
Harris et al., "Chloroplast ribosomes and protein synthesis," Microbiol. Mol. Biol. Rev., Dec. 1, 1994, 58(4): 700-754.
Harris et al., "The design and application of target-focused compound libraries," Comb Chem High Throughput Screen, Jul. 2011, 14(6):521-531.

(56) References Cited

OTHER PUBLICATIONS

Harrow et al., "GENCODE: The reference human genome annotation for the ENCODE Project," Genome Res., Sep. 2012, 22(9):1760-1774.
Hattersley et al., "Development of a microfluidic device for the maintenance and interrogation of viable tissue biopsies," Lab Chip., Nov. 2008, 8(11):1842-6.
Hayes et al., "Electrophoresis of proteins and nucleic acids: I-Theory," BMJ, Sep. 1989, 299(6703):843-6.
He et al., "In situ synthesis of protein arrays," Current Opinion in Biotechnology, 19:4-9, 2008.
He et al., "Printing protein arrays from DNA arrays," Nature Methods, 5:175-77, 2008.
He, "Cell-free protein synthesis: applications in proteomics and biotechnology," New Biotechnology 25: 126-132, 2008.
Healy, "Nanopore-based single-molecule DNA analysis," Nanomedicine (Lond), Aug. 2007, 2(4):459-81.
Hedskog et al., "Dynamics of HIV-1 Quasispecies during Antiviral Treatment Dissected using Ultra-Deep Pyrosequencinq," PLoS One, 5(7):e11345, 2010.
Hein et al., "Click Chemistry, A Powerful Tool for Pharmaceutical Sciences", Pharm Res., 25(10): 2216-2230, 2008.
Hejatko et al., "In Situ Hybridization Techniques for mRNA Detection in Whole Mount *Arabidopsis* Samples," Nature Protocols, 2006, 1(4):1939-1946.
Hendrickson et al., "High sensitivity multianalyte immunoassay using covalent DNA-labeled antibodies and polymerase chain reaction," Nucleic Acid Research, Feb. 11, 1995, 23(3):522-529.
Hernandez et al., "Solution-phase and solid-phase sequential, selective modification of side chains in KDYWEC and KDYWE as models for usage in single-molecule protein sequencing," New J Chem., Jan. 2017, 41(2):462-469.
Hessner et al., "Genotyping of factor V G1691A (Leiden) without the use of PCR by invasive cleavage of oligonucleotide probes," Clin Chem., Aug. 2000, 46(8 Pt 1):1051-6.
Hiatt et al., "Parallel, tag-directed assembly of locally-derived short sequence reads," Nature Methods, 7(2): 119-25, 2010.
Hipp et al., "A novel BCMA/CD3 bispecific T-cell engager for the treatment of multiple myeloma induces selective lysis in vitro and in vivo," Leukemia, Oct. 2017, 31(10):2278, 31 pages.
Hlubek et al., "Heterogeneous expression of Wnt/beta-catenin target genes within colorectal cancer," Int J Cancer., Nov. 2007, 121(9):1941-8.
Ho et al., "Bacteriophage T4 RNA ligase 2 (gp24.1) exemplifies a family of RNA ligases found in all phylogenetic domains," PNAS, Oct. 2002, 99(20):12709-14.
Ho et al., "Characterization of an ATP-Dependent DNA Ligase Encoded by Chlorella Virus PBCV-1," Journal of Virology, Mar. 1997, 71(3):1931-1937.
Hober et al., "Human protein atlas and the use of microarray technologies," Curr Opin Biotechnol., Feb. 2008, 19(1):30-35.
Hoffman et al., "Formaldehyde crosslinking: a tool for the study of chromatin complexes," J Biol Chem., Oct. 2015, 290(44):26404-11.
Holmstrøm et al., "A highly sensitive and fast nomadioactive method for detection of polymerase chain reaction products," Anal Biochem, Mar. 1993, 209(2):278-83.
Hoyer et al., "Electrostatic spraying: a novel technique for preparation of polymer coatings on electrodes," Anal Chem, Nov. 1996, 68(21):3840-4.
Hsuih et al., "Novel, Ligation-Dependent PCR Assay for Detection of Hepatitis C Virus in Serum," Journal of Clinical Microbiology, Mar. 1996, 34(3):501-507.
Hu et al., "High reproducibility using sodium hydroxide-stripped long oligonucleotide DNA microarrays," Biotechniques, Jan. 2005, 38(1):121-4.
Hughes et al., "Microfluidic Western blotting," PNAS, Dec. 2012, 109(52):21450-21455.
Hycultbiotech.com, [online], "Immunohistochemistry, Paraffin" Apr. 2010, retrieved on Apr. 16, 2020, retrieved from URL<https://www.hycultbiotech.com/media/wysiwyg/Protocol_Immunohistochemistry_Paraffin_2.pdf>, 3 pages.
Hytönen et al., "Design and construction of highly stable, protease-resistant chimeric avidins," J Biol Chem., Mar. 2005, 280(11):10228-33.
Ichikawa et al., "In vitro transposition of transposon Tn3," J Biol. Chem., Nov. 1990, 265(31):18829-32, Abstract.
Illumina.com [online], "Array-Based Gene Expression Analysis," 2011, retrieved on Dec. 13, 2021, retrieved from URL<https://www.illumina.com/documents/products/datasheets/datasheet_gene_exp_analysis.pdf>, 5 pages.
Illumina.com [online], "Ribo-Zero® rRNA Removal Kit Reference Guide," Aug. 2016, retrieved on Apr. 26, 2022, retrieved from URL<https://jp.support.illumina.com/content/dam/illumina-support/documents/documentation/chemistry_documentation/ribosomal-depletion/ribo-zero/ribo-zero-reference-guide-15066012-02.pdf>, 36 pages.
Im et al., "An Introduction to Performing Immunofluorescence Staining," Biobanking: Methods and Protocols, Method in Molecular Biology, Yong (ed.), 2019, 1897, Chapter 26, 299-311.
Imbeaud et al., "Towards standardization of RNA quality assessment using user-independent classifiers of microcapillary electrophoresis traces," Nucleic Acids Res., Mar. 2005, 33(6):e56, 12 pages.
Inoue and Wittbrodt, "One for All—A Highly Efficient and Versatile Method for Fluorescent Immuno staining in Fish Embryos," PLoS One 6, e19713, 2011.
Invitrogen, Immune Response Biomarker Profiling Service Report, Invitrogen, 2009, 1-33.
Jabara et al., Accurate sampling and deep sequencing of the HIV-1 protease gene using a Primer ID. PNAS 108(50); 20166-20171, 2011.
Jain, "Transport of molecules, particles, and cells in solid tumors," Annu. Rev. Biomed. Eng., 1999, 1:241-263.
Jaitin et al., "Dissecting Immune Circuits by Linking CRISPR-Pooled Screens with Single-Cell RNA-Seq," Cell, Dec. 2016, 167(7):1883-1896.e15.
Jamur and Oliver, "Permeabilization of cell membranes.," Method Mal. Biol., 588: 63-66, 2010.
Jawhar et al., "Tissue Microarray: A rapidly evolving diagnostic and research tool," Annals of Saudi Medicine, Mar. 2009, 29(2):123-7.
Jemt et al., "An automated approach to prepare tissue-derived spatially barcoded RNA-sequencing libraries", Scientific Reports, 6: 37137, 10 pages, 2016.
Jennane et al., "Photolithography of self-assembled monolayers: optimization of protecting groups by an electroanalytical method," Can. J Chem., Dec. 1996, 74(12):2509-2517.
Jensen et al., "Zinc fixation preserves flow cytometry scatter and fluorescence parameters and allows simultaneous analysis of DNA content and synthesis, and intracellular and surface epitopes," Cytometry A., Aug. 2010, 77(8):798-804.
Jensen, "Technical review: In situ hybridization," Anat Rec (Hoboken)., Aug. 2014, 297(8):1349-1353.
Jones et al., Comparative lesion sequencing provides insights into tumor evolution. Proc. Natl. Acad. Sci. USA 105(11): 4283-4288, 2008.
Joos et al., "Covalent attachment of hybridizable oligonucleotides to glass supports," Anal Biochem., Apr. 1997, 247(1):96-101.
Jucá et al., "Effect of dimethyl sulfoxide on reverse transcriptase activity," Braz. J. Med. Biol. Res., Mar. 1995, 28(3):285-90.
Juliano, "The delivery of therapeutic oligonucleotides," Nucleic Acids Res., Aug. 2016, 44(14):6518-6548.
Kainkaryam et al., "Pooling in high-throughput drug screening" Curr Opin Drug Discov Devel., May 2009, 12(3):339-50.
Kalantari et al., "Deparaffinization of formalin-fixed paraffin-embedded tissue blocks using hot water instead of xylene," Anal Biochem,, Aug. 2016, 507:71-3.
Kandoth et al., "Mutational landscape and significance across 12 major cancer types," Nature, Oct. 2013, 502(7471):333-339, 20 pages.

(56) References Cited

OTHER PUBLICATIONS

Kanehisa, "Use of statistical criteria for screening potential homologies in nucleic acid sequences", Nucleic Acids Res. 12: 203-213, 1984.
Kansal et al., "The use of cerebrospinal fluid and neuropathologic studies in neuropsychiatry practice and research," Psychiatr Clin North Am., Jun. 2015, 38(2):309-22.
Kap et al., "Histological Assessment of PAXgene Tissue Fixation and Stabilization Reagents," PLoS One 6, e27704, 10 pages, 2011.
Kapteyn et al., "Incorporation of Non-Natural Nucleotides Into Template-Switching Oligonucleotides Reduces Background and Improves cDNA Synthesis From Very Small RNA Samples," BMC Genomics, 2010, 11(413): 1-9.
Karlin et al., "Applications and statistics for multiple high-scoring segments in molecular sequences," Proc. Natl. Acad. Sci., Jun. 15, 1993, 90:5873-7.
Karmakar et al., "Organocatalytic removal of formaldehyde adducts from RNA and DNA bases," Nature Chemistry, Aug. 2015, 7(9):752-758.
Kashyap et al., "Selective local lysis and sampling of live cells for nucleic acid analysis using a microfluidic probe," Sci Rep., Jul. 2016, 6:29579, 10 pages.
Ke et al., "In situ sequencing for RNA analysis in preserved tissue and cells," Nat Methods., Sep. 2013, 10(9):857-60.
Ke et al., "In situ sequencing for RNA analysis in preserved tissue and cells," Nat Methods., Sep. 2013, Supplementary Materials, 29 pages.
Kelleher et al., "Characterization of RNA Strand Displacement Synthesis by Moloney Murine Leukemia Virus Reverse Transcriptase," J Biol Chem, Apr. 1998, 273(16):9976-86.
Kennedy-Darling et al., "Measuring the Formaldehyde Protein-DNA Cross-Link Reversal Rate," Analytical Chemistry, 2014, 86(12):5678-5681.
Kent et al., "Polymerase θ is a robust terminal transferase that oscillates between three different mechanisms during end-joining" Elife, Jun. 2016, 5:e13740, 25 pages.
Kibbe, "OligoCalc: an online oligonucleotide properties calculator," Nucleic Acids Res., Jul. 2007, 35:W43-6.
Kirby et al., "Cryptic plasmids of *Mycobacterium avium*: Tn552 to the rescue," Mol Microbiol., Jan. 2002, 43(1):173-86.
Kleckner et al., "Tn10 and IS10 transposition and chromosome rearrangements: mechanism and regulation in vivo and in vitro," Curr Top Microbiol Immunol., 1996, 204:49-82.
Koch et al., "Photochemical immobilization of anthraquinone conjugated oligonucleotides and PCR amplicons on solid surfaces," Bioconjugate Chem., Jul. 2000, 11(4):474-483.
Kokkat et al., "Archived formalin-fixed paraffin-embedded (FFPE) blocks: A valuable underexploited resource for extraction of DNA, RNA, and protein," Apr. 2013, 11(2):101-6.
Kolb et al., "Click Chemistry: Diverse Chemical Function from a Few Good Reactions," Angew. Chem. Int. Ed., 40(11): 2004-2021, 2001.
Kolbert et al., "Ribosomal DNA sequencing as a tool for identification of bacterial pathogens," Curr Opin Microbiol, Jun. 1999, 2(3):299-305.
Kolovos et al., "Investigation of the spatial structure and interactions of the genome at sub-kilobasepair resolution using T2C," Nat. Protoc. 13, 459-477, 2018.
König et al., "iCLIP reveals the function of hnRNP particles in splicing at individual nucleotide resolution," Nat Struct Mol Biol., Jul. 2010, 17(7):909-915.
Korbel et al., "Paired-End Mapping Reveals Extensive Structural Variation in the Human Genome," Science, 318(5849): 420-426, 2007.
Korlach et al., "Selective aluminum passivation for targeted immobilization of single DNA polymerase molecules in zero-mode waveguide nanostructures," Proc. Natl. Acad. Sci. USA 105, 1176-1181, 2008.
Kourou et al., "Machine learning applications in cancer prognosis and prediction," Computational and Structural Biotechnology Journal, Jan. 2015, 13:8-17.
Kozlov et al., "A High-Complexity Multiplexed Solution-Phase Assay for Profiling Protease Activity on Microarrays," Comb Chem High Throughput Screen, 11: 24-35, 2008.
Kozlov et al., "A Highly Scalable Peptide-Based Assay System for Proteomics," PLoS ONE, 7(6): e37441, 2012.
Kozlov et al., "A Method for Rapid Protease Substrate Evaluation and Optimization," Comb Chem High Throughput Screen, 9: 481-87, 2006.
Kretschy et al., "Next-Generation o-Nitrobenzyl Photolabile Groups for Light-Directed Chemistry and Microarray Synthesis," Angewandte Chemie International Edition, Jul. 2015, 54(29):8555-8559.
Kristensen et al., "High-Throughput Methods for Detection of Genetic Variation," BioTechniques, Feb. 2001, 30(2):318-332.
Kuijpers et al. "Specific recognition of antibody-oligonucleotide conjugates by radiolabeled antisense nucleotides: a novel approach for two-step radioimmunotherapy of cancer," Bioconjugate Chem., Jan. 1, 1993, 4(1):94-102.
Kumar et al., "Template-directed oligonucleotide strand ligation, covalent intramolecular DNA circularization and catenation using click chemistry," J Am Chem Soc., May 2007, 129(21):6859-64.
Kurz et al., "cDNA-Protein Fusions: Covalent Protein-Gene Conjugates for the In Vitro Selection of Peptides and Proteins," ChemBioChem., 2: 666-72, 2001.
Kwok, "High-throughput genotyping assay approaches," Pharmocogenomics, Feb. 2000, 1(1):95-100.
Kwon, "Single-molecule fluorescence in situ hybridization: Quantitative imaging of single RNA molecules," Department of Biomedical Engineering, Oregon Health & Science University, Feb. 2013, 46:65-72.
Lacar et al., "Nuclear RNA-seq of single neurons reveals molecular signatures of activation," Nat Commun., Apr. 2016, 7:11022, 12 pages.
LaFerla et al., "Animal models of Alzheimer disease," Cold Spring Harb Perspect Med., Nov. 2012, 2(11):a006320, 14 pages.
Lage et al., "Whole Genome Analysis of Genetic Alterations in Small DNA Samples Using Hyperbranched Strand Displacement Amplification and Array-CGH," Genome Research 13: 294-307, 2003.
Lake et al., "Neuronal subtypes and diversity revealed by single-nucleus RNA sequencing of the human brain," Science, Jun. 2016, 352(6293):1586-90.
Lakhin et al., "Aptamers: problems, solutions and prospects," Acta Naturae, Oct. 2013, 5(4):34-43.
Lampe et al., "A purified mariner transposase is sufficient to mediate transposition in vitro," EMBO J., Oct. 1996, 15(19):5470-9.
Lamture et al., "Direct detection of nucleic acid hybridization on the surface of a charge coupled device," Nucleic Acid Res., Jun. 1994, 22(11):2121-5.
Landegren et al., "Reading bits of genetic information: methods for single-nucleotide polymorphism analysis," Genome Res., Aug. 1998, 8(8):769-76.
Langdale et al., "A rapid method of gene detection using DNA bound to Sephacryl", Gene 36: 201-210, 1985.
Larman et al., "Autoantigen discovery with a synthetic human peptidome," Nature Biotechnology, doi:1 0.1038/nbt.1856, vol. 29, No. 6, pp. 535-541, 2011.
Larman et al., "Sensitive, multiplex and direct quantification of RNA sequences using a modified RASL assay," Nucleic Acids Research, 2014, 42(14):9146-9157.
Larsen et al., "Characterization of a recombinantly expressed proteinase K-like enzyme from a psychrotrophic *Serratia* sp," FEBS J., Jan. 2006, 273(1):47-60.
Larsson et al., "In situ detection and genotyping of individual mRNA molecules," Nat Methods, May 2010, 7(5):395-7.
Larsson et al., "In situ genotyping individual DNA molecules by target-primed rolling-circle amplification of padlock probes," Nat Methods, Dec. 2004, 1(3):227-32.

(56) References Cited

OTHER PUBLICATIONS

Lassmann et al., A Novel Approach for Reliable Microarray Analysis of Microdissected Tumor Cells From Formalin-Fixed and Paraffin-Embedded Colorectal Cancer Resection Specimens, J Mol Med, 87, 211-224, 2009.
Laurell et al., "Chip integrated strategies for acoustic separation and manipulation of cells and particles," Chem. Soc. Rev., Mar. 2007, 36(3):492-506.
Le Reste et al., "Characterization of dark quencher chromophores as nonfluorescent acceptors for single-molecule FRET," Biophysical Journal, Jun. 2012, 102(11):2658-2668.
Lee et al., "A novel COL3A1 gene mutation in patient with aortic dissected aneurysm and cervical artery dissections," Heart Vessels, Mar. 2008, 23(2):144-8.
Lee et al., "Cytokines in cancer immunotherapy," Cancers (Basel), Oct. 2011, 3(4):3856-3893.
Lee et al., "Fluorescent in situ sequencing (FISSEQ) of RNA for gene expression profiling in intact cells and tissues", Nature Protec, 10(3): 442-458, 2015.
Lee et al., "Highly multiplexed subcellular RNA sequencing in situ", Science, 343(6177): 1360-1363, 2014.
Lee et al., "Identifying T Cell Receptors from High-Throughput Sequencing: Dealing with Promiscuity in TCRα and TCRβ Pairing," PLoS Comput Biol., Jan. 2017, 13(1):e1005313, 25 pages.
Lee et al., "Improving the efficiency of genomic loci capture using oligonucleotide arrays for high throughput resequencing," BMC Genomics, Dec. 2009, 10:646, 12 pages.
Lee et al., "Protein nanoarrays generated by dip-pen nanolithography," Science, Mar. 2002, 295(5560):1702-1705.
Lein et al., "The promise of spatial transcriptomics for neuroscience in the era of molecular cell typing", Science 358, 64-69, 2017.
Lenard, "Viral Membranes," Encyclopedia of Virology, Jul. 2008, pp. 308-314.
Leriche et al., "Cleavable linkers in chemical biology.", Bioorganic & Medicinal Chemistry, 20: 571-582, 2012.
Levene et al., "Zero-Mode Waveguides for Single-Molecule Analysis at High Concentrations," Science 299, 682-686, 2003.
Li et al., "A photocleavable fluorescent nucleotide for DNA sequencing and analysis," Proc. Natl. Acad. Sci., 100: 414-419, 2003.
Li et al., "DNA molecules and configurations in a solid-state nanopore microscope," Nat Mater., Sep. 2003, 2(9):611-5.
Li et al., "RASL-seq for Massively Parallel and Quantitative Analysis of Gene Expression," Curr Protoc Mol Biol., Apr. 2012, 4(13):1-10.
Liberali et al., "Single-cell and multivariate approaches in genetic perturbation screens," Nat Rev Genet., Jan. 2015, 16(1):18-32.
Lin et al., "Highly multiplexed imaging of single cells using a high-throughput cyclic immunofluorescence method," Nat Commun., Sep. 2015, 6:8390, 7 pages.
Lin et al., "Histopathological assessment of inflammation and expression of inflammatory markers in patients with ketamine-induced cystitis," Mol Med Rep., Apr. 2015, 11(4):2421-2428.
Lin et al., "Microfluidic cell trap array for controlled positioning of single cells on adhesive micropatterns," Lab Chip, Feb. 2013, 13(4):714-721.
Linnarsson, "Recent advances in DNA sequencing methods—general principles of sample preparation," Experimental Cell Research, 316: 1339-1343, 2010.
Lipinski et al., "Cancer Evolution and the Limits of Predictability in Precision Cancer Medicine," Trends Cancer, Jan. 2016, 2(1):49-63.
Liu et al. "Barcoded oligonucleotides ligated on RNA amplified for multiplexed and parallel in situ analyses," Nucleic Acids Res., Mar. 8, 2021, 49(10):e58, 15 pages.
Liu et al., "Method for Quantitative Proteomics Research by Using Metal Element Chelated Tags Coupled with Mass Spectrometry," Analytical Chemistry, 2006, 78:6614-6621.
Liu et al., "Optochemical control of deoxyoligonucleotide function via a nucleobase-caging approach," Acc. Chem. Res., Jan. 2014, 47(1):45-55.
Liu et al., "Surface and interface control on photochemically initiated immobilization," J Am Chem Soc., Nov. 2006, 128(43):14067-72.
Liu et al., An integrated and sensitive detection platform for biosensing application based on Fe@Au magnetic nanoparticles as bead array carries Biosensors and Bioelectronics, 2010, 26(4):1442-1448.
Lizardi et al., "Mutation detection and single-molecule counting using isothermal rolling-circle amplification," Nat. Genet. 19: 225-232, 1998.
Lopez-Otín et al., "Protease degradomics: a new challenge for proteomics," Nat Rev Mol Cell Biol., Jul. 2002, 3(7):509-19.
Lou et al., "A review of room temperature storage of biospecimen tissue and nucleic acids for anatomic pathology laboratories and biorepositories," Clin Biochem., Mar. 2014, 47(4-5):267-73.
Lovatt et al., "Transcriptome in vivo analysis (TIVA) of spatially defined single cells in live tissue.", Nature Methods 11, 190-196, 2014.
Lu et al., "A microfluidic electroporation device for cell lysis," Lab Chip., Jan. 2005, 5(1):23-29.
Lubeck et al., "Single cell systems biology by super-resolution imaging and combinatorial labeling," Nature Methods, Jan. 2013, 9(7):743-748, 18 pages.
Lubeck et al., "Single-cell in situ RNA profiling by sequential hybridization," Nature Methods, Apr. 2014, 11(4):360-361, 2 pages (Supplemental Materials).
Lund et al., "Assessment of methods for covalent binding of nucleic acids to magnetic beads, Dynabeads, and the characteristics of the bound nucleic acids in hybridization reactions.", Nucleic Acids Res., 16: 10861-80, 1988.
Lundberg et al., "High-fidelity amplification using a thermostable DNA polymerase isolated from Pyrococcus furiosus.," Gene., 108(1): 1-6, 1991.
Lundberg et al., "Homogeneous antibody-based proximity extension assays provide sensitive and specific detection of low-abundant proteins in human blood," Nucleic Acids Res., 39(15): e102, 2011.
Lundberg et al., "Multiplexed homogeneous proximity ligation assays for high-throughput protein biomarker research in serological material," Mol Cell Proteomics, 10(4): M110.004978, 2011.
Lundin et al., "Increased throughput by parallelization of library preparation for massive sequencing," PLoS One, Apr. 2010, 5(4):e10029, 7 pages.
Lundquist et al., "Parallel confocal detection of single molecules in real time," Opt. Lett. 33, 1026-1028, 2008.
Lyamichev et al., "Invader assay for SNP genotyping," Methods Mol Biol., 2003, 212:229-40.
Lyamichev et al., "Polymorphism identification and quantitative detection of genomic DNA by invasive cleavage of oligonucleotide probes," Nat Biotechnol,, Mar. 1999, 17(3):292-6.
Lyck, et al., "Immunohistochemical Markers for Quantitative Studies of Neurons and Glia in Human Neocortex," J Histochem Cytochem 56, 201-21, 2008.
Lykidis et al., "Novel zinc-based fixative for high quality DNA, RNA and protein analysis," Nucleic Acids Res., Jun. 2007, 35(12):e85, 10 pages.
Ma et al., "Isothermal amplification method for next-generation sequencing," PNAS, Aug. 12, 2013, 110(35):14320-14323.
MacBeath et al., "Printing proteins as microarrays for high-throughput function determination," Science, Sep. 2000, 289(5485):1760-1763.
MacIntyre, "Unmasking antigens for immunohistochemistry.," Br J Biomed Sci. 58, 190-6, 2001.
Macosko et al., "Highly Parallel Genome-wide Expression Profiling of Individual Cells Using Nanoliter Droplets," Cell 161, 1202-1214, May 2015.
Magaki et al., "An introduction to Performance of Immunohistochemistry," Biobanking: Methods and Protocols, Method in Molecular Biology, Yong (ed.), 2019, 1897, Chapter 25, 289-298.
Malkov et al., "Multiplexed measurements of gene signatures in different analytes using the Nanostring nCounter™ Assay System." BMC research notes., 2009, 2:80.
Maniatis et al., "Spatiotemporal Dynamics of Molecular Pathology in Amyotrophic Lateral Sclerosis", 54 pages, 2018.

(56) References Cited

OTHER PUBLICATIONS

Marras, "Selection of fluorophore and quencher pairs for fluorescent nucleic acid hybridization probes," Methods Mol Biol., 2006, 335:3-16.
Martin, "Cutadapt removes adapter sequences from high-throughput sequencing reads," EMBnet Journal, 2011, 17(1):10-12.
Marzo et al., "Holographic acoustic elements for manipulation of levitated objects," Nature Communications, Oct. 2015, 6:8661, 7 pages.
Massey et al., "Fluorescence resonance energy transfer (FRET) for DNA biosensors: FRET pairs and Förster distances for various dye-DNA conjugates," Anal Chim Acta., May 2006, 568(1-2):181-9.
Masuda et al., "Analysis of chemical modification of RNA from formalin-fixed samples and optimization of molecular biology applications for such samples," Nucleic Acids Research, Nov. 1999, 27(22):4436-4443.
Materna et al., "High accuracy, high-resolution prevalence measurement for the majority of locally expressed regulatory genes in early sea urchin development," Gene Expr Patterns., 2010, 10(4-5):177-184.
Mathieson et al., "A Critical Evaluation of the PAXgene Tissue Fixation System: Morphology, Immunohistochemistry, Molecular Biology, and Proteomics," Am J Clin Pathol., Jul. 8, 2016, 146(1):25-40.
Mattheyses et al., "Imaging with total internal reflection fluorescence microscopy for the cell biologist," J Cell Sci., Nov. 2010, 123(Pt 21):3621-3628.
Mauleon et al., "Precise Spatial and Temporal Control of Oxygen within In Vitro Brain Slices via Microfluidic Gas Channels," PLoS One, Aug. 2012, 7(8):e43309, 9 pages.
McCloskey et al., "Encoding PCR Products with Batch-stamps and Barcodes," Biochem. Genet. 45: 761-767, 2007.
McDade et al., "Practical Considerations for Using Pooled Lentiviral CRISPR Libraries," Curr Protoc Mol Biol., Jul. 2016, 115:31.5.1-31.5.13.
Mcgee, "Structure and Analysis of Affymetrix Arrays," UTSW Microarray Analysis Course, Oct. 28, 2005, 68 pages.
McGinn et al., "New technologies for DNA analysis—a review of the READNA Project," N Biotechnol., May 3, 2016, 33(3): 311-30.
McGrath et al., "Building towards precision medicine: empowering medical professionals for the next revolution," BMC Medical Genomics, May 2016, 9(1):23, 6 pages.
McKernan et al., "Sequence and structural variation in a human genome uncovered by short-read, massively parallel ligation sequencing using two-base encoding," Genome Res., 19: 1527-41, 2009.
Megason et al., "Imaging in Systems Biology," Cell 130, Sep. 7, 2007, pp. 784-795.
Mele et al., "The Human Transcriptome Across Tissues and Individuals," Science, May 2015, 348(6235):660-5.
Metzker "Sequencing technologies—the next generation," Nature Reviews Genetics, 11: 31-46, 2010.
Meyer et al., "Fast evolving 18S rRNA sequences from Solenogastres (Mollusca) resist standard PCR amplification and give new insights into mollusk substitution rate heterogeneity," BMC Evol. Biol., Mar. 2010, 10:70, 12 pages.
Micke et al., "Biobanking of fresh frozen tissue: RNA is stable in nonfixed surgical specimens," Lab Invest., Feb. 2006, 86(2):202-11.
Miele et al., "Mapping cis- and trans-chromatin interaction networks using chromosome conformation capture (3C)," Methods Mol Biol., 2009, 464:105-21.
Mignardi et al., "Oligonucleotide gap-fill ligation for mutation detection and sequencing in situ," Nucleic Acids Research, Aug. 3, 2015, 43(22):e151, 12 pages.
Miller et al., "Basic Concepts of Microarrays and Potential Applications in Clinical Microbiology," Clinical Microbiology Reviews, vol. 22, No. 4, pp. 611-633, 2009.
Miller et al., "Chapter 11—Solid and Suspension Microarrays for Microbial Diagnostics," Methods in Microbiology, 2015, 42:395-431.

Miner et al., "Molecular barcodes detect redundancy and contamination in hairpin-bisulfite PCR," Nucleic Acids Res., Sep. 2004, 32(17):e135, 4 pages.
Mir et al., "Sequencing by cyclic ligation and cleavage (CycliC) directly on a microarray captured template," Nucleic Acids Research, 37(1):e5, 8 pages, 2009.
Mishra, "Three-dimensional genome architecture and emerging technologies: looping in disease", Genome Medicine, 9: 87, 14 pages, 2017.
Mitra et al., "Digital genotyping and haplotyping with polymerase colonies," Proc. Natl. Acad. Sci. USA, May 2003, 100(10):5926-5931.
Mitra et al., "Fluorescent in situ sequencing on polymerase colonies," Anal Biochem, Sep. 2003, 320(1):55-65.
Mitra et al., "In situ localized amplification and contact replication of many individual DNA molecules," Nucleic Acids Res., Dec. 1999, 27(24):e34, 6 pages.
Mitsuhashi et al., "Gene manipulation on plastic plates," Nature 357: 519-520, 1992.
Mizusawa et al., "A bacteriophage lambda vector for cloning with BamHI and Sau3A," Gene, 20: 317-322, 1982.
Mlecinik et al., "Histopathologic-based prognostic factors of colorectal cancers are associated with the state of the local immune reaction," J Clin Oncol., Feb. 2011, 29(6):610-8.
Moffitt et al., "RNA Imaging with Multiplexed Error-Robust Fluorescence In Situ Hybridization (MERFISH)," Methods Enzymol., 2016, 572:1-49.
Mohsen et al., "The Discovery of Rolling Circle Amplification and Rolling Circle Transcription," Acc Chem Res., Nov. 15, 2016, 49(11):2540-2550, 25 pages.
Moncada et al., "Building a tumor atlas: integrating single-cell RNA-Seq data with spatial transcriptomics in pancreatic ductal adenocarcinoma", Institute for Computational Medicine, bioRxiv, 28 pages, 2018.
Moor et al., "Spatial transcriptomics: paving the way for tissue-level systems biology", Science Direct, Current Opinion in Biotechnology, 46: 126-133, 2017.
Morlan et al., "Selective depletion of rRNA enables whole transcriptome profiling of archival fixed tissue," PLoS One, Aug. 2012, 7(8):e42882, 8 pages.
Mortazavi et al., "Mapping and quantifying mammalian transcriptomes by RNA-Seq," Nature Methods, 5(7): 621-8, 2008.
Moshrefzadeh et al., "Nonuniform photobleaching of dyed polymers for optical waveguides," Applied Physics Letters, 1993, 62:16-18.
Motea et al., "Terminal deoxynucleotidyl transferase: the story of a misguided DNA polymerase," Biochim Biophys Acta., May 2010, 1804(5):1151-66.
Mueller et al., "RNA Integrify Number (RIN)—Standardization of RNA Quality Control," Agilent Technologies, 2004, 8 pages.
Mukherjee et al., "Insects as models to study the epigenetic basis of disease," Prog Biophys Mol Biol., Jul. 2015, 118(1-2):69-78.
Nadji et al., "Immunohistochemistry of tissue prepared by a molecular-friendly fixation and processing system," Appl Immunohistochem Mol Morphol., Sep. 2005, 13(3):277-82.
Nagahara et al., "Neuroprotective effects of brain-derived neurotrophic factor in rodent and primate models of Alzheimer's disease," Nat Med., Mar. 2009, 15(3):331-337.
Nagai et al., "Site-specific DNA cleavage by antisense oligonucleotides covalently linked to phenazine di-N-oxide," J Biol. Chem., Dec. 1991, 266(35):23994-4002.
Nakamura et al., "Biocompatible inkjet printing technique for designed seeding of individual living cells," Tissue Eng, Nov. 2005, 11(11-12):1658-1666.
Nakao et al., "Myosin heavy chain gene expression in human heart failure," J Clin Invest., Nov. 1997, 100(9):2362-70.
Nallur et al., "Signal amplification by rolling circle amplification on DNA microarrays," Nucleic Acids Res., Dec. 1, 2001, 29(23):e118, 9 pages.
Nam et al., "Nanoparticle-Based Bio-Bar Codes for the Ultrasensitive Detection of Proteins," Science, Sep. 26, 2003, 301(5641):1884-1886.

(56) References Cited

OTHER PUBLICATIONS

Nandakumar et al., "How an RNA Ligase Discriminates RNA versus DNA Damage," Molecular Cell, 2004, 16(2):211-221.
Nandakumar et al., "RNA Substrate Specificity and Structure-guided Mutational Analysis of Bacteriophage T4 RNA Ligase 2," Journal of Biological Chemistry, Jul. 2004, 279(30):31337-31347.
Nawy, "Spatial transcriptomics", Nature Methods, vol. 15, No. 1, 2018.
NCBI Reference Sequence: NR_003286.2, "*Homo sapiens* RNA, 18S ribosomal 5 (RNA18S5), ribosomal RNA," dated Feb. 4, 2017, 2 pages.
Ncbi.nlm.nih.gov, [online], "Molecular Inversion Probe Assay," available on or before Oct. 14, 2014, via Internet Archive: Wayback Machine URL<https://web.archive.org/web/20141014124037/https://www.ncbi.nlm.nih.gov/probe/docs/techmip/>, retrieved on Jun. 16, 2021, retrieved from URL<https://www.ncbi.nlm.nih.gov/probe/docs/techmip/>, 2 pages.
Nelson et al., "Ebola Virus Does Not Induce Stress Granule Formation during Infection and Sequesters Stress Granule Proteins within Viral Inclusions," J Virol., Jul. 2016, 90(16):7268-7284.
Newman et al., "Robust enumeration of cell subsets from tissue expression profiles," Nature Methods, May 2015, 12(5):453-457.
Ng et al., "Gene identification signature (GIS) analysis for transcriptome characterization and genome annotation," Nature Methods, 2(2): 105-111, 2005.
Ng et al., "Massively parallel sequencing and rare disease," Human Malec. Genetics, 19(2): R119-R124, 2010.
Ng et al., "Multiplex sequencing of paired-end ditags (MS-PET): a strategy for the ultra-high-throughput analysis of transcriptomes and genomes," Nucleic Acids Research, Jul. 2006, 34(12): e84, 10 pages.
Nichols et al., "RNA Ligases," Curr Protoc Mol Biol., Oct. 2008, 84(1):3.15.1-3.15.4.
Nicholson, "Diffusion and related transport mechanisms in brain tissue," Rep. Prog. Phys., Jun. 2001, 64(7):815-884.
Niedringhaus et al., "Landscape of next-generation sequencing technologies," Anal Chem., Jun. 2011, 83(12):4327-41.
Niemeyer, "The developments of semisynthetic DNA-protein conjugates," Trends Biotechnol, Sep. 2002, 20(9): 395-401.
Niimi et al., "Melting Temperature Mapping Method: A Novel Method for Rapid Identification of Unknown Pathogenic Microorganisms within Three Hours of Sample Collection," Sci. Rep., Jul. 2015, 5:12543, 13 pages.
Nikiforov et al., "The use of 96-well polystyrene plates for DNA hybridization-based assays: an evaluation of different approaches to oligonucleotide immobilization," Anal Biochem, May 1995, 227(1):201-9.
Niklas et al., "Selective permeabilization for the high-throughput measurement of compartmented enzyme activities in mammalian cells," Anal Biochem, Sep. 2011, 416(2):218-27.
Nilsson et al., "Padlock Probes: Circularizing Oligonucleotides for Localized DNA Detection," Science, Sep. 30, 1994, 265(5181):2085-2088.
Nilsson et al., "RNA-templated DNA ligation for transcript analysis," Nucleic Acids Res., Jan. 2001, 29(2):578-81.
Nuovo, "In situ PCR: protocols and applications.," Genome Res, Feb. 1995, 4 (4):151-167.
Ohtsubo et al., "Bacterial insertion sequences," Curr Top Microbiol Immunol., 1996, 204:1-26.
Oleinikov et al., "Self-assembling protein arrays using electronic semiconductor microchips and in vitro translation," J Proteome Res, May-Jun. 2003, 2(3): 313-319.
Olink Proteomics AB, Proseek® Multiplex 96x96 User Manual, 2016, 12 pages.
Olivier, "The Invader assay for SNP genotyping," Mutat. Res., Jun. 2005, 573(1-2):103-110.
Oren et al., "Selective lysis of bacteria but not mammalian cells by diastereomers of melittin: structure-function study," Biochemistry, Feb. 1997, 36(7):1826-35.

Osada et al., "Epitope mapping using ribosome display in a resconstituted cell-free protein synthesis system," J Biochem, May 2009, 145(5): 693-700.
O-Shannessy et al., "Detection and quantitation of hexa-histidine-tagged recombinant proteins on western blots and by a surface plasmon resonance biosensor technique," Anal Biochem, 229(1): 119-124, 1995.
Ostuni et al., "Patterning Mammalian Cells Using Elastomeric Membranes," Langmuir, Aug. 2000, 16(20):7811-7819.
Ozsolak et al., "Digital transcriptome profiling from attomole-level RNA samples," Genome Res., Apr. 2010, 20(4):519-25.
Palamanda et al., "Evaluation of CYP1A1 and CYP2B1/2 m-RNA Induction in Rat Liver Slices Using the NanoString® Technology: A Novel Tool for Drug Discovery Lead Optimization," Drug metabolism letters, Nov. 3, 2009, 3(3):171-175.
Pandey et al., "Inhibition of terminal deoxynucleotidyl transferase by adenine dinucleotides. Unique inhibitory action of Ap5A," FEBS Lett., Mar. 1987, 213(1):204-8.
Park et al., "Cancer gene therapy using adeno-associated virus vectors," Front Biosci., Jan. 2008, 13:2653-59.
Park et al., "The Estimation of Breast Cancer Disease-Probability by Difference of Individual Susceptibility," Cancer Res. Treat., Feb. 2003, 35(1):35-51, Abstract.
Patil et al., "DNA-based therapeutics and DNA delivery systems: a comprehensive review," AAPS J, Apr. 2005, 7(1):E61-77.
Patton et al., "Rainbow's end: the quest for multiplexed fluorescence quantitative analysis in proteomics." Current Opinion in Chemical Biology, Feb. 1, 2002, 6(1):63-69.
PCT International Preliminary Report on Patentability in International Appln. No. PCT/EP2016/057355, dated Oct. 10, 2017, 7 pages.
PCT International Search Report and Written Opinion issued in International Appln. No. PCT/EP2016/057355, dated Aug. 5, 2016, 8 pages.
Pearson et al., "Improved tools for biological sequence comparison," Proc. Natl. Acad. Sci., May 1988, 85:2444-2448.
Pellestor et al., "The peptide nucleic acids (PNAs), powerful tools for molecular genetics and cytogenetics," Eur J Hum Genet., Sep. 2004, 12(9):694-700.
Pemov et al., "DNA analysis with multiplex microarray-enhanced PCR," Nucl. Acids Res., Jan. 2005, 33(2):e11, 9 pages.
Penland et al., "RNA expression analysis of formalin-fixed paraffin-embedded tumors," Laboratory Investigation, Apr. 2007, 87(4):383-391.
Perler et al., "Intervening sequences in an Archaea DNA polymerase gene," PNAS USA, Jun. 1992, 89(12): 5577-5581.
Perocchi et al., "Antisense artifacts in transcriptome microarray experiments are resolved by actinomycin D," Nucleic Acids Res., 2007, 35(19):e128, 7 pages.
Petterson et al., "Generations of sequencing technologies," Genomics, 2009, 105-111.
Picelli et al., "Full-length RNA-seq from single cells using Smart-seq2," Nat Protoc., Jan. 2014, 9(1):171-81.
Picelli et al., "Tn5 transposase and tagmentation procedures for massively scaled sequencing projects," Genome Res., Dec. 2014, 24(12):2033-40.
Pipenburg et al., "DNA detection using recombination proteins," PLoS Biol., Jul. 2006, 4(7):e204, 7 pages.
Pirici et al., "Antibody elution method for multiple immunohistochemistry on primary antibodies raised in the same species and of the same subtypem," J. Histochem. Cytochem., Jun. 2009, 57(6):567-75.
Piston et al., "Fluorescent protein FRET: the good, the bad and the ugly," Trends Biochem Sci., Sep. 2007, 32(9):407-14.
Plasterk, "The Tc1/mariner transposon family," Curr Top Microbiol Immunol., 1996, 204:125-43.
Plongthongkum et al., "Advances in the profiling of DNA modifications: cytosine methylation and beyond," Nature Reviews Genetics, Aug. 2014, 15(10):647-661.
Pluen et al., "Diffusion of macromolecules in agarose gels: comparison of linear and globular configurations," Biophys J., Jul. 1999, 77(1):542-552.

(56) References Cited

OTHER PUBLICATIONS

Polsky-Cynkin et al., "Use of DNA Immobilizedon Plastic and Agarose Supports to Detect DNA by Sandwich Hybridization," Clin. Chem. 31: 1438-1443, 1985.
Porreca et al., "Polony DNA sequencing," Curr Protoc Mol Biol., Nov. 2006, Chapter 7, Unit 7.8, pp. 7.8.1-7.8.22.
Primebioscience.com, [online], "Brain Slice Systems, Recording Chambers, Stage Adapters, Temperature Controller," 2017, retrieved on Dec. 28, 2021, retrieved from URL<http://primebioscience.com/pb-applications/brain-slice-systems-recording-chambers-stage-adapterstemperature-controller/>, 7 pages.
Promega, "GoScript™ Reverse Transcription System—Technical Manual," promega.com, revised Dec. 2012, 24 pages.
U.S. Appl. No. 61/267,363, filed Dec. 7, 2009 (Year: 2009).
Punwaney et al., "Human papillomavirus may be common within nasopharyngeal carcinoma of Caucasian Americans: investigation of Epstein-Barr virus and human papillomavirus in eastern and western nasopharyngeal carcinoma using ligation-dependent polymerase chain reaction," Head & Neck, Jan. 1999, 21(1):21-29.
Qiu et al., "Combination probes with intercalating anchors and proximal fluorophores for DNA and RNA detection," Nucleic Acids Research, Sep. 2016, 44(17):e138, 12 pages.
Raab et al., "Human tRNA genes function as chromatin insulators," EMBO J., Jan. 2012, 31(2):330-50.
Raj et al., "Imaging individual mRNA molecules using multiple singly labeled probes," Nature Methods, Oct. 2008, 5(10):877-879, 9 pages.
Rajeswari et al., "Multiple pathogen biomarker detection using an encoded bead array in droplet PCR," J. Microbial Methods, Aug. 2017, 139:22-28.
Ramachandran et al., "Next-generation high-density self-assembling functional protein arrays," Nature Methods, Jun. 2008, 5(6):535-538.
Ramanujan et al., "Diffusion and convection in collagen gels: implications for transport in the tumor interstitium," Biophys. J., Sep. 2002, 83(3):1650-1660.
Ranki et al., "Sandwich hybridization as a convenient method for the detection of nucleic acids in crude samples", Gene 21: 77-85, cellulose, 1983.
Raouane et al., "Lipid conjugated oligonucleotides: a useful strategy for delivery," Bioconjug Chem., Jun. 2012, 23(6):1091-104.
Razonable, "Antiviral drugs for viruses other than human immunodeficiency virus," Mayo Clinic Proceedings, Oct. 2011, 86(10):1009-26.
Reijenga et al., "Buffer Capacity, Ionic Strength and Heat Dissipation in Capillary Electrophoresis," Journal of Chromatography A, Sep. 13, 1996, 744(1-2):147-153.
Reinartz et al., "Massively parallel signature sequencing (MPSS) as a tool for in-depth quantitative gene expression profiling in all organisms," Brief Funct Genomic Proteomic, Feb. 2002, 1(1):95-104.
Ren et al., "Star Polymers," Chem Rev., Jun. 2016, 116(12):6743-836.
Rettig et al., "Large-scale single-cell trapping and imaging using microwell arrays," Anal Chem, Sep. 2005, 77(17):5628-5634.
Reznikoff, "Tn5 as a model for understanding DNA transposition," Mol Microbiol., Mar. 2003, 47(5):1199-206.
Richardson et al., "Clarifying Tissue Clearing," Cell, Jul. 2015, 162(2):246-257.
Ripoli et al., "A Comparison of Fresh Frozen vs. Formalin-Fixed, Paraffin-Embedded Specimens of Canine Mammary Tumors via Branched-DNA Assay," Int. J. Mol. Sci., May 2016, 17(5):724, 11 pages.
Ristic et al., "Detection of Protein-Protein Interactions and Post-translational Modifications Using the Proximity Ligation Assay: Application to the Study of the SUMO Pathway," Methods Mol. Biol., 2016, 1449:279-90.
Ristova et al., "Study of hydrogenated amorphous silicon thin films as a potential sensor for He—Ne laser light detection," Applied Surface Science, Sep. 2003, 218(1-4):44-53.
Roberts et al., "RNA-peptide fusions for the in vitro selection of peptides and proteins," PNAS USA, Nov. 1997, 94: 12297-122302.
Robinson et al., "Small-sample estimation of negative binomial dispersion, with applications to SAGE data," Biostatistics, Apr. 2008, 9(2):321-332.
Rogers et al., "Immobilization of oligonucleotides onto a glass support via disulfide bonds: A method for preparation of DNA microarrays," Anal Biochem., Jan. 1999, 266(1):23-30.
Rogers et al., "Use of a novel cross-linking method to modify adenovirus tropism," Gene Ther., Dec. 1997, 4(12):1387-92.
Ronaghi et al., "A sequencing method based on real-time pyrophosphate," Science, Jul. 1998, 281(5375): 363-365.
Ronaghi et al., "Real-time DNA sequencing using detection of pyrophosphate release," Analytical Biochemistry, Nov. 1996, 242(1): 84-89.
Ronaghi, "Pyrosequencing sheds light on DNA sequencing," Genome Res, Jan. 2001, 11(1):3-11.
Rosenthal et al., "Cell patterning chip for controlling the stem cell microenvironment," Biomaterials, Jul. 2007, 28(21):3208-3216.
Rouillard et al., "OligoArray 2.0: design of oligonucleotide probes for DNA microarrays using a thermodynamic approach," Nuc. Acid Research, Jun. 2003, 31(12): 3057-3062.
Rountenberg et al., "Microfluidic probe: a new tool for integrating microfluidic environments and electronic wafer-probing," Lab Chip, Oct. 2009, 10(1):123-127.
Roy et al., "Assessing long-distance RNA sequence connectivity via RNA-templated DNA-DNA ligation," eLife, Apr. 2015, 4:e03700.
Rubin et al., "Whole-genome resequencing reveals loci under selection during chicken domestication.," Nature, Mar. 2010, 464: 587-591.
Rubina et al., "Hydrogel-based protein microchips: manufacturing, properties, and applications," Biotechniques, May 2003, 34(5):1008-14.
Running et al., "A procedure for productive coupling of synthetic oligonucleotides to polystyrene microtiter wells for hybridization capture," Biotechniques, Mar. 1990, 8(3):276-279.
Rush et al., "New Aldehyde Tag Sequences Identified by Screening Formylglycine Generating Enzymes in Vitro and in Vivo," J. of American Chemical Society, Aug. 2008, 130(37): 12240-12241.
Rusk, "Spatial transcriptomics," Nature Methods, Sep. 2016, 13(9):710-711.
Russell et al., "Molecular mechanisms of late endosome morphology, identity and sorting," Curr. Opin. Cell Bio., Aug. 2006, 18(4):422-428.
Sack et al., "Express photolithographic DNA microarray synthesis with optimized chemistry and high-efficiency photolabile groups," Journal of Nanobiotechnology, Mar. 2016, 14:14, 13 pages.
Salem et al., "Multidimensional transcriptomics provides detailed information about immune cell distribution and identity in HER2+ breast tumors", bioRxiv, 41 pages, 2018.
Sambrook and Russell, "Chapter 5, Gel Electrophoresis of DNA and Pulsed-field Agarose Gel Electrophoresis: Protocol 13, Preparation of DNA for Pulsed-field Gel Electrophoresis: Isolation of DNA from Mammalian Cells and Tissues," Molecular Cloning: A Laboratory Manual, 2001, 5 pages.
San Paulo et al., "High-resolution imaging of antibodies by tapping-mode atomic force microscopy: attractive and repulsive tip-sample interaction regimes," Biophys J., Mar. 2000, 78(3):1599-1605.
Sano et al., "Immuno-PCR: Very Sensitive Antigen Detection by Means of Specific Antibody-DNA Conjugates," Science, Oct. 2, 1992, 258(5079):120-122.
Sasagawa et al., "Comparative Transcriptome Analysis Identifies CCDC80 as a Novel Gene Associated with Pulmonary Arterial Hypertension," Front Pharmacol., Jun. 2016, 7:142, 13 pages.
Satija et al., "Spatial reconstruction of single-cell gene expression data," Nature, Apr. 13, 2015, 33(5):495-402, 14 pages.
Schaus et al., "A DNA nanoscope via auto-cycling proximity recording," Nat. Commun. 8, 696, 10 pages, 2017.
Schellings et al., "Absence of SPARC results in increased cardiac rupture and dysfunction after acute myocardial infarction," J Exp Med., Jan. 2009, 206(1):113-23.

(56) References Cited

OTHER PUBLICATIONS

Schena et al., "Quantitative monitoring of gene expression patterns with a complementary DNA microarray," Science, Oct. 1995, 270(5235):467-470.
Schena et al., "Entering the Postgenome Era," Science, 1995, 270:368-9, 371.
Schlapak et al., "Glass surfaces grafted with high-density poly (ethylene glycol) as substrates for DNA oligonucleotide microarrays," Langinuir, Jan. 2006, 22: 277-285.
Schmidt et al., "Cerebrospinal fluid melanin-concentrating hormone (MCH) and hypocretin-1 (HCRT-1, orexin-A) in Alzheimer's disease," PloS one, May 2013, 8(5):e63136, 6 pages.
Schmitt et al., "Detection of ultra-rare mutations by next-generation sequencing," PNAS (2012) 109:14508-14523.
Scholz et al., "The Molecular Chaperone Hsp90 Is Required for Signal Transduction by Wild-Type Hck and Maintenance of Its Constitutively Active Counterpart1," Cell Growth Differ., Aug. 2001, 12(8):409-417.
Schouten et al., "Relative quantification of 40 nucleic acid sequences by multiplex ligation-dependent probe amplification," Nucleic Acids Res., Jun. 2002, 30(12):e57, 13 pages.
Schroeder et al., "The RIN: an RNA integrity number for assigning integrity values to RNA measurements," BMC Molecular Biology, Jan. 2006, 7:3, 14 pages.
Schwartz et al., "Capturing native long-range contiguity by in situ library construction and optical sequencing," PNAS, Nov. 13, 2012, 109(46):18749-18754.
Schweitzer et al., "Immunoassays with rolling circle DNA amplification: A versatile platform for ultrasensitive antigen detection," Proc. Natl Acad. Sci. USA, May 22, 2000, 97:10113-119.
Schweitzer et al., "Multiplexed protein profiling on microarrays by rolling-circle amplification," Nature Biotechnology, Apr. 2002, 20(4):359-365.
Schwers et al., "A high-sensitivity, medium-density, and target amplification-free planar waveguide microarray system for gene expression analysis of formalin-fixed and paraffin-embedded tissue," Clin. Chem., Nov. 2009, 55(11):1995-2003.
ScienceDirect.com [online], "Plant Fibers," Definition, 2011, retrieved on Apr. 13, 2022, retrieved from URL<https://www.sciencedirect.com/topics/agricultural-and-biological-sciences/plant-fibers>, 9 pages.
Sekar et al., "Fluorescence resonance energy transfer (FRET) microscopy imaging of live cell protein localizations," J Cell Biol., Mar. 2003, 160(5):629-33.
Sergeeva et al., "Display technologies: Application for the discovery of drug and gene delivery aaents," Advanced Drug Delivery Reviews (2006) 58(15):1622-1654.
Seurynck-Servoss et al., "Evaluation of Surface Chemistries for Antibody Microarrays", Anal Biochem., 371(1): 105-115, 2007.
Shalon et al., "A DNA microarray system for analyzing complex DNA samples using two-color fluorescent probe hybridization," Genome Res., Jul. 1996, 6(7):639-45.
Shelbourne et al., "Fast copper-free click DNA ligation by the ring-strain promoted alkyne-azide cycloaddition reaction,", Chem. Commun., 47: 6257-6259, 2011.
Shendure et al., "Accurate Multiplex Polony Sequencing of an Evolved Bacterial Genome," Science, 2005, 309:1728-1732.
Shi et al., "The MicroArray Quality Control (MAQC) project shows inter- and intraplatform reproducibility of gene expression measurements," Nature Biotechnology, 2006, 24(9):1151-61.
Shi, "Enabling large-scale pharmacogenetic studies by high-throughput mutation detection and genotyping technologies," Clin. Chem., Feb. 2001, 47(2):164-172.
Shibata et al., "Detection of human papilloma vims in paraffin-embedded tissue using the polymerase chain reaction," J Exp Med., Jan. 1988, 167(1):225-30.
Shirai et al., "Novel Tools for Analyzing Gene Expressions in Single Cells," The 5th International Workshop on Approaches to Single-Cell Analysis, The University of Tokyo, Mar. 3-4, 2011, 1 page.
Shirai et al., "Photocrosslinkable polymers with degradable properties," Polymer Journal, Sep. 2014, 46:859-865.
Shoemaker et al., "Quantitative phenotypic analysis of yeast deletion mutants using a highly parallel molecular bar-coding strategy," Nature genetics (1996) 14:450-456.
Shrestha et al., "Understanding FRET as a research tool for cellular studies," Int J Mol Sci., Mar. 2015, 16(4):6718-56.
Shults et al., "A multiplexed protein kinase assay," Chem Bio Chem (2007) 8:933-942.
Sievertzon et al., "Transcriptome analysis in primary neural stem cells using a tag cDNA amplification method," BMC Neuroscience, Dec. 2005, 6: 28.
Simonis et al., "Nuclear organization of active and inactive chromatin domains uncovered by chromosome conformation capture-on-chip (4C)," Nat Genet., Nov. 2006, 38(11):1348-54.
Skene et al., "An efficient targeted nuclease strategy for high-resolution mapping of DNA binding sites," Elife, Jan. 2017, 6:e21856, 35 pages.
Skipper et al., "DNA transposon-based gene vehicles—scenes from an evolutionary drive," J Biomed Sci., Dec. 2013, 20(1):92, 23 pages.
Slomovic et al., "Addition of poly (A) and poly(A)-rich tails during RNA degradation in the cytoplasm of human cells," Proc Natl Acad Sci USA, Apr. 2010, 107(16):7407-12.
Slonim and Yanai, "Getting started in gene expression microarray analysis," Plos Computational Biology, 2009, 5(10):e1000543.
Smejkal et al., "Microfluidic isotachophoresis: a review," Electrophoresis, Jun. 2013, 34(11):1493-1509.
Smolock et al., "Ribosomal Protein L17, RpL17, is an Inhibitor of Vascular Smooth Muscle Growth and Carotid Intima Formation," Circulation, Nov. 2012, 126(20):2418-2427.
Soderberg et al. "Characterizing proteins and their interactions in cells and tissues using the in situ proximity ligation assay," Methods, Jul. 2008, 45(3):227-232.
Soderberg et al., "Direct observation of individual endogenous protein complexes in situ by proximity ligation," Nature Methods, 2006, 3:995-1000.
Son et al., "A platform for ultrasensitive and selective multiplexed marker protein assay toward early-stage cancer diagnosis," Nanomedicine, Feb. 7, 2007, 2(1):79-82.
Soni and Meller, "Progress toward ultrafast DNA sequencing using solid-state nanopores," Clin Chem., 2007, 53: 1996-2001.
Sparrer et al., "Intracellular detection of viral nucleic acids," Curr. Opin. Microbiol., Aug. 2015, 26:1-9.
Spiess et al., "A highly efficient method for long-chain cDNA synthesis using trehalose and betaine," Anal. Biochem., Feb. 2002, 301(2):168-74.
Spille et al., "Labelling and imaging of single endogenous messenger RNA particles in vivo," Journal of Cell Science, Oct. 2015, 128(20):3695-3706.
Spitale et al., "Structural imprints in vivo decode RNA regulatory mechanisms", Nature, 519(7544): 486-90, 2015.
Spurgeon et al., "High Throughput Gene Expression Measurement with Real Time PCR in a Microfluidic Dynamic Array," Plos ONE, 2008, 3(2):e1662.
Stahl et al., "Visualization and analysis of gene expression in tissue sections by spatial transcriptomics," Science, Jul. 2016, 353(6294):78-82.
Stahl et al., "Visualization and analysis of gene expression in tissue sections by spatial transcriptomics," Science, Jun. 2016, Supplementary Materials, 353(6294):78-82, 41 pages.
Stevens Jr. et al., "Enhancement of phosphoprotein analysis using a fluorescent affinity tag and mass spectrometry," Rapid Commun Mass Spectrom, 2005, 19(15):2157-62.
Stimpson et al., "Real-time detection of DNA hybridization and melting on oligonucleotide arrays by using optical wave guides," Proc Natl Acad Sci USA, Jul. 1995, 92(14):6379-83.
Stoddart et al., "Single-nucleotide discrimination in immobilized DNA oligonucleotides with a biological nanopore," PNAS U S A., May 2009, 106(19):7702-7707.
Strell et al., "Placing RNA in context and space—methods for spatially resolved transcriptomics", The FEBS Journal, 14 pages, 2017.

(56) References Cited

OTHER PUBLICATIONS

Stroh et al., "Quantum dots spectrally distinguish multiple species within the tumor milieu in vivo," Nat Med., Jun. 2005, 11(6):678-82.
Subramanian et al., "Gene set enrichment analysis: a knowledge-based approach for interpreting genome-wide expression profiles," PNAS, Oct. 2005, 102(43):15545-15550.
Suh et al., "A simple soft lithographic route to fabrication of poly (ethylene glycol) microstructures for protein and cell patterning," Biomaterials, Feb. 2004, 25(3):557-563.
Sumida et al., "Complement C1q-induced activation of β-catenin signalling causes hypertensive arterial remodelling," Nat Commun,, Feb. 2015, 6:6241, 12 pages.
Sumitomo et al., "Ca2+ ion transport through channels formed by -hemolysin analyzed using a microwell array on a Si substrate," Biosensors and Bioelectronics, 2012, 31(1):445-450.
Summersgill et al., "Fluorescence In Situ Hybridization Analysis of Formalin Fixed Paraffin Embedded Tissues, Including Tissue Microarrays," Chapter 4, Bridger, J. Ed., Methods in Molecular Biology 659, 2010, 51-70, 2010.
Sun et al., "Direct immobilization of DNA probes on non-modified plastics by UV irradiation and integration in microfluidic devices for rapid bioassay," Anal. Bio. Chem., 402: 741-748, 2012.
Surzhik et al., "Template-dependent biosynthesis of poly(G) x poly (C) and its antiviral activity in vitro and in vivo," Antiviral Res., May 1988, 38(2):131-40.
Sutherland et al., "Utility of formaldehyde cross-linking and mass spectrometry in the study of protein-protein interactions," J. Mass Spectrom., Jun. 2008, 43(6):699-715.
Swartz et al., "Interstitial flow and its effects in soft tissues," Annu Rev Biomed Eng., 2007, 9:229-56.
Syková et al., "Diffusion in brain extracellular space," Physiol Rev., Oct. 2008, 88(4):1277-340.
Tai et al., "Replication-competent retrovirus vectors for cancer gene therapy," Front Biosci., Jan. 2008, 13:3083-95.
Takahashi et al., "In Vitro Selection of Protein and Peptide Libraries Using mRNA Display," Nucleic Acid and Peptide Aptamers: Methods and Protocols (2009) 535:293-314 (Ch. 17).
Tan et al., "Parylene peel-off arrays to probe the role of cell-cell interactions in tumour angiogenesis," Integr Biol (Camb), Oct. 2009, 1(10):587-594.
Tang et al., "RNA-Seq analysis to capture the transcriptome landscape of a single cell.," Nat Protoc., 5: 516-35, 2010.
Taniguchi et al., "Quantitative analysis of gene expression in a single cell by qPCR," Nature Methods, 6, pp. 503-506, 2009.
Tawfik et al., "Man-made cell-like compartments for molecular evolution," Nat Biotechnol., Jul. 1998, 16(7):652-6.
Taylor et al., "Microfluidic local perfusion chambers for the visualization and manipulation of synapses," Neuron., Apr. 2010, 66(1):57-68, 25 pages.
Taylor et al., "Mitochondrial DNA mutations in human disease." Nature Reviews Genetics. May 2005, 6(5):389-402.
Tegtmeyer et al., "Alternative Interactions of the SV40 A Protein with DNA," Virology, 1981, 115:75-87.
Tentori et al., "Detection of Isoforms Differing by a Single Charge Unit in Individual Cells.", Chem. Int. Ed., 55, 12431, 2016.
Thacker et al., "Alkaline Hydrolysis—Carcass Disposal: A Comprehensive Review," National Agriculture Biosecurity Center, Aug. 2004, Chapter 6, pp. 1-12.
Thi Be Tu et al., "The serum/PDGF-dependent "melanogenic" role of the minute level of the oncogenic kinase PAK1 in melanoma cells proven by the highly sensitive kinase assay," Drug Discov Ther., Jan. 2017, 10(6):314-322.
Thiery et al., "Multiplex target protein imaging in tissue sections by mass spectrometry—TAMSIM," Rapid Commun. Mass Spectrom., 2007, 21:823-829.
Thorne et al., "In vivo diffusion analysis with quantum dots and dextrans predicts the width of brain extracellular space," Proc Natl Acad Sci USA, Apr. 2006, 103(14):5567-5572.
Thornton, "High rate thick film growth." Annual review of materials science, Aug. 1977, 7(1):239-60.
Tian et al., "Antigen peptide-based immunosensors for rapid detection of antibodies and antigens," Anal Chem May 26, 2009, 81 (13):5218-5225.
Tijssen et al., "Overview of principles of hybridization and the strategy of nucleic acid assays" in Techniques in Biochemistry and Molecular Biology—Hybridization with Nucleic Acid Probes, 1993, 24(Chapter 2), 65 pages.
Timofeev et al., "Regioselective immobilization of short oligonucleotides to acrylic copolymer gels," Nucleic Acids Res., Aug. 1996, 24(16):3142-8.
Tolbert et al., "New Methods for Proteomic Research: Preparation of Proteins with N-Terminal Cysteines for Labeling and Conjugation," Angewandte Chemie International Edition, Jun. 17, 2002, 41(12):2171-4.
Toseland, "Fluorescent labeling and modification of proteins," J Chem Biol., Apr. 2013, 6(3):85-95.
Toss et al., "Breast conservation in ductal carcinoma in situ (DCIS): what defines optimal margins?," Histopathology, Apr. 2017, 70(5):681-692.
Totet et al., "Immunocompetent infants as a human reservoir for Pneumocystis jirovecii: rapid screening by non-invasive sampling and real-time PCR at the mitochondrial large subunit rRNA gene," J Eukaryot Microbiol., 2003, pp. 668-669.
Toubanaki et al., "Dry-reagent disposable biosensor for visual genotyping of single nucleotide polymorphisms by oligonucleotide ligation reaction: application to pharmacogenetic analysis," Hum Mutat., Aug. 2008, 29(8):1071-8.
Toy et al., "A Simple Plastic Perfusion Chamber for Continuous Maintenance and Cinematography of Tissue Cultures," Experimental Cell Research, 1958, 14:97-103.
Tseng et al., "Magnetic nanoparticle-mediated massively parallel mechanical modulation of single-cell behavior," Nat Methods, Nov. 2012, 9(11):1113-1119.
Twyman et al., "Techniques Patents for SNP Genotyping," Pharmacogenomics, Jan. 2003, 4(1):67-79.
Tzanetakis et al., "The use of reverse transcriptase for efficient first- and second-strand cDNA synthesis from single- and double-stranded RNA templates," J Virol Methods, Mar. 2005, 24(1-2):73-7.
Ueno et al., "cDNA Display: Rapid Stabilitzation of mRNA Display," Antibody-Drug Conjugates, Methods in Molecular Biology, Jan. 2012, pp. 113-135.
Ulery et al., "Biomedical Applications of Biodegradable Polymers," J Polym Sci B Polym Phys., Jun. 2011, 49(12):832-864.
U.S. Appl. No. 60/416,118 Fan et al., Multiplex Nucleic Acid Analysis Using Archived or Fixed Samples, filed Oct. 3, 2002, 22 pages.
Valencia et al., "mRNA-Display-Based Selections for Proteins with Desired Functions: A Protease-Substrate Case Study." Biotechnology progress, May 2008, 24(3):561-9.
Valley et al., "Optoelectronic tweezers as a tool for parallel single-cell manipulation and stimulation," IEEE Trans Biomed Circuits Syst, Dec. 2009, 3(6):424-31.
Van Gelder et al., "Amplified RNA synthesized from limited quantities of heterogeneous cDNA," Proc. Natl. Acad. Sci. USA 87, 1663-1667, 1990.
Van Ness et al., "A versatile solid support system for oligodeoxynucleotide probe-based hybridization assays", Nucleic Acids Res. 19: 3345-3350, 1991.
Van Vught et al., "Site-specific functionalization of proteins and their applications to therapeutic antibodies," Comput Struct Biotechnol J., Feb. 2014, 9:e201402001, 13 pages.
Vandenbroucke et al., "Quantification of splice variants using real-time PCR," Nucleic Acids Research, 2001, 29(13):e68, 7 pages.
Vandernoot et al., "cDNA normalization by hydroxyapatite chromatography to enrich transcriptome diversity in RNA-seq applications," Biotechniques, Dec. 2012, 53(6):373-80.
Vasiliskov et al., "Fabrication of microarray of gel-immobilized compounds on a chip by copolymerization," Biotechniques, Sep. 1999, 27(3):592-606.

(56) References Cited

OTHER PUBLICATIONS

Velculescu et al., "Serial analysis of gene expression." Science, Oct. 20, 1995, 270(5235):484-7.
Veneziano et al., "Designer nanoscale DNA assemblies programmed from the top down," Science, Jun. 2016, 352(6293):1534, 10 pages.
Vermesh et al., "High-density, multiplexed patterning of cells at single-cell resolution for tissue engineering and other applications," Angew Chem Int Ed Engl, Aug. 2011, 50(32):7378-7380.
Vickovic et al., "Massive and parallel expression profiling using microarrayed single-cell sequencing," Nat. Commun. Oct. 14, 2016, 7:13182, 9 pages.
Vickovic et al., "Massive and parallel expression profiling using microarrayed single-cell sequencing," Nature Communications, 2016, 7(13182):1-9.
Vincent et al., "Helicase-dependent isothermal DNA amplification," EMBO Rep., Aug. 2004, 5(8):795-800.
Viollet et al., "T4 RNA ligase 2 truncated active site mutants: improved tools for RNA analysis," BMC Biotechnol., Jul. 2011, 11:72, 14 pages.
Vlassakis et al., "Effect of Polymer Hydration State on In-Gel Immunoassays," Anal Chem., Nov. 2015, 87(21): 11030-8.
Vogelstein et al., "Digital PCR," Proceedings of the National Academy of Sciences, Aug. 3, 1999, 96:9236-9241.
Wade et al., "Genome sequence, comparative analysis, and population genetics of the domestic horse.," Science., 326: 865-7, 2009.
Waichman et al., "Functional immobilization and patterning of proteins by an enzymatic transfer reaction," Analytical chemistry, Jan. 21, 2010, 82(4):1478-85.
Walker et al., "Strand displacement amplification—an isothermal, in vitro DNA amplification technique." Nucleic acids research, Apr. 11, 1992, 1992, 20(7):1691-1696.
Walker et al., Ed., "Chapter 1: Basic Techniques in Molecular Biology," Medical Biomethods Handbook, Humana Press, Totowa, New Jersey, 2005, 19 pages.
Wang et al., "Concentration gradient generation methods based on microfluidic systems," RSC Adv., 2017, 7:29966-29984.
Wang et al., "Imaging plasma membranes without cellular internalization: multisite membrane anchoring reagents based on glycol chitosan derivatives," J Master Chem B., Aug. 2015, 3(30):6165-6173.
Wang et al., "Mutations in NEXN, a Z-disc gene, are associated with hypertrophic cardiomyopathy," Am J Hum Genet, Nov. 2010, 87(5):687-93.
Wang et al., "Optimization of Process Conditions for Infected Animal Tissues by Alkaline Hydrolysis Technology," Procedia Environmental Sciences, 2016, 31:366-374.
Wang et al., "Paramagnetic microspheres with core-shell-ed structures," Journal of Materials Science, Apr. 2012, 47(16):5946-54.
Wang et al., "Single cell analysis: the new frontier in 'omics'," Trends Biotechnol., 28: 281-90, 2010.
Wang et al., "Tagmentation-based whole-genome bisulfite sequencing," Nature Protocols, Oct. 2013, 8(10):2022-2032.
Wang et al., "Three-dimensional intact-tissue sequencing of single-cell transcriptional states", Science, 361(6400), 22 pages, 2018.
Wang et al., "High-fidelity mRNA amplification for gene profiling." Nature biotechnology. Apr. 2000, 18(4):457-459.
Wang, "RNA amplification for successful gene profiling analysis," J Transl Med., Jul. 2005, 3:28, 11 pages.
Watanabe et al., "Cellular networks involved in the influenza virus life cycle," Cell Host & Microbe, Jun. 2010, 7(6):427-39.
Waxman et al., "De-regulation of common housekeeping genes in hepatocellular carcinoma," BMC Genomics, 2007, 1-9.
Weichhart et al., "Functional selection of vaccine candidate peptides from *Staphylococcus aureus* whole-genome expression libraries in vitro," Infection and Immunity, 2003, 71 (8):4333-4641.
Weinreich et al., "Evidence that the cis Preference of the Tn5 Transposase is Caused by Nonproductive Multimerization," Genes and Development, Oct. 1994, 8(19):2363-2374.
Weinstein et al., "DNA microscopy: Optics-free spatio-genetic imaging by a stand-alone chemical reaction", bioRxiv, 41 pages, 2018.
Wheeler et al., "Microfluidic device for single-cell analysis," Analytical Chemistry, Jul. 2003, 75(14):3581-3586.
Wiedmann et al., "Ligase chain reaction (LCR)—overview and applications," PCR Methods Appl., Feb. 1994, 3(4):S51-64.
Wikipedia.org [online], "Random hexamer," Jan. 2012, Retrieved on Jan. 21, 2022, retrieved from URL<https://en.wikipedia.org/w/index.php?title=Random_hexamer&oldid=473042236>, 1 page.
Williams, "RAC reviews serious adverse event associated with AAV therapy trial," Mol Ther., Dec. 2007, 15(12):2053-54.
Willi-Monnerat et al., "Comprehensive spatiotemporal transcriptomic analyses of the ganglionic eminences demonstrate the uniqueness of its caudal subdivision," Molecular and Cellular Nueorsciences 37(4):845-856, 2008.
Willner, "Stimuli-Controlled Hydrogels and Their Applications," Acc Chem Res., Apr. 2017, 50(4):657-658.
Wilson et al., "New transposon delivery plasmids for insertional mutagenesis in Bacillus anthracis," J Microbiol Methods, Dec. 2007, 71(3):332-5.
Wolf et al., "Rapid hybridization kinetics of DNA attached to submicron latex particles", Nucleic Acids Res. 15: 2911-2926, 1987.
Wong et al., "Direct Site-Selective Covalent Protein Immobilization Catalyzed by a Phosphopantetheinyl Transferase," J. Am. Chem Soc., 2008, 130:12456-64.
Woo et al., "A Comparison of cDNA, Oligonucleotide, and Affymetrix GeneChip Gene Expression Microarray Platforms," Journal of Biomolecular Techniques, 2004, 15(4), 276-284.
Wood et al., "Single cell trapping and DNA damage analysis using microwell arrays," PNAS, Jun. 2010, 107(22):10008-10013.
Worthington et al., "Cloning of random oligonucleotides to create single-insert plasmid libraries," Analyt. Biochem, 2001, 294:169-175.
Wright et al., "Reusable, reversibly sealable parylene membranes for cell and protein patterning," J Biomed Mater Res A., May 2008, 85(2):530-538.
Wu et al., "Detection DNA Point Mutation with Rolling-Circle Amplification Chip," Bioinformatics and Biomedical Engineering (ICBBE), 2010 4th International Conference on IEEE, Piscataway, NJ, USA, Jun. 18, 2010, 1-4 pages.
Wu et al., "Ribogenomics: the science and knowledge of RNA," Genomics Proteomics Bioinformatics, Apr. 2014, 12(2):57-63.
Xiao et al., "Direct determination of haplotypes from single DNA molecules," Nature Methods, 2009, 6(3):199-201.
Xie et al., "CryoFISH: Fluorescence In Situ Hybridization on Ultrathin Cryosections," Fluorescence in situ Hybridization (FISH), Jul. 2010, pp. 221-230.
Yamauchi et al., "Subcellular western blotting of single cells," Microsyst Nanoeng., 2017, 3:16079, 9 pages.
Yan et al., "Decorin gene delivery inhibits cardiac fibrosis in spontaneously hypertensive rats by modulation of transforming growth factor-beta/Smad and p38 mitogen-activated protein kinase signaling pathways," Hum Gene Ther., Oct. 2009, 20(10):1190-200.
Yang et al., "The role of tumor-associated macrophages in breast carcinoma invasion and metastasis," Int J Clin Exp Pathol., Jun. 2015, 8(6):6656-64.
Yasukawa et al., "Effects of organic solvents on the reverse transcription reaction catalyzed by reverse transcriptases from avian myeloblastosis virus and Moloney murine leukemia virus," Biosci Biotechnol Biochem., 2010, 74(9): 1925-30.
Ye et al., "Triggered self-assembly of magnetic nanoparticles," Sci Rep., Mar. 2016, 6:23145, 9 pages.
Yeakley et al., "Profiling alternative splicing on fiber-optic arrays," Nature Biotechnology, Apr. 2002, 20(4):353-358.
Yershov et al., "DNA analysis and diagnostics on oligonucleotide microchips," Proc. Natl. Acad. Sci. USA, May 1996, 93(10):4913-4918.
Yet et al., "Cardiac-specific expression of heme oxygenase-1 protects against ischemia and reperfusion injury in transgenic mice," Circ Res., Jul. 2001, 89(2):168-73.

(56) References Cited

OTHER PUBLICATIONS

Yin et al., "Genetically encoded short peptide tag for versatile protein labeling by Sfp phosphopantetheinyl transferase," PNAS, 2005, 102(44):15815-20.
Yonezawa et al., "DNA display for in vitro selection of diverse peptide libraries," Nucleic Acids Research, 2003, 31 (19):e118.
Yu et al., "Shrinkage estimation of dispersion in Negative Binomial models for RNA-seq experiments with small sample size," Bioinformatics, May 2013, 29(10):1275-1282.
Yusof et al., "Inkjet-like printing of single-cells," Lab Chip, Jul. 2011, 11(14):2447-2454.
Zahra et al., "Assessment of Different Permeabilization Methods of Minimizing Damage to the Adherent Cells for Detection of Intracellular RNA by Flow Cytometry," Avicenna Journal of Medical Biotechnology, Jan. 1, 2014, 6(1):38-46.
Zhang et al., "A novel mechanism of transposon-mediated gene activation," PLoS Genet., Oct. 2009, 5(10):e1000689, 10 pages.
Zhang et al., "Archaeal RNA ligase from thermoccocus kodakarensis for template dependent ligation," RNA Biol., Jan. 2017, 14(1):36-44.
Zhang et al., "Assembling DNA through Affinity Binding to Achieve Ultrasensitive Protein Detection," Angew Chem Int Ed (2013) 52:2-10.
Zhang et al., "Binding-induced DNA assembly and its application to yoctomole detection of proteins," Anal Chem (2012) 84(2):877-884.
Zhang et al., "Block-Cell-Printing for live single-cell printing," PNAS, Feb. 2014, 111(8):2948-2953.
Zhang et al., "Multiplex ligation-dependent probe amplification (MLPA) for ultrasensitive multiplexed microRNA detection using ribonucleotide-modified DNA probes†," Chem. Commun., Nov. 2013, 49:10013-10015.
Zhang et al., "Single-base mutational analysis of cancer and genetic diseases using membrane bound modified oligonucleotides," Nucleic Acids Res., Jul. 1991, 19(14):3929-33.
Zhang et al., "Stripping custom microRNA microarrays and the lessons learned about probe-slide interactions," Anal Biochem., Mar. 2009, 386(2):222-7.
Zhao et al., "Isothermal Amplification of Nucleic Acids," Chemical Reviews, Nov. 2015, 115(22):12491-12545.
Zheng et al., "Massively parallel digital transcriptional profiling of single cells," Nat Commun., Jan. 16, 2017, 8:14049, 12 pages.
Zheng et al., Origins of human mitochondrial point mutations as DNA polymerase mediated errors. Mutat. Res. 599(1-2): 11-20, 2006.
Zheng, "Spectroscopy-based quantitative fluorescence resonance energy transfer analysis," Methods Mol Biol., 2006, 337:65-77.
Zhou et al., "Genetically encoded short peptide tags for orthogonal protein labeling by Sfp and AcpS phosphopantetheinyl transferases," ACS Chemical Biol., 2007 2 5 : 337-346.
Zhu et al., "Reverse Transcriptase Template Switching: A SMART Approach for Full-Length cDNA Library Construction," BioTechniques, 2001, 30(4): 892-897.
Zieba et al., "Bright-field microscopy visualization of proteins and protein complexes by in situ proximity ligation with peroxidase detection," Clin Chem, Jan. 2010, 56(1):99-110.
Zilberman et al., "Genome-wide analysis of DNA methylation patterns," Development (2007) 134: 3959-3965.
Zlobec et al., "Next-generation tissue microarray (ngTMA) increases the quality of biomarker studies: an example using CD3, CD8, and CD45RO in the tumor microenvironment of six different solid tumor types," Journal of Translational Medicine, 2013 11(104):1-7.
Zuker, "Mfold web server for nucleic acid folding and hybridization prediction," Nucleic Acids Res., Jul. 2003, 31(13):3406-15.
[No Author Listed], "SMARTer Stranded Total RNA-Seq Kit—Pico Input Mammalian User Manual," Takara Bio, Dec. 31, 2016, 21 pages.
Advanced biophysis lab, "G5b: Supercoiling DNA by magnetic tweezers," biophysik.physik.uni-meuchen.de, available on or before Nov. 7, 2015, retrieved on Apr. 21, 2023, retrieved from URL <https://www.biophysik.physik.uni-muenchen.de/teaching/laboratory_courses/magnetic_tweezers/index.html#top>, 1 page.
Akatsuka et al., "Rapid screening of T-cell receptor (TCR) variable gene usage by multiplex PCR: Application for assessment of clonal composition," Tissue Antigens, Jan. 5, 1999, 53:122-134.
Akatsuka et al., "T cell receptor clonal diversity following allogeneic marrow grafting," Human Immunology, Jun.-Jul. 1996, 48:125-134.
Bessmertnykh et al., "Efficient Palladium-Catalyzed Synthesis of Aminopyridyl Phosphonates from Bromopyridines and Diethyl Phosphite," Synthesis, 2008, 10:1575-1579.
Bibikova et al., "Quantitative gene expression profiling in formalin-fixed paraffin-embedded tissues using universal bead arrays," The American Journal of Pathology, Nov. 1, 2004, 165(5):1799-1807.
Bowen et al., "Concurrent V(D)J recombination and DNA end instability increase interchromosomal trans—rearrangements in ATM-deficient thymocytes," Nucleic Acids Research, Apr. 1, 2013, 41(8):4535-4548.
Choi et al., "Multiplexed detection of mRNA using porosity-tuned hydrogel microparticles," Analytical chemistry, Sep. 28, 2012, 84(21):9370-9378.
Crisalli et al., "Importance of ortho Proton Donors in Catalysis of Hydrazone Formation," Org. Lett., 2013, 15(7):1646-1649.
Daley et al., "Predicting the molecular complexity of sequencing libraries," Nature Methods, Apr. 2013, 10:325-327.
Dellet et al., "Considerations for optimization of microRNA PCR assays for molecular diagnosis," Expert review of molecular diagnostics, Feb. 8, 2016, 16(4):407-414.
Falconnet et al., "Rapid, Sensitive and Real-Time Multiplexing Platform for the Analysis of Protein and Nucleic-Acid Biomarkers," Anal. Chem., Jan. 7, 2015, 87:1582-1589.
Fan et al., "A versatile assay for high-throughput gene expression profiling on universal array matrices," Genome Research, May 1, 2004, 14(5):878-885.
Goldmeyer et al., "Development of a novel one-tube isothermal reverse transcription thermophilic helicase-dependent amplification platform for rapid RNA detection," Journal of Molecular Diagnostics, American Society for Investigative Pathology and the Association for Molecular Pathology, Nov. 1, 2007, 9(5):639-644.
Holscher et al., "Application of Laser-Assisted Microdissection for Tissue and Cell-Specific Analysis of RNA," Progress in Botany, Jan. 2008, 69(3):141-167.
Hou et al., "Basic research and clinical application of immune repertoire sequencing," Int J Clin Exp Med., Oct. 30, 2016, 9(10):18868-18882.
Hughes et al., "Choose Your Label Wisely: Water-Soluble Fluorophores Often Interact with Lipid Bilayers," PLoS One, Feb. 4, 2014, 9(2):e87649, 8 pages.
Kim, "Development of Microdevices for Applications to Bioanalysis," Dissertation for the degree of Doctor of Philosophy, University of Texas at Austin, Aug. 2007, 176 pages.
Kung et al., "Long Noncoding RNAs: Past, Present, and Future," Genetics, Mar. 1, 2013, 193(3):651-669.
Kwon et al, Polyelectrolyte Gels-Fundamentals and Applications, Nov. 10, 2006, Polymer Journal, 38, pp. 1211-1219.
Laurent et al., "The Landscape of long noncoding RNA classification," Trends Genet., May 2015, 31(5):239-251.
Noshita et al., "Diethylenetriamine-Mediated Direct Cleavage of Unactivated Carbamates and Ureas," Org. Lett., Nov. 15, 2016, 18:6062-6065.
Robins et al., "Comprehensive assessment of T-cell receptor β-chain diversity in αβ T cells," Blood, Nov. 5, 2009, 114(19):4099-4107.
Stubbington et al., "T cell fate and clonality inference from single cell transcriptomes," Nature Methods, Apr. 2016, 13(4):329-332.
Tang et al., "Click Reactions: A Versatile Toolbox for the Synthesis of Peptide-Conjugates," Chemical Society Reviews, Jun. 12, 2014, pp. 1-27.
Villa et al., "Partial V(D)J Recombination Activity Leads to Omenn Syndrome," Cell, May 29, 1998, 93:885-896.
Williams et al., "Disc electrophoresis in polyacrylamide gels: extension to new conditions of pH and buffer," Annals of the New York Academy of Sciences, Dec. 1964, 121(2):373-381.

(56) References Cited

OTHER PUBLICATIONS

Almog et al., "The crystal structures of the psychrophilic subtilisin S41 and the mesophilic subtilisin Sph reveal the same calcium-loaded state," Proteins, Feb. 1, 2009, 74(2):489-496.

Cai et al, "Glutathione-mediated shedding of PEG layers based on disulfide-linked catiomers for DNA delivery," J. Mater. Chem., Sep. 20, 2011, 21(38):14639-14645.

Chen et al. "Arrayed profiling of multiple glycans on whole living cell surfaces." Analytical chemistry, Oct. 15, 2013, 85(22):11153-11158.

Eastburn et al., "Identification of Genetic Analysis of Cancer Cells with PCT-activated Cell Sorting," Nucleic Acids Research, Jul. 16, 2014, 42(16):e128, 10 pages.

Eastburn et al., "Ultrahigh-throughput Mammalian Single Cell Reverse-transcriptase Polymerase Chain Reaction in Microfluiding Drops," Analytical Chemistry, American Chemical Society, Aug. 20, 2013, 85(16):8016-8021.

Eisenberg et al., "Human housekeeping genes, revisited," Trends in Genetics, Oct. 2013, 29(10):569-574.

Ha et al, "Self-assembly hollow nanosphere for enzyme encapsulation," Soft Matter, Feb. 11, 2010, 6, 1405-1408, 10 pages.

Hu et al., "A thermo-degradable hydrogel with light-tunable degradation and drug release," Bio materials, Jan. 2017, 112:133-140.

Jeffers, "A Basic Subroutine for Geary's Contiguity Ratio," J. Royal Stat. Society, Series D, Dec. 1973, 22(4):299-302.

Ju et al, "Supramolecular dendrimer capsules by cooperative binding," Chem. Commun., Jan. 7, 2011, 47(1):268-270, 8 pages.

Kuiper et al, "Enzymes containing porous polymersomes as nano reaction vessels for cascade reactions," Org. Biomol, Chem, Oct. 15, 2008, 6(23):4315-4318.

Li et al., "Beyond Moran's I: Testing for Spatial Dependence Based on the Spatial Autoregressive Model," Geographical Analysis, Sep. 18, 2007, 39(4):357-375.

Li et al., "Encapsulation of a Nerve Agent Detoxifying Enzyme by a Mesoporous Zirconium Metal-Organic Framework Engenders Thermal and Long-Term Stability," J. Am. Chem. Soc., Jun. 24, 2016, 138(26):8052-8055, 4 pages.

Liu et al., "Preparation and Characterization of Temperature-Sensitive Poly(N-isopropylacrylamide)-b-poly(d,l-lactide) Microspheres for Protein Delivery," Biomacromolecules, 2003, 4(6):1784-1793.

Lyu et al., "One-Pot Synthesis of Protein-Embedded Metal-Organic Frameworks with Enhanced Biological Activities," Nano Lett., Sep. 11, 2014, 14:5761-5765.

Miller et al., "Rapid and Efficient Enzyme Encapsulation in a Dendrimer Silica Nanocomposite," Macromolecular Bioscience, Oct. 25, 2006, 6(10):839-845.

Rahimi et al, "Synthesis and Characterization of Thermo-Sensitive Nanoparticles for Drug Delivery Applications," J. Biomed. Nanotechnol. Dec. 2008, 4(4):482-490, 19 pages.

Shieh, et al., "Imparting Functionality to Biocatalysts via Embedding Enzymes into Nanoporous Materials by a de Novo Approach: Size-Selective Sheltering of Catalase in Metal-Organic Framework Microcrystals," J Am Chem Soc., Apr. 8, 2015, 137(13):4276-4279, 4 pages.

Soderberg, "Droplet Microfluidics Reverse Transcription and PCR Towards Single Cell and Exosome Analysis," Doctoral Thesis, KTH School of Biotechnology Science for Life Laboratory, 2017, 69 pages.

| Lane | Tiles | Density (K/mm2) | Cluster PF (%) | Phas/Prephas (%) | Reads (M) | Reads PF (M) | % >= Q30 |
|---|---|---|---|---|---|---|---|
| 1) Phi X | 21 | 904+/-62 | 92.1+/-1.0 | 0.797 / 0.097 | 9.83 | 9.06 | 94.6 |
| 2) 3.2 nM BODT-1 | 21 | 1026+/-171 | 48.2+/-36.6 | 0.948 / 0.151 | 11.15 | 5.59 | 72.9 |
| 3) 3.2 nM BODT-1 | 21 | 975+/-186 | 41.9+/-43.2 | 0.964 / 0.154 | 10.6 | 5.03 | 70.8 |
| 4) 3.2 nM BODT-1 | 21 | 1144+/-24 | 85.3+/-14.2 | 0.969 / 0.163 | 12.45 | 10.62 | 76.4 |
| 5) 3.2 nm BODT-1 | 21 | 1136+/-37 | 90.6+/-0.8 | 0.977 / 0.173 | 12.35 | 11.19 | 80.4 |
| 6) 3.2 nm BODT-1 | 21 | 1128+/-28 | 90.5+/-0.7 | 0.953 / 0.182 | 12.27 | 11.1 | 80.6 |
| 7) 3.2 nm BODT-1 | 21 | 1131+/-28 | 90.3+/-0.8 | 0.955 / 0.170 | 12.3 | 11.1 | 11.6 |
| 8) Phi X | 21 | 763+/-41 | 91.3+/-0.4 | 0.756 / 0.135 | 8.3 | 7.58 | 94 |

FIG. 3

SPATIALLY DISTINGUISHED, MULTIPLEX NUCLEIC ACID ANALYSIS OF BIOLOGICAL SPECIMENS

CROSS-REFERENCE TO RELATED APPLICATIONS

This application is a continuation of U.S. patent application Ser. No. 17/834,474, filed on Jun. 7, 2022, which is a continuation of U.S. patent application Ser. No. 17/693,116, filed on Mar. 11, 2022 (issued as U.S. Pat. No. 11,390,912), which is a continuation of U.S. patent application Ser. No. 17/479,718, filed on Sep. 20, 2021 (issued as U.S. Pat. No. 11,299,774), which is a continuation of U.S. patent application Ser. No. 17/237,670, filed on Apr. 22, 2021 (issued as U.S. Pat. No. 11,162,132), which is a continuation of U.S. patent application Ser. No. 17/011,923, filed on Sep. 3, 2020, which is a divisional of U.S. patent application Ser. No. 15/565,637, filed on Nov. 15, 2018 (issued as U.S. Pat. No. 10,774,374), which is a § 371 of International Patent Application No. PCT/EP2016/057355, filed on Apr. 4, 2016, which claims the benefit of U.S. Provisional Patent Application No. 62/145,874, filed on Apr. 10, 2015.

BACKGROUND

One of every four men will die of cancer. Further statistics from the American Cancer Society predict that one of every five women will suffer the same fate. Treatments are available for many cancers. However, success for most relies on early detection.

Cancer is now said to be a disease of the genome. Many oncologists and cancer researchers hope that advances in genomic analysis tools will provide early detection and a path to treatment. However, these tools are more prominent in research labs having not yet matured to the level of being readily available to the vast majority of oncologists. Improvements are needed.

It has been said that at the time of diagnosis, all cancer patients are mosaics. They are mosaics because they have at least two distinct genomes: the genome they were born with, and the genome that they unwillingly acquired via cancer. Furthermore, as tumors grow, distinct populations of cancer cells become apparent. Leading to even more complex mosaics within the tumor. This cancer cell heterogeneity often results in subpopulations of cells that respond differently to cancer therapies. The end result is often an initial positive response of one subpopulation of cells, resulting in the observation of the patient's tumor shrinking, only to be followed by regrowth of tumor tissue, and in some cases metastasis. Despite early detection of the tumor, an inability to identify the subpopulation of cells that are resistant to the treatment can result in loss of time needed to treat an aggressive cancer. This creates adverse consequences for the patient both emotionally and physically.

There is a need for genomic tools that can distinguish subpopulations of cancer cells in tumors. The present disclosure addresses this need and provides other advantages as well.

BRIEF SUMMARY

The present disclosure provides a method for spatially tagging nucleic acids of a biological specimen. The method can include steps of (a) providing a solid support comprising a plurality of different nucleic acid probes that are randomly located on the solid support, wherein the different nucleic acid probes each includes a barcode sequence that is different from the barcode sequence of other randomly located probes on the solid support; (b) performing a nucleic acid detection reaction on the solid support to locate the barcode sequences on the solid support; (c) contacting a biological specimen with the solid support that has the randomly located probes; (d) hybridizing the randomly located probes to target nucleic acids from portions of the biological specimen that are proximal to the randomly located probes; and (e) modifying the randomly located probes that are hybridized to the target nucleic acids, thereby producing modified probes that include the barcode sequences and a target specific modification, thereby spatially tagging the nucleic acids of the biological specimen.

This disclosure further provides a method for spatially tagging nucleic acids of a biological specimen, the method including steps of (a) attaching different nucleic acid probes to a solid support to produce randomly located probes on the solid support, wherein the different nucleic acid probes each includes a barcode sequence, and wherein each of the randomly located probes includes different barcode sequences from other randomly located probes on the solid support; (b) performing a nucleic acid detection reaction on the solid support to determine the barcode sequences of the randomly located probes on the solid support; (c) contacting a biological specimen with the solid support that has the randomly located probes; (d) hybridizing the randomly located probes to target nucleic acids from portions of the biological specimen that are proximal to the randomly located probes; and (e) extending the randomly located probes to produce extended probes that include the barcode sequences and sequences from the target nucleic acids, thereby spatially tagging the nucleic acids of the biological specimen.

Also provided is a method for spatially tagging nucleic acids of a biological specimen that includes the steps of (a) providing a plurality of nucleic acid primers attached to a solid support, wherein the nucleic acid primers in the plurality include a universal primer sequence that is common to the nucleic acid primers in the plurality; (b) binding a population of nucleic acid probes to the plurality of nucleic acid primers, wherein the nucleic acid probes include a universal primer binding sequence that hybridizes to the universal primer sequence, a target capture sequence and a barcode sequence that differs from barcode sequences of other nucleic acid probes in the population, thereby attaching the different nucleic acid probes at randomly located positions on the solid support; (c) amplifying the different nucleic acid probes by extension of the nucleic acid primers, thereby producing nucleic acid clusters having copies of the barcode sequence and target capture sequence at the randomly located positions on the solid support; (d) performing a sequencing reaction to determine the barcode sequences at the randomly located positions on the solid support; (e) contacting a biological specimen with the nucleic acid clusters on the solid support; (f) hybridizing the target capture sequences of the clusters to target nucleic acids from portions of the biological specimen that are proximal to the clusters; and (g) extending the target capture sequences to produce extended probes that include sequences from the target nucleic acids and the copies of the barcode sequences, thereby tagging the nucleic acids of the biological specimen.

This disclosure further provides a method for spatially tagging nucleic acids of a biological specimen, the method including steps of (a) providing an array of beads on a solid support, wherein different nucleic acid probes are attached to different beads in the array, wherein the different nucleic acid probes each include a barcode sequence, wherein each bead includes a different barcode sequence from other beads on the solid support, and wherein each of the different nucleic acid probes includes a target capture sequence; (b) performing a decoder probe hybridization reaction on the solid support to determine the barcode sequences at the randomly located probes on the solid support; (c) contacting a biological specimen with the array of beads; (d) hybridizing the different nucleic acid probes to target nucleic acids from portions of the biological specimen that are proximal to the beads; and (e) extending the different nucleic acid probes to produce extended probes that include sequences from the target nucleic acids and the barcode sequences, thereby tagging the nucleic acids of the biological specimen.

BRIEF DESCRIPTION OF THE DRAWINGS

FIG. 3 shows sequencing metrics of the flow cell described in Example 1 and shown in FIG. 2.

DETAILED DESCRIPTION

Figure 1A:
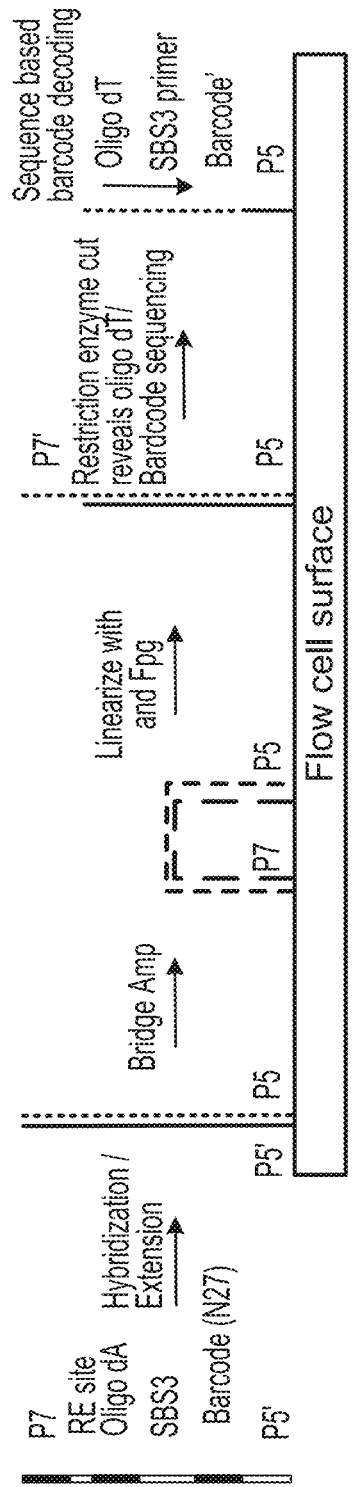
FIG. 1A shows a diagrammatic representation of steps and reagents that can be used to generate barcoded oligo dT probes on an Illumina flow cell, create extended barcoded probes having mRNA sequences and releasing the extended probes from the flow cell.

The present disclosure provides compositions, apparatus and methods for preserving spatial information when performing multiplex nucleic acid analyses of biological specimens. A variety of tools are available for multiplex nucleic acid analyses including, for example, nucleic acid microarrays and so-called "next generation" sequencing platforms. Such tools allow for parallel detection of very large and complex collections of nucleic acids, including for example, DNA collections that represent all or nearly all of the genetic material of an organism (i.e. the 'genome'), RNA (or cDNA) collections that represent all or nearly all of the complement of expressed genes (i.e. the 'transcriptome') for an organism, and in some cases the collections can include several genomes and/or transcriptomes from several different organisms (e.g. a metabolome or biome from a community or ecosystem). Although these tools provide a vast amount of information about what nucleic acid sequences are present in a biological specimen being evaluated, they do not inherently distinguish where any particular nucleic acid resided in the biological specimen. Indeed the vast majority of samples applied to multiplex nucleic acid analysis tools are homogenates derived from mixtures of many different cells from a biological specimen. As a result, spatial information is lost and the results obtained from these tools constitute an average transcriptome or average genome for the specimen, important differences between individual cells being lost.

In particular embodiments, the present disclosure provides new and useful modifications to existing multiplex nucleic acid analysis tools to allow for the preservation of spatial information for biological specimens from which the nucleic acids are obtained. For example, solid supports that are usually used for multiplex sequencing-by-synthesis (SBS) techniques can be modified for use in capturing and spatially tagging nucleic acids from a biological specimen. In an alternative example, arrays of beads, such as those used for genotyping or gene expression analysis, can be used for capturing and spatially tagging nucleic acids from a biological specimen. As set forth in examples below, the solid supports used for an SBS or BeadArray™ platform commercialized by Illumina (San Diego, Calif.) can be modified for spatial tagging. However, it will be understood that any of a variety of solid supports can be made and used in accordance with the teaching herein. The spatially tagged nucleic acids can be removed from the solid support, pooled together and attached to a second solid support for detection in any of a variety of multiplex nucleic acid analysis systems including, for example, a sequencing platform or microarray platform set forth herein.

The spatial information provided by a method, composition or apparatus herein can include, for example, the location of one or more cells in a tissue (or other specimen) that has a particular allele at one or more locus (e.g. a genotype), has a particular structural variation in the genome (e.g. fusion, insertion, deletion, rearrangement etc.), has a particular epigenetic signature (e.g. methylation), expresses a particular gene, expresses a particular allele of a gene, expresses a particular splice variant of a gene or the like. In addition to identifying nucleic acids according to their spatial location in a biological specimen, a method, composition or apparatus of the present disclosure can be used to quantify one or more nucleic acids according to spatial location. For example, the spatial information for one or more cells in a tissue (or other specimen) can include the amount of a particular allele or chromosomal region in a genome (e.g. ploidy); the amount of epigenetic modification of a genetic locus (e.g. methylation); expression level for a particular gene, allele or splice variant; or the like. The amounts can be absolute amounts or relative amounts in accordance with similar measurements obtained in the art for mixed or non-spatially tagged samples.

A method set forth herein can be used for localized detection of a nucleic acid in a biological specimen. In some embodiments, a method can be used for identifying or characterizing all of the transcriptome or genome of a biological specimen. Alternatively, a method can be used to identify or characterize only a part of a specimen's transcriptome or genome. A subset of transcripts or genes evaluated in a method herein can be related to a particular disease or condition.

A method set forth herein can be used for localized or spatial detection of nucleic acids, whether DNA or RNA, in a biological specimen. Thus one or more RNA or DNA molecules can be located with respect to its native position or location within a cell or tissue or other biological specimen. For example, one or more nucleic acids can be localized to a cell or group of adjacent cells, or type of cell, or to particular regions of areas within a tissue sample. The native location or position of individual RNA or DNA molecules can be determined using a method, apparatus or composition of the present disclosure.

Terms used herein will be understood to take on their ordinary meaning in the relevant art unless specified otherwise. Several terms used herein and their meanings are set forth below.

As used herein, the term "amplicon," when used in reference to a nucleic acid, means the product of copying the nucleic acid, wherein the product has a nucleotide sequence that is the same as or complementary to at least a portion of the nucleotide sequence of the nucleic acid. An amplicon can be produced by any of a variety of amplification methods that use the nucleic acid, or an amplicon thereof, as a template including, for example, polymerase extension, polymerase chain reaction (PCR), rolling circle amplification (RCA), multiple displacement amplification (MDA), ligation extension, or ligation chain reaction. An amplicon can be a nucleic acid molecule having a single copy of a particular nucleotide sequence (e.g. a PCR product) or multiple copies of the nucleotide sequence (e.g. a concatameric product of RCA). A first amplicon of a target nucleic acid is typically a complimentary copy. Subsequent amplicons are copies that are created, after generation of the first amplicon, from the target nucleic acid or from the first amplicon. A subsequent amplicon can have a sequence that is substantially complementary to the target nucleic acid or substantially identical to the target nucleic acid.

As used herein, the term "array" refers to a population of features or sites that can be differentiated from each other according to relative location. Different molecules that are at different sites of an array can be differentiated from each other according to the locations of the sites in the array. An individual site of an array can include one or more molecules of a particular type. For example, a site can include a single target nucleic acid molecule having a particular sequence or a site can include several nucleic acid molecules having the same sequence (and/or complementary sequence, thereof). The sites of an array can be different features in a substrate, beads (or other particles) in or on a substrate, projections from a substrate, ridges on a substrate or channels in a substrate. The sites of an array can be separate substrates each bearing a different molecule. Different molecules attached to separate substrates can be identified according to the locations of the substrates on a surface to which the substrates are associated or according to the locations of the substrates in a liquid or gel. Exemplary arrays in which separate substrates are located on a surface include, without limitation, those having beads in wells.

As used herein, the term "attached" refers to the state of two things being joined, fastened, adhered, connected or bound to each other. For example, an analyte, such as a nucleic acid, can be attached to a material, such as a gel or solid support, by a covalent or non-covalent bond. A covalent bond is characterized by the sharing of pairs of electrons between atoms. A non-covalent bond is a chemical bond that does not involve the sharing of pairs of electrons and can include, for example, hydrogen bonds, ionic bonds, van der Waals forces, hydrophilic interactions and hydrophobic interactions.

As used herein, the term "barcode sequence" is intended to mean a series of nucleotides in a nucleic acid that can be used to identify the nucleic acid, a characteristic of the nucleic acid, or a manipulation that has been carried out on the nucleic acid. The barcode sequence can be a naturally occurring sequence or a sequence that does not occur naturally in the organism from which the barcoded nucleic acid was obtained. A barcode sequence can be unique to a single nucleic acid species in a population or a barcode sequence can be shared by several different nucleic acid species in a population. For example, each nucleic acid probe in a population can include different barcode sequences from all other nucleic acid probes in the population. Alternatively, each nucleic acid probe in a population can include different barcode sequences from some or most other nucleic acid probes in a population. For example, each probe in a population can have a barcode that is present for several different probes in the population even though the probes with the common barcode differ from each other at other sequence regions along their length. In particular embodiments, one or more barcode sequences that are used with a biological specimen are not present in the genome, transcriptome or other nucleic acids of the biological specimen. For example, barcode sequences can have less than 80%, 70%, 60%, 50% or 40% sequence identity to the nucleic acid sequences in a particular biological specimen.

As used herein, the term "biological specimen" is intended to mean one or more cell, tissue, organism or portion thereof. A biological specimen can be obtained from any of a variety of organisms. Exemplary organisms include, but are not limited to, a mammal such as a rodent, mouse, rat, rabbit, guinea pig, ungulate, horse, sheep, pig, goat, cow, cat, dog, primate (i.e. human or non-human primate); a plant such as *Arabidopsis thaliana*, corn, sorghum, oat, wheat, rice, canola, or soybean; an algae such as *Chlamydomonas reinhardtii*; a nematode such as *Caenorhabditis elegans*; an insect such as *Drosophila melanogaster*, mosquito, fruit fly, honey bee or spider; a fish such as zebrafish; a reptile; an amphibian such as a frog or *Xenopus laevis*; a *Dictyostelium discoideum*; a fungi such as *Pneumocystis carinii*, *Takifugu rubripes*, yeast, *Saccharamoyces cerevisiae* or *Schizosaccharomyces pombe*; or a *Plasmodium falciparum*. Target nucleic acids can also be derived from a prokaryote such as a bacterium, *Escherichia coli*, Staphylococci or *Mycoplasma pneumoniae*; an archae; a virus such as Hepatitis C virus or human immunodeficiency virus; or a viroid. Specimens can be derived from a homogeneous culture or population of the above organisms or alternatively from a collection of several different organisms, for example, in a community or ecosystem.

As used herein, the term "cleavage site" is intended to mean a location in a nucleic acid molecule that is susceptible to bond breakage. The location can be specific to a particular chemical, enzymatic or physical process that results in bond breakage. For example, the location can be a nucleotide that is abasic or a nucleotide that has a base that is susceptible to being removed to create an abasic site. Examples of nucleotides that are susceptible to being removed include uracil and 8-oxo-guanine as set forth in further detail herein below. The location can also be at or near a recognition sequence for a restriction endonuclease such as a nicking enzyme.

As used herein, the term "cluster," when used in reference to nucleic acids, refers to a population of the nucleic acids that is attached to a solid support to form a feature or site. The nucleic acids are generally members of a single species, thereby forming a monoclonal cluster. A "monoclonal population" of nucleic acids is a population that is homogeneous with respect to a particular nucleotide sequence. Clusters need not be monoclonal. Rather, for some applications, a cluster can be predominantly populated with amplicons from a first nucleic acid and can also have a low level of contaminating amplicons from a second nucleic acid. For example, when an array of clusters is to be used in a detection application, an acceptable level of contamination would be a level that does not impact signal to noise or resolution of the detection technique in an unacceptable way. Accordingly, apparent clonality will generally be relevant to a particular use or application of an array made by the methods set forth herein. Exemplary levels of contamination that can be acceptable at an individual cluster include, but are not limited to, at most 0.1%, 0.5%, 1%, 5%, 10%, 5 25%, or 35% contaminating amplicons. The nucleic acids in a cluster are generally covalently attached to a solid support, for example, via their 5' ends, but in some cases other attachment means are possible. The nucleic acids in a cluster can be single stranded or double stranded. In some but not all embodiments, clusters are made by a solid-phase amplification method known as bridge amplification. Exemplary configurations for clusters and methods for their production are set forth, for example, in U.S. Pat. No. 5,641,658; U.S. Patent Publ. No. 2002/0055100; U.S. Pat. No. 7,115,400; U.S. Patent Publ. No. 2004/0096853; U.S. Patent Publ. No. 2004/0002090; U.S. Patent Publ. No. 2007/0128624; and U.S. Patent Publ. No. 2008/0009420, each of which is incorporated herein by reference.

As used herein, the term "different", when used in reference to nucleic acids, means that the nucleic acids have nucleotide sequences that are not the same as each other. Two or more nucleic acids can have nucleotide sequences that are different along their entire length. Alternatively, two or more nucleic acids can have nucleotide sequences that are different along a substantial portion of their length. For example, two or more nucleic acids can have target nucleotide sequence portions that are different for the two or more molecules while also having a universal sequence portion that is the same on the two or more molecules. Two beads can be different from each other by virtue of being attached to different nucleic acids.

As used herein, the term "each," when used in reference to a collection of items, is intended to identify an individual item in the collection but does not necessarily refer to every item in the collection. Exceptions can occur if explicit disclosure or context clearly dictates otherwise.

As used herein, the term "extend," when used in reference to a nucleic acid, is intended to mean addition of at least one nucleotide or oligonucleotide to the nucleic acid. In particular embodiments one or more nucleotides can be added to the 3' end of a nucleic acid, for example, via polymerase catalysis (e.g. DNA polymerase, RNA polymerase or reverse transcriptase). Chemical or enzymatic methods can be used to add one or more nucleotide to the 3' or 5' end of a nucleic acid. One or more oligonucleotides can be added to the 3' or 5' end of a nucleic acid, for example, via chemical or enzymatic (e.g. ligase catalysis) methods. A nucleic acid can be extended in a template directed manner, whereby the product of extension is complementary to a template nucleic acid that is hybridized to the nucleic acid that is extended.

As used herein, the term "feature" means a location in an array for a particular species of molecule. A feature can contain only a single molecule or it can contain a population of several molecules of the same species. Features of an array are typically discrete. The discrete features can be contiguous or they can have spaces between each other. The size of the features and/or spacing between the features can vary such that arrays can be high density, medium density or lower density. High density arrays are characterized as having sites separated by less than about 15 µm. Medium density arrays have sites separated by about 15 to 30 µm, while low density arrays have sites separated by greater than 30 µm. An array useful herein can have, for example, sites that are separated by less than 100 µm, 50 µm, 10 µm, 5 µm, 1 µm, or 0.5 µm. An apparatus or method of the present disclosure can be used to detect an array at a resolution sufficient to distinguish sites at the above densities or density ranges.

As used herein, the term "fluidic mixture" is intended to mean two or more different items that are simultaneously present in a solution. Typically, the two or more items are freely diffusible in the solution. The two or more items can be different types of items (e.g. a nucleic acid and a protein which are different types of molecules) or they can be different species of the same type of items (e.g. two nucleic acid molecules having different sequences). Exemplary items that can be in a fluidic mixture include, but are not limited to, molecules, cells or beads.

As used herein, the term "flow cell" is intended to mean a vessel having a chamber where a reaction can be carried out, an inlet for delivering reagents to the chamber and an outlet for removing reagents from the chamber. In some embodiments the chamber is configured for detection of the reaction that occurs in the chamber. For example, the chamber can include one or more transparent surfaces allowing optical detection of biological specimens, optically labeled molecules, or the like in the chamber. Exemplary flow cells include, but are not limited to those used in a nucleic acid sequencing apparatus such as flow cells for the Genome Analyzer®, MiSeq®, NextSeq® or HiSeq® platforms commercialized by Illumina, Inc. (San Diego, Calif.); or for the SOLiD™ or Ion Torrent™ sequencing platform commercialized by Life Technologies (Carlsbad, Calif.). Exemplary flow cells and methods for their manufacture and use are also described, for example, in WO 2014/142841 A1; U.S. Pat. App. Pub. No. 2010/0111768 A1 and U.S. Pat. No. 8,951,781, each of which is incorporated herein by reference.

As used herein, the term "gel" is intended to mean a semi-rigid material that is permeable to liquids and gases. Typically, gel material can swell when liquid is taken up and can contract when liquid is removed by drying. Exemplary gels include, but are not limited to those having a colloidal structure, such as agarose; polymer mesh structure, such as gelatin; or cross-linked polymer structure, such as polyacrylamide, SFA (see, for example, US Pat. App. Pub. No. 2011/0059865 A1, which is incorporated herein by reference) or PAZAM (see, for example, US Pat. App. Publ. No. 2014/0079923 A1, which is incorporated herein by reference).

Particularly useful gel material will conform to the shape of a well or other concave feature where it resides.

As used herein, the terms "nucleic acid" and "nucleotide" are intended to be consistent with their use in the art and to include naturally occurring species or functional analogs thereof. Particularly useful functional analogs of nucleic acids are capable of hybridizing to a nucleic acid in a sequence specific fashion or capable of being used as a template for replication of a particular nucleotide sequence. Naturally occurring nucleic acids generally have a backbone containing phosphodiester bonds. An analog structure can have an alternate backbone linkage including any of a variety of those known in the art. Naturally occurring nucleic acids generally have a deoxyribose sugar (e.g. found in deoxyribonucleic acid (DNA)) or a ribose sugar (e.g. found in ribonucleic acid (RNA)). A nucleic acid can contain nucleotides having any of a variety of analogs of these sugar moieties that are known in the art. A nucleic acid can include native or non-native nucleotides. In this regard, a native deoxyribonucleic acid can have one or more bases selected from the group consisting of adenine, thymine, cytosine or guanine and a ribonucleic acid can have one or more bases selected from the group consisting of uracil, adenine, cytosine or guanine. Useful non-native bases that can be included in a nucleic acid or nucleotide are known in the art. The terms "probe" or "target," when used in reference to a nucleic acid or sequence of a nucleic acid, are intended as semantic identifiers for the nucleic acid or sequence in the context of a method or composition set forth herein and does not necessarily limit the structure or function of the nucleic acid or sequence beyond what is otherwise explicitly indicated. The terms "probe" and "target" can be similarly applied to other analytes such as proteins, small molecules, cells or the like.

As used herein, the term "pitch," when used in reference to features of an array, is intended to refer to the center-to-center spacing for adjacent features. A pattern of features can be characterized in terms of average pitch. The pattern can be ordered such that the coefficient of variation around the average pitch is small or the pattern can be random in which case the coefficient of variation can be relatively large. In either case, the average pitch can be, for example, at least about 10 nm, 0.1 µm, 0.5 µm, 1 µm, 5 µm, 10 µm, 100 µm or more. Alternatively or additionally, the average pitch can be, for example, at most about 100 µm, 10 µm, 5 µm, 1 µm, 0.5 µm 0.1 µm or less. Of course, the average pitch for a particular pattern of features can be between one of the lower values and one of the upper values selected from the ranges above.

As used herein, the term "poly T or poly A," when used in reference to a nucleic acid sequence, is intended to mean a series of two or more thiamine (T) or adenine (A) bases, respectively. A poly T or poly A can include at least about 2, 5, 8, 10, 12, 15, 18, 20 or more of the T or A bases, respectively. Alternatively or additionally, a poly T or poly A can include at most about, 30, 20, 18, 15, 12, 10, 8, 5 or 2 of the T or A bases, respectively.

As used herein, the term "random" can be used to refer to the spatial arrangement or composition of locations on a surface. For example, there are at least two types of order for an array described herein, the first relating to the spacing and relative location of features (also called "sites") and the second relating to identity or predetermined knowledge of the particular species of molecule that is present at a particular feature. Accordingly, features of an array can be randomly spaced such that nearest neighbor features have variable spacing between each other. Alternatively, the spacing between features can be ordered, for example, forming a regular pattern such as a rectilinear grid or hexagonal grid.

In another respect, features of an array can be random with respect to the identity or predetermined knowledge of the species of analyte (e.g. nucleic acid of a particular sequence) that occupies each feature independent of whether spacing produces a random pattern or ordered pattern. An array set forth herein can be ordered in one respect and random in another. For example, in some embodiments set forth herein a surface is contacted with a population of nucleic acids under conditions where the nucleic acids attach at sites that are ordered with respect to their relative locations but 'randomly located' with respect to knowledge of the sequence for the nucleic acid species present at any particular site. Reference to "randomly distributing" nucleic acids at locations on a surface is intended to refer to the absence of knowledge or absence of predetermination regarding which nucleic acid will be captured at which location (regardless of whether the locations are arranged in an ordered pattern or not).

As used herein, the term "solid support" refers to a rigid substrate that is insoluble in aqueous liquid. The substrate can be non-porous or porous. The substrate can optionally be capable of taking up a liquid (e.g. due to porosity) but will typically be sufficiently rigid that the substrate does not swell substantially when taking up the liquid and does not contract substantially when the liquid is removed by drying. A nonporous solid support is generally impermeable to liquids or gases. Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefins, polyimides etc.), nylon, ceramics, resins, Zeonor, silica or silica-based materials including silicon and modified silicon, carbon, metals, inorganic glasses, optical fiber bundles, and polymers. Particularly useful solid supports for some embodiments are located within a flow cell apparatus. Exemplary flow cells are set forth in further detail herein.

As used herein, the term "spatial tag" is intended to mean a nucleic acid having a sequence that is indicative of a location. Typically, the nucleic acid is a synthetic molecule having a sequence that is not found in one or more biological specimen that will be used with the nucleic acid. However, in some embodiments the nucleic acid molecule can be naturally derived or the sequence of the nucleic acid can be naturally occurring, for example, in a biological specimen that is used with the nucleic acid. The location indicated by a spatial tag can be a location in or on a biological specimen, in or on a solid support or a combination thereof. A barcode sequence can function as a spatial tag.

As used herein, the term "tissue" is intended to mean an aggregation of cells, and, optionally, intercellular matter. Typically the cells in a tissue are not free floating in solution and instead are attached to each other to form a multicellular structure. Exemplary tissue types include muscle, nerve, epidermal and connective tissues.

As used herein, the term "universal sequence" refers to a series of nucleotides that is common to two or more nucleic acid molecules even if the molecules also have regions of sequence that differ from each other. A universal sequence that is present in different members of a collection of molecules can allow capture of multiple different nucleic acids using a population of universal capture nucleic acids that are complementary to the universal sequence. Similarly, a universal sequence present in different members of a collection of molecules can allow the replication or amplification of multiple different nucleic acids using a population of universal primers that are complementary to the universal sequence. Thus, a universal capture nucleic acid or a universal primer includes a sequence that can hybridize specifically to a universal sequence. Target nucleic acid molecules may be modified to attach universal adapters, for example, at one or both ends of the different target sequences.

The embodiments set forth below and recited in the claims can be understood in view of the above definitions.

The present disclosure provides a method for spatially tagging nucleic acids of a biological specimen. The method can include the steps of (a) attaching different nucleic acid probes to a solid support to produce randomly located probes on the solid support, wherein the different nucleic acid probes each includes a barcode sequence, and wherein each of the randomly located probes includes different barcode sequences from other randomly located probes on the solid support; (b) performing a nucleic acid detection reaction on the solid support to determine the barcode sequences of the randomly located probes on the solid support; (c) contacting a biological specimen with the solid support that has the randomly located probes; (d) hybridizing the randomly located probes to target nucleic acids from portions of the biological specimen that are proximal to the randomly located probes; and (e) extending the randomly located probes to produce extended probes that include the barcode sequences and sequences from the target nucleic acids, thereby spatially tagging the nucleic acids of the biological specimen.

Any of a variety of solid supports can be used in a method, composition or apparatus of the present disclosure. Particularly useful solid supports are those used for nucleic acid arrays. Examples include glass, modified glass, functionalized glass, inorganic glasses, microspheres (e.g. inert and/or magnetic particles), plastics, polysaccharides, nylon, nitrocellulose, ceramics, resins, silica, silica-based materials, carbon, metals, an optical fiber or optical fiber bundles, polymers and multiwell (e.g. microtiter) plates. Exemplary plastics include acrylics, polystyrene, copolymers of styrene and other materials, polypropylene, polyethylene, polybutylene, polyurethanes and Teflon™. Exemplary silica-based materials include silicon and various forms of modified silicon.

In particular embodiments, a solid support can be within or part of a vessel such as a well, tube, channel, cuvette, Petri plate, bottle or the like. A particularly useful vessel is a flow-cell, for example, as described in WO 2014/142841 A1; U.S. Pat. App. Pub. No. 2010/0111768 A1 and U.S. Pat. No. 8,951,781 or Bentley et al., Nature 456:53-59 (2008), each of which is incorporated herein by reference. Exemplary flow-cells are those that are commercially available from Illumina, Inc. (San Diego, Calif.) for use with a sequencing platform such as a Genome Analyzer®, MiSeq®, NextSeq® or HiSeq® platform. Another particularly useful vessel is a well in a multiwell plate or microtiter plate.

Optionally, a solid support can include a gel coating. Attachment of nucleic acids to a solid support via a gel is exemplified by flow cells available commercially from Illumina Inc. (San Diego, Calif.) or described in US Pat. App. Pub. Nos. 2011/0059865 A1, 2014/0079923 A1, or 2015/0005447 A1; or PCT Publ. No. WO 2008/093098, each of which is incorporated herein by reference. Exemplary gels that can be used in the methods and apparatus set forth herein include, but are not limited to, those having a colloidal structure, such as agarose; polymer mesh structure, such as gelatin; or cross-linked polymer structure, such as polyacrylamide, SFA (see, for example, US Pat. App. Publ. No. 2011/0059865 A1, which is incorporated herein by reference) or PAZAM (see, for example, US Pat. App. Publ. Nos. 2014/0079923A1, or 2015/0005447 A1, each of which is incorporated herein by reference).

In some embodiments, a solid support can be configured as an array of features to which nucleic acids can be attached. The features can be present in any of a variety of desired formats. For example, the features can be wells, pits, channels, ridges, raised regions, pegs, posts or the like. In some embodiments, the features can contain beads. However, in particular embodiments the features need not contain a bead or particle. Exemplary features include wells that are present in substrates used for commercial sequencing platforms sold by 454 LifeSciences (a subsidiary of Roche, Basel Switzerland) or Ion Torrent (a subsidiary of Life Technologies, Carlsbad Calif.). Other substrates having wells include, for example, etched fiber optics and other substrates described in U.S. Pat. Nos. 6,266,459; 6,355,431; 6,770,441; 6,859,570; 6,210,891; 6,258,568; 6,274,320; us Pat app. Publ. Nos. 2009/0026082 A1; 2009/0127589 A1; 2010/0137143 A1; 2010/0282617 A1 or PCT Publication No. WO 00/63437, each of which is incorporated herein by reference. In some embodiments, wells of a substrate can include gel material (with or without beads) as set forth in US Pat. App. Publ. No. 2014/0243224 A1, which is incorporated herein by reference.

The features on a solid support can be metal features on a non-metallic surface such as glass, plastic or other materials exemplified above. A metal layer can be deposited on a surface using methods known in the art such as wet plasma etching, dry plasma etching, atomic layer deposition, ion beam etching, chemical vapor deposition, vacuum sputtering or the like. Any of a variety of commercial instruments can be used as appropriate including, for example, the FlexAL®, OpAL®, Ionfab 300Plus®, or Optofab 3000® systems (Oxford Instruments, UK). A metal layer can also be deposited by e-beam evaporation or sputtering as set forth in Thornton, Ann. Rev. Mater. Sci. 7:239-60 (1977), which is incorporated herein by reference. Metal layer deposition techniques, such as those exemplified above, can be combined with photolithography techniques to create metal regions or patches on a surface. Exemplary methods for combining metal layer deposition techniques and photolithography techniques are provided in U.S. Pat. No. 8,895,249 or US Pat App. Pub. No. 2014/0243224 A1, each of which is incorporated herein by reference.

Features can appear on a solid support as a grid of spots or patches. The features can be located in a repeating pattern or in an irregular, non-repeating pattern. Particularly useful repeating patterns are hexagonal patterns, rectilinear patterns, grid patterns, patterns having reflective symmetry, patterns having rotational symmetry, or the like. Asymmetric patterns can also be useful. The pitch can be the same between different pairs of nearest neighbor features or the pitch can vary between different pairs of nearest neighbor features.

High density arrays are characterized as having average pitch of less than about 15 µm. Medium density arrays have average pitch of about 15 to 30 µm, while low density arrays have average pitch greater than 30 µm. An array useful in the invention can have average pitch that is less than 100 µm, 50 µm, 10 µm, 5 µm, 1 µm or 0.5 µm. The average pitch values and ranges set forth above or elsewhere herein are intended to be applicable to ordered arrays or random arrays.

In particular embodiments, features on a solid support can each have an area that is larger than about 100 nm2, 250 nm2, 500 nm2, 1 µm2, 2.5 µm2, 5 µm2, 10 µm2, 100 µm2, or 500 µm2. Alternatively or additionally, features can each have an area that is smaller than about 1 mm2, 500 µm2, 100 µm2, 25 µm2, 10 µm2, 5 µm2, 1 µm2, 500 nm2, or 100 nm2. The above ranges can describe the apparent area of a bead or other particle on a solid support when viewed or imaged from above.

In particular embodiments, a solid support can include a collection of beads or other particles. The particles can be suspended in a solution or they can be located on the surface of a substrate. Examples of arrays having beads located on a surface include those wherein beads are located in wells such as a BeadChip array (Illumina Inc., San Diego Calif.), substrates used in sequencing platforms from 454 Life-Sciences (a subsidiary of Roche, Basel Switzerland) or substrates used in sequencing platforms from Ion Torrent (a subsidiary of Life Technologies, Carlsbad Calif.). Other solid supports having beads located on a surface are described in U.S. Pat. Nos. 6,266,459; 6,355,431; 6,770,441; 6,859,570; 6,210,891; 6,258,568; or 6,274,320; US Pat. App. Publ. Nos. 2009/0026082 A1; 2009/0127589 A1; 2010/0137143 A1; or 2010/0282617 A1 or PCT Publication No. WO 00/63437, each of which is incorporated herein by reference. Several of the above references describe methods for attaching nucleic acid probes to beads prior to loading the beads in or on a solid support. As such, the collection of beads can include different beads each having a unique probe attached. It will however, be understood that the beads can be made to include universal primers, and the beads can then be loaded onto an array, thereby forming universal arrays for use in a method set forth herein.

As set forth previously herein, the solid supports typically used for bead arrays can be used without beads. For example, nucleic acids, such as probes or primers can be attached directly to the wells or to gel material in wells. Thus, the above references are illustrative of materials, compositions or apparatus that can be modified for use in the methods and compositions set forth herein.

Accordingly, a solid support used in a method set forth herein can include an array of beads, wherein different nucleic acid probes are attached to different beads in the array. In this embodiment, each bead can be attached to a different nucleic acid probe and the beads can be randomly distributed on the solid support in order to effectively attach the different nucleic acid probes to the solid support.

Optionally, the solid support can include wells having dimensions that accommodate no more than a single bead. In such a configuration, the beads may be attached to the wells due to forces resulting from the fit of the beads in the wells. It is also possible to use attachment chemistries or adhesives to hold the beads in the wells.

Nucleic acid probes that are attached to beads can include barcode sequences. A population of the beads can be configured such that each bead is attached to only one type of barcode and many different beads each with a different barcode are present in the population. In this embodiment, randomly distributing the beads to a solid support will result in randomly locating the nucleic acid probes (and their respective barcode sequences) on the solid support. In some cases there can be multiple beads with the same barcode sequence such that there is redundancy in the population. Randomly distributing a redundant population of beads on a solid support that has a capacity that is greater than the number of unique barcodes in the bead population will result in redundancy of barcodes on the solid support.

Alternatively, the number of different barcodes in a population of beads can exceed the capacity of the solid support in order to produce an array that is not redundant with respect to the population of barcodes on the solid support. The capacity of the solid support will be determined in some embodiments by the number of features (e.g. single-bead occupancy wells) that attach or otherwise accommodate a bead.

A solid support can include, or can be made by the methods set forth herein to attach, a plurality of different nucleic acid probes. For example, a solid support can include at least 10, 100, 1×103, 1×104, 1×105, 1×106, 1×107, 1×108, 1×109 or more different probes. Alternatively or additionally, a solid support can include at most 1×109, 1×108, 1×107, 1×106, 1×105, 1×104, 1×103, 100, or fewer different probes. It will be understood that each of the different probes can be present in several copies, for example, when the probes have been amplified to form a cluster. Thus, the above ranges can describe the number of different nucleic acid clusters on a solid support. It will also be understood that the above ranges can describe the number of different barcodes, target capture sequences, or other sequence elements set forth herein as being unique to particular nucleic acid probes. Alternatively or additionally, the ranges can describe the number of extended probes or modified probes created on a solid support using a method set forth herein.

Features, may be present on a solid support prior to contacting the solid support with nucleic acid probes. For example, in embodiments where probes are attached to a support via hybridization to primers, the primers can be attached at the features, whereas interstitial areas outside of the features substantially lack any of the primers. Nucleic acid probes can be captured at preformed features on a solid support, and optionally amplified on the solid support, using methods set forth in U.S. Pat. Nos. 8,895,249, 8,778,849, or US Pat App. Pub. No. 2014/0243224 A1, each of which is incorporated herein by reference. Alternatively, a solid support may have a lawn of primers or may otherwise lack features. In this case, a feature can be formed by virtue of attachment of a nucleic acid probe on the solid support. Optionally, the captured nucleic acid probe can be amplified on the solid support such that the resulting cluster becomes a feature. Although attachment is exemplified above as capture between a primer and a complementary portion of a probe, it will be understood that capture moieties other than primers can be present at pre-formed features or as a lawn. Other exemplary capture moieties include, but are not limited to, chemical moieties capable of reacting with a nucleic acid probe to create a covalent bond or receptors capable of biding non-covalently to a ligand on a nucleic acid probe.

A step of attaching nucleic acid probes to a solid support can be carried out by providing a fluid that contains a mixture of different nucleic acid probes and contacting this fluidic mixture with the solid support. The contact can result in the fluidic mixture being in contact with a surface to which many different nucleic acid probes from the fluidic mixture will attach. Thus, the probes have random access to the surface (whether the surface has pre-formed features configured to attach the probes or a uniform surface configured for attachment). Accordingly, the probes can be randomly located on the solid support.

The total number and variety of different probes that end up attached to a surface can be selected for a particular application or use. For example, in embodiments where a fluidic mixture of different nucleic acid probes is contacted with a solid support for purposes of attaching the probes to the support, the number of different probe species can exceed the occupancy of the solid support for probes. Thus, the number and variety of different probes that attach to the solid support can be equivalent to the probe occupancy of the solid support. Alternatively, the number and variety of different probe species on the solid support can be less than the occupancy (i.e. there will be redundancy of probe species such that the solid support may contain multiple features having the same probe species). Such redundancy can be achieved, for example, by contacting the solid support with a fluidic mixture that contains a number and variety of probe species that is substantially lower than the probe occupancy of the solid support.

Attachment of the nucleic acid probes can be mediated by hybridization of the nucleic acid probes to complementary primers that are attached to the solid support, chemical bond formation between a reactive moiety on the nucleic acid probe and the solid support (examples are set forth in U.S. Pat. Nos. 8,895,249, 8,778,849, or US Pat App. Pub. No. 2014/0243224 A1, each of which is incorporated herein by reference), affinity interactions of a moiety on the nucleic acid probe with a solid support-bound moiety (e.g. between known receptor-ligand pairs such as streptavidinbiotin, antibody-epitope, lectin-carbohydrate and the like), physical interactions of the nucleic acid probes with the solid support (e.g. hydrogen bonding, ionic forces, van der Waals forces and the like), or other interactions known in the art to attach nucleic acids to surfaces.

In some embodiments, attachment of a nucleic acid probe is non-specific with regard to any sequence differences between the nucleic acid probe and other nucleic acid probes that are or will be attached to the solid support. For example, different probes can have a universal sequence that complements surface-attached primers or the different probes can have a common moiety that mediates attachment to the surface. Alternatively, each of the different probes (or a subpopulation of different probes) can have a unique sequence that complements a unique primer on the solid support or they can have a unique moiety that interacts with one or more different reactive moiety on the solid support. In such cases, the unique primers or unique moieties can, optionally, be attached at predefined locations in order to selectively capture particular probes, or particular types of probes, at the respective predefined locations.

One or more features on a solid support can each include a single molecule of a particular probe. The features can be configured, in some embodiments, to accommodate no more than a single nucleic acid probe molecule. However, whether or not the feature can accommodate more than one nucleic acid probe molecule, the feature may nonetheless include no more than a single nucleic acid probe molecule. Alternatively, an individual feature can include a plurality of nucleic acid probe molecules, for example, an ensemble of nucleic acid probe molecules having the same sequence as each other. In particular embodiments, the ensemble can be produced by amplification from a single nucleic acid probe template to produce amplicons, for example, as a cluster attached to the surface.

A method set forth herein can use any of a variety of amplification techniques. Exemplary techniques that can be used include, but are not limited to, polymerase chain reaction (PCR), rolling circle amplification (RCA), multiple displacement amplification (MDA), or random prime amplification (RPA). In some embodiments the amplification can be carried out in solution, for example, when features of an array are capable of containing amplicons in a volume having a desired capacity. Preferably, an amplification technique used in a method of the present disclosure will be carried out on solid phase. For example, one or more primer species (e.g. universal primers for one or more universal primer binding site present in a nucleic acid probe) can be attached to a solid support. In PCR embodiments, one or both of the primers used for amplification can be attached to a solid support (e.g. via a gel). Formats that utilize two species of primers attached to a solid support are often referred to as bridge amplification because double stranded amplicons form a bridge-like structure between the two surface attached primers that flank the template sequence that has been copied. Exemplary reagents and conditions that can be used for bridge amplification are described, for example, in U.S. Pat. Nos. 5,641,658, 7,115,400, or 8,895, 249; or U.S. Pat. Publ. Nos. 2002/0055100 A1, 2004/0096853 A1, 2004/0002090 A1, 2007/0128624 A1 or 2008/0009420 A1, each of which is incorporated herein by reference. Solid-phase PCR amplification can also be carried out with one of the amplification primers attached to a solid support and the second primer in solution. An exemplary format that uses a combination of a surface attached primer and soluble primer is the format used in emulsion PCR as described, for example, in Dressman et al., Proc. Natl. Acad. Sci. USA 100:8817-8822 (2003), WO 05/010145, or U.S. Pat. App. Publ. Nos. 2005/0130173 A1 or 2005/0064460 A1, each of which is incorporated herein by reference. Emulsion PCR is illustrative of the format and it will be understood that for purposes of the methods set forth herein the use of an emulsion is optional and indeed for several embodiments an emulsion is not used.

RCA techniques can be modified for use in a method of the present disclosure. Exemplary components that can be used in an RCA reaction and principles by which RCA produces amplicons are described, for example, in Lizardi et al., Nat. Genet. 19:225-232 (1998) and US Pat. App. Publ. No. 2007/0099208 A1, each of which is incorporated herein by reference. Primers used for RCA can be in solution or attached to a solid support. The primers can be one or more of the universal primers described herein.

MDA techniques can be modified for use in a method of the present disclosure. Some basic principles and useful conditions for MDA are described, for example, in Dean et al., Proc Natl. Acad. Sci. USA 99:5261-66 (2002); Lage et al., Genome Research 13:294-307 (2003); Walker et al., Molecular Methods for Virus Detection, Academic Press, Inc., 1995; Walker et al., Nucl. Acids Res. 20:1691-96 (1992); U.S. Pat. Nos. 5,455,166; 5,130,238; and 6,214,587, each of which is incorporated herein by reference. Primers used for MDA can be in solution or attached to a solid support at an amplification site. Again, the primers can be one or more of the universal primers described herein.

In particular embodiments a combination of the above-exemplified amplification techniques can be used. For example, RCA and MDA can be used in a combination wherein RCA is used to generate a concatameric amplicon in solution (e.g. using solution-phase primers). The amplicon can then be used as a template for MDA using primers that are attached to a solid support (e.g. universal primers). In this example, amplicons produced after the combined RCA and MDA steps will be attached to the solid support.

Nucleic acid probes that are used in a method set forth herein or present in an apparatus or composition of the present disclosure can include barcode sequences, and for embodiments that include a plurality of different nucleic acid probes, each of the probes can include a different barcode sequence from other probes in the plurality. Barcode sequences can be any of a variety of lengths.

Longer sequences can generally accommodate a larger number and variety of barcodes for a population. Generally, all probes in a plurality will have the same length barcode (albeit with different sequences), but it is also possible to use different length barcodes for different probes. A barcode sequence can be at least 2, 4, 6, 8, 10, 12, 15, 20 or more nucleotides in length. Alternatively or additionally, the length of the barcode sequence can be at most 20, 15, 12, 10, 8, 6, 4 or fewer nucleotides. Examples of barcode sequences that can be used are set forth, for example in, US Pat. App. Publ. No. 2014/0342921 A1 and U.S. Pat. No. 8,460,865, each of which is incorporated herein by reference.

A method of the present disclosure can include a step of performing a nucleic acid detection reaction on a solid support to determine barcode sequences of nucleic acid probes that are located on the solid support. In many embodiments the probes are randomly located on the solid support and the nucleic acid detection reaction provides information to locate each of the different probes. Exemplary nucleic acid detection methods include, but are not limited to nucleic acid sequencing of a probe, hybridization of nucleic acids to a probe, ligation of nucleic acids that are hybridized to a probe, extension of nucleic acids that are hybridized to a probe, extension of a first nucleic acid that is hybridized to a probe followed by ligation of the extended nucleic acid to a second nucleic acid that is hybridized to the probe, or other methods known in the art such as those set forth in U.S. Pat. No. 8,288,103 or 8,486,625, each of which is incorporated herein by reference.

Sequencing techniques, such as sequencing-by-synthesis (SBS) techniques, are a particularly useful method for determining barcode sequences. SBS can be carried out as follows. To initiate a first SBS cycle, one or more labeled nucleotides, DNA polymerase, SBS primers etc., can be contacted with one or more features on a solid support (e.g. feature(s) where nucleic acid probes are attached to the solid support). Those features where SBS primer extension causes a labeled nucleotide to be incorporated can be detected. Optionally, the nucleotides can include a reversible termination moiety that terminates further primer extension once a nucleotide has been added to the SBS primer. For example, a nucleotide analog having a reversible terminator moiety can be added to a primer such that subsequent extension cannot occur until a deblocking agent is delivered to remove the moiety. Thus, for embodiments that use reversible termination, a deblocking reagent can be delivered to the solid support (before or after detection occurs). Washes can be carried out between the various delivery steps. The cycle can then be repeated n times to extend the primer by n nucleotides, thereby detecting a sequence of length n. Exemplary SBS procedures, fluidic systems and detection platforms that can be readily adapted for use with a composition, apparatus or method of the present disclosure are described, for example, in Bentley et al., Nature 456:53-59 (2008), PCT Publ. Nos. WO 91/06678, WO 04/018497 or WO 07/123744; U.S. Pat. Nos. 7,057,026, 7,329,492, 7,211,414, 7,315,019 or 7,405,281, and US Pat. App. Publ. No. 2008/0108082, each of which is incorporated herein by reference.

Other sequencing procedures that use cyclic reactions can be used, such as pyrosequencing. Pyrosequencing detects the release of inorganic pyrophosphate (PPi) as particular nucleotides are incorporated into a nascent nucleic acid strand (Ronaghi, et al., Analytical Biochemistry 242(1), 84-9 (1996); Ronaghi, Genome Res. 11(1), 3-11 (2001); Ronaghi et al. Science 281(5375), 363 (1998); or U.S. Pat. Nos. 6,210,891, 6,258,568 or 6,274,320, each of which is incorporated herein by reference). In pyrosequencing, released PPi can be detected by being immediately converted to adenosine triphosphate (ATP) by ATP sulfurylase, and the level of ATP generated can be detected via luciferase-produced photons. Thus, the sequencing reaction can be monitored via a luminescence detection system. Excitation radiation sources used for fluorescence based detection systems are not necessary for pyrosequencing procedures. Useful fluidic systems, detectors and procedures that can be used for application of pyrosequencing to apparatus, compositions or methods of the present disclosure are described, for example, in PCT Pat. App. Publ. No. WO2012/058096, US Pat. App. Publ. No. 2005/0191698 A1, or U.S. Pat. No. 7,595,883 or 7,244,559, each of which is incorporated herein by reference.

Sequencing-by-ligation reactions are also useful including, for example, those described in Shendure et al. Science 309:1728-1732 (2005); or U.S. Pat. No. 5,599,675 or 5,750,341, each of which is incorporated herein by reference. Some embodiments can include sequencing-by-hybridization procedures as described, for example, in Bains et al., Journal of Theoretical Biology 135(3), 303-7 (1988); Drmanac et al., Nature Biotechnology 16, 54-58 (1998); Fodor et al., Science 251(4995), 767-773 (1995); or PCT Pat. App. Publ. No. WO 1989/10977, each of which is incorporated herein by reference. In both sequencing-by-ligation and sequencing-by-hybridization procedures, target nucleic acids (or amplicons thereof) that are present at sites of an array are subjected to repeated cycles of oligonucleotide delivery and detection. Compositions, apparatus or methods set forth herein or in references cited herein can be readily adapted for sequencing-by-ligation or sequencing-by-hybridization procedures. Typically, the oligonucleotides are fluorescently labeled and can be detected using fluorescence detectors similar to those described with regard to SBS procedures herein or in references cited herein.

Some sequencing embodiments can utilize methods involving the real-time monitoring of DNA polymerase activity. For example, nucleotide incorporations can be detected through fluorescence resonance energy transfer (FRET) interactions between a fluorophore-bearing polymerase and y-phosphate-labeled nucleotides, or with zero-mode waveguides (ZMWs). Techniques and reagents for FRET-based sequencing are described, for example, in Levene et al. Science 299, 682-686 (2003); Lundquist et al. Opt. Lett. 33, 1026-1028 (2008); Korlach et al. Proc. Natl. Acad. Sci. USA 105, 1176-1181 (2008), each of which is incorporated herein by reference.

Some sequencing embodiments include detection of a proton released upon incorporation of a nucleotide into an extension product. For example, sequencing based on detection of released protons can use an electrical detector and associated techniques that are commercially available from Ion Torrent (Guilford, Conn., a Life Technologies and Thermo Fisher subsidiary) or sequencing methods and systems described in US Pat app. Publ. Nos. 2009/0026082 A1; 2009/0127589 A1; 2010/0137143 A1; or US 2010/0282617 A1, each of which is incorporated herein by reference.

Nucleic acid hybridization techniques are also useful method for determining barcode sequences. In some cases combinatorial hybridization methods can be used such as those used for decoding of multiplex bead arrays (see e.g. U.S. Pat. No. 8,460,865, which is incorporated herein by reference). Such methods utilize labelled nucleic acid decoder probes that are complementary to at least a portion of a barcode sequence. A hybridization reaction can be carried out using decoder probes having known labels such that the location where the labels end up on the solid support identifies the nucleic acid probes according to rules of nucleic acid complementarity. In some cases, pools of many different probes with distinguishable labels are used, thereby allowing a multiplex decoding operation.

The number of different barcodes determined in a decoding operation can exceed the number of labels used for the decoding operation. For example, decoding can be carried out in several stages where each stage constitutes hybridization with a different pool of decoder probes. The same decoder probes can be present in different pools but the label that is present on each decoder probe can differ from pool to pool (i.e. each decoder probe is in a different "state" when in different pools). Various combinations of these states and stages can be used to expand the number of barcodes that can be decoded well beyond the number of distinct labels available for decoding. Such combinatorial methods are set forth in further detail in U.S. Pat. No. 8,460,865 or Gunderson et al., Genome Research 14:870-877 (2004), each of which is incorporated herein by reference.

A method of the present disclosure can include a step of contacting a biological specimen with a solid support that has nucleic acid probes attached thereto. In some embodiments the nucleic acid probes are randomly located on the solid support. The identity and location of the nucleic acid probes may have been decoded prior to contacting the biological specimen with the solid support. Alternatively, the identity and location of the nucleic acid probes can be determined after contacting the solid support with the biological specimen.

In some embodiments the biological specimen is one or more cells. The cell(s) can be individual and free from any tissue or multicellular structure at the time contact is made with the solid support. For example, the cell(s) can be present in a fluid (e.g. when a plurality of different cells are present the fluid can be a fluidic mixture of the different cells) and the fluid can be contacted with the solid support to which the different probes are attached. Any of a variety of cells can be used including, for example, those from a prokaryote, archae or eukaryote. One or more cells used in a method, composition or apparatus of the present disclosure can be a single celled organisms or from a multicellular organism. Exemplary organisms from which one or more cell can be obtained include, but are not limited to a mammal, plant, algae, nematode, insect, fish, reptile, amphibian, fungi or *Plasmodium falciparum*. Exemplary species are set forth previously herein or known in the art.

Embodiments of the present disclosure can also use one or more subcellular components as a biological specimen. For example a fluidic mixture can include one or more nuclei, golgi apparatus, mitochondria, chloroplasts, membrane fractions, vesicles, endoplasmic reticulum, or other components known in the art.

Other useful types of biological specimens are one or more viruses or a viroids. It will be understood that a biological specimen can be a homogeneous culture or population of the above cells, subcellular components, viruses or viroids. Alternatively the biological specimen can be a non-homogenous collection of cells, subcellular components, viruses or viroids, for example, derived from several different organisms in a community or ecosystem. An exemplary community is the collection of bacteria present in the digestive system, lung or other organ of a multicellular organism such as a mammal.

One or more cells, subcellular components, viruses or viroids that are contacted with a solid support in a method set forth herein can be attached to the solid support. Attachment can be achieved using methods known in the art such as those exemplified herein with respect to attachment of nucleic acids to a solid support. In some embodiments, attachment is selective for specific types of cells, subcellular components, viruses or viroids. For example, the solid support can include antibodies or other receptors that are selective for epitopes or ligands present on one or a subset of different cells, subcellular components, viruses or viroids present in a fluidic mixture. In other embodiments, the attachment of cells, subcellular components, viruses or viroids can be mediated by non-selective moieties such as chemical moieties that are broadly reactive.

In particular embodiments, one or more cells, subcellular components, viruses or viroids that have been contacted with a solid support can be lysed to release target nucleic acids. Lysis can be carried out using methods known in the art such as those that employ one or more of chemical treatment, enzymatic treatment, electroporation, heat, hypotonic treatment, sonication or the like. Exemplary lysis techniques are set forth in Sambrook et al., Molecular Cloning: A Laboratory Manual, Third Ed., Cold Spring Harbor Laboratory, New York (2001) and in Ansubel et al., Current Protocols in Molecular Biology, John Wiley and Sons, Baltimore, Md. (1999).

In some embodiments the biological specimen is a tissue section. The tissue can be derived from a multicellular organism such as those exemplified above in regard to cells. A tissue section can be contacted with a solid support, for example, by laying the tissue on the surface of the solid support. The tissue can be freshly excised from an organism or it may have been previously preserved for example by freezing, embedding in a material such as paraffin (e.g. formalin fixed paraffin embedded samples), formalin fixation, infiltration, dehydration or the like.

Optionally, a tissue section can be attached to a solid support, for example, using techniques and compositions exemplified herein with regard to attaching nucleic acids, cells, viruses, beads or the like to a solid support. As a further option, a tissue can be permeabilized and the cells of the tissue lysed when the tissue is in contact with a solid support. Any of a variety of treatments can be used such as those set forth above in regard to lysing cells. Target nucleic acids that are released from a tissue that is permeabilized can be captured by nucleic acid probes on the surface.

A tissue can be prepared in any convenient or desired way for its use in a method, composition or apparatus herein. Fresh, frozen, fixed or unfixed tissues can be used. A tissue can be fixed or embedded using methods described herein or known in the art.

A tissue sample for use herein, can be fixed by deep freezing at temperature suitable to maintain or preserve the integrity of the tissue structure, e.g. less than −20° C. In another example, a tissue can be prepared using formalin-fixation and paraffin embedding (FFPE) methods which are known in the art. Other fixatives and/or embedding materials can be used as desired. A fixed or embedded tissue sample can be sectioned, i.e. thinly sliced, using known methods. For example, a tissue sample can be sectioned using a chilled microtome or cryostat, set at a temperature suitable to maintain both the structural integrity of the tissue sample and the chemical properties of the nucleic acids in the sample.

In some embodiments, a tissue sample will be treated to remove embedding material (e.g. to remove paraffin or formalin) from the sample prior to release, capture or modification of nucleic acids. This can be achieved by contacting the sample with an appropriate solvent (e.g. xylene and ethanol washes). Treatment can occur prior to contacting the tissue sample with a solid support set forth herein or the treatment can occur while the tissue sample is on the solid support. Exemplary methods for manipulating tissues for use with solid supports to which nucleic acids are attached are set forth in US Pat. App. Publ. No. 2014/0066318 A1, which is incorporated herein by reference.

The thickness of a tissue sample or other biological specimen that is contacted with a solid support in a method, composition or apparatus set forth herein can be any suitable thickness desired. In representative embodiments, the thickness will be at least 0.1 µm, 0.25 µm, 0.5 µm, 0.75 µm, 1 µm, 5 µm, 10 µm, 50 µm, 100 µm or thicker. Alternatively or additionally, the thickness of a biological specimen that is contacted with a solid support will be no more than 100 µm, 50 µm, 10 µm, 5 µm, 1 µm, 0.5 µm, 0.25 µm, 0.1 µm or thinner.

A particularly relevant source for a biological specimen is a human being.

The specimen can be derived from an organ, including for example, an organ of the musculoskeletal system such as muscle, bone, tendon or ligament; an organ of the digestive system such as salivary gland, pharynx, esophagus, stomach, small intestine, large intestine, liver, gallbladder or pancreas; an organ of the respiratory system such as larynx, trachea, bronchi, lungs or diaphragm; an organ of the urinary system such as kidney, ureter, bladder or urethra; a reproductive organ such as ovary, fallopian tube, uterus, vagina, placenta, testicle, epididymis, vas deferens, seminal vesicle, prostate, penis or scrotum; an organ of the endocrine system such as pituitary gland, pineal gland, thyroid gland, parathyroid gland, or adrenal gland; an organ of the circulatory system such as heart, artery, vein or capillary; an organ of the lymphatic system such as lymphatic vessel, lymph node, bone marrow, thymus or spleen; an organ of the central nervous system such as brain, brainstem, cerebellum, spinal cord, cranial nerve, or spinal nerve; a sensory organ such as eye, ear, nose, or tongue; or an organ of the integument such as skin, subcutaneous tissue or mammary gland. In some embodiments, a biological specimen is obtained from a bodily fluid or excreta such as blood, lymph, tears, sweat, saliva, semen, vaginal secretion, ear wax, fecal matter or urine.

A specimen from a human can be considered (or suspected) healthy or diseased when used. In some cases, two specimens can be used: a first being considered diseased and a second being considered as healthy (e.g. for use as a healthy control). Any of a variety of conditions can be evaluated, including but not limited to, an autoimmune disease, cancer, cystic fibrosis, aneuploidy, pathogenic infection, psychological condition, hepatitis, diabetes, sexually transmitted disease, heart disease, stroke, cardiovascular disease, multiple sclerosis or muscular dystrophy. Particularly relevant conditions are genetic conditions or conditions associated with pathogens having identifiable genetic signatures.

As set forth above, a flow cell provides a convenient apparatus for use in a method set forth herein. For example, a flow cell is a convenient apparatus for housing a solid support that will be treated with multiple fluidic reagents such as the repeated fluidic deliveries used for some nucleic acid sequencing protocols or some nucleic acid hybridization protocols. In some embodiments, a biological specimen can be delivered to a solid support in a flow cell, for example, when a fluidic mixture of cells, subcellular components, viruses or viroids is delivered to the solid support. In some embodiments it may be preferable to open a flow cell to expose a solid support inside or to remove the solid support from the flow cell in order to allow convenient delivery of a biological specimen to the solid support. For example, opening the flow cell or removing the solid support can allow a user or robotic device to lay a tissue section on the solid support. The opening of a flow cell or removal of a solid support from a flow cell can be temporary. Thus, the flow cell can subsequently be closed or the solid support returned to the flow cell to proceed with one or more subsequent steps of a method set forth herein.

In some embodiments, a flow cell can have a construction that allows it to be opened or taken apart. For example the flow cell can be in a closed state while performing a sequencing reaction, for example to decode barcodes. Then the flow cell can be taken apart so that tissue can be placed on the flow cell surface. The flow cell can be held together by adhesive such that one or more surface can be removed to open it. For example, a flow cell can have a spacer with adhesive surfaces on the top or bottom (akin to single-sided or double-sided sticky tape) and this spacer can occur between two solid supports. One or both of the solid supports can be configured to attach nucleic acids and support a biological specimen as set forth herein. The spacer can have open regions (e.g. created by laser cutting of the spacer material) that create fluidic channels bound by the two solid supports and the spacer. Thus, one or both of the solid supports can be non-permanently adhered to the spacer to allow one or both of them to be removed to allow access to the surface when placing a tissue or other specimen thereon.

A nucleic acid probe used in a composition, apparatus or method set forth herein can include a target capture moiety. In particular embodiments, the target capture moiety is a target capture sequence. The target capture sequence is generally complementary to a target sequence such that target capture occurs by formation of a probe-target hybrid complex. A target capture sequence can be any of a variety of lengths including, for example, lengths exemplified above in the context of barcode sequences.

In multiplex embodiments, a plurality of different nucleic acid probes can include different target capture sequences that hybridize to different target nucleic acid sequences from a biological specimen. Different target capture sequences can be used to selectively bind to one or more desired target nucleic acids from a biological specimen. In some cases, the different nucleic acid probes can include a target capture sequence that is common to all or a subset of the probes on a solid support. For example, the nucleic acid probes on a solid support can have a poly A or poly T sequence. Such probes or amplicons thereof can hybridize to mRNA molecules, cDNA molecules or amplicons thereof that have poly A or poly T tails.

Although the mRNA or cDNA species will have different target sequences, capture will be mediated by the common poly A or poly T sequence regions.

Any of a variety of target nucleic acids can be captured and analyzed in a method set forth herein including, but not limited to, messenger RNA (mRNA), copy DNA (cDNA), genomic DNA (gDNA), ribosomal RNA (rRNA) or transfer RNA (tRNA). Particular target sequences can be selected from databases and appropriate capture sequences designed using techniques and databases known in the art.

Other target capture moieties that are useful include, for example, the moieties set forth herein as useful for attaching nucleic acid probes to a solid support.

A method set forth herein can include a step of hybridizing nucleic acid probes, that are on a solid support, to target nucleic acids that are from portions of the biological specimen that are proximal to the probes. Generally, a target nucleic acid will diffuse from a region of the biological specimen to an area of the solid support that is in proximity with that region of the specimen. Here the target nucleic acid will interact with nucleic acid probes that are proximal to the region of the specimen from which the target nucleic acid was released. A target-probe hybrid complex can form where the target nucleic acid encounters a complementary target capture sequence on a nucleic acid probe. The location of the target-probe hybrid complex will generally correlate with the region of the biological specimen from where the target nucleic acid was derived. In multiplex embodiments, the solid support will include a plurality of nucleic acid probes, the biological specimen will release a plurality of target nucleic acids and a plurality of target-probe hybrids will be formed on the solid support. The sequences of the target nucleic acids and their locations on the support will provide spatial information about the nucleic acid content of the biological specimen. Although the example above is described in the context of target nucleic acids that are released from a biological specimen, it will be understood that the target nucleic acids need not be released. Rather, the target nucleic acids may remain in contact with the biological specimen, for example, when they are attached to an exposed surface of the biological specimen in a way that the target nucleic acids can also bind to appropriate nucleic acid probes on the solid support.

A method of the present disclosure can include a step of extending solid support-attached probes to which target nucleic acids are hybridized. In embodiments where the probes include barcode sequences, the resulting extended probes will include the barcode sequences and sequences from the target nucleic acids (albeit in complementary form). The extended probes are thus spatially tagged versions of the target nucleic acids from the biological specimen.

The sequences of the extended probes identify what nucleic acids are in the biological specimen and where in the biological specimen the target nucleic acids are located. It will be understood that other sequence elements that are present in the nucleic acid probes can also be included in the extended probes. Such elements include, for example, primer binding sites, cleavage sites, other tag sequences (e.g. sample identification tags), capture sequences, recognition sites for nucleic acid binding proteins or nucleic acid enzymes, or the like.

Extension of probes can be carried out using methods exemplified herein or otherwise known in the art for amplification of nucleic acids or sequencing of nucleic acids. In particular embodiments one or more nucleotides can be added to the 3' end of a nucleic acid, for example, via polymerase catalysis (e.g. DNA polymerase, RNA polymerase or reverse transcriptase). Chemical or enzymatic methods can be used to add one or more nucleotide to the 3' or 5' end of a nucleic acid. One or more oligonucleotides can be added to the 3' or 5' end of a nucleic acid, for example, via chemical or enzymatic (e.g. ligase catalysis) methods. A nucleic acid can be extended in a template directed manner, whereby the product of extension is complementary to a template nucleic acid that is hybridized to the nucleic acid that is extended. In some embodiments, a DNA primer is extended by a reverse transcriptase using an RNA template, thereby producing a cDNA. Thus, an extended probe made in a method set forth herein can be a reverse transcribed DNA molecule. Exemplary methods for extending nucleic acids are set forth in US Pat. App. Publ. No. US 2005/0037393 A1 or U.S. Pat. No. 8,288,103 or 8,486,625, each of which is incorporated herein by reference.

All or part of a target nucleic acid that is hybridized to a nucleic acid probe can be copied by extension. For example, an extended probe can include at least, 1, 2, 5, 10, 25, 50, 100, 200, 500, 1000 or more nucleotides that are copied from a target nucleic acid. The length of the extension product can be controlled, for example, using reversibly terminated nucleotides in the extension reaction and running a limited number of extension cycles. The cycles can be run as exemplified for SBS techniques and the use of labeled nucleotides is not necessary.

Accordingly, an extended probe produced in a method set forth herein can include no more than 1000, 500, 200, 100, 50, 25, 10, 5, 2 or 1 nucleotides that are copied from a target nucleic acid. Of course extended probes can be any length within or outside of the ranges set forth above.

Although the methods of the present disclosure are exemplified by an embodiment where probes that are hybridized to target nucleic acids are extended to copy at least a portion of the target nucleic acid, it will be understood that the probes can be modified in alternative ways. The probes that are hybridized to target nucleic acids can be subjected to a reaction that creates a target specific modification of the probe. A target specific modification will result only when the probe interacts with a target nucleic acid, for example, via complementary based hybridization. In many embodiments, the target specific modification will be specific to the sequence of the particular target nucleic acid that interacts with the probe. Examples of useful target specific modifications, include but are not limited to, insertion or addition of a sequence by ligation or transposition (see, for example, US Pat. App. Publ. No. 2010/0120098 A1, incorporated herein by reference), chemical modifications such as psoralen crosslinking or addition of a detectable tag moiety, modifications by nucleic acid enzymes, ligation of a hairpin linker, or other modifications set forth in the nucleic acid assays of US Pat. App. Publ. No. US 2005/0037393 A1 or U.S. Pat. No. 8,288,103 or 8,486,625, each of which is incorporated herein by reference.

It will be understood that probes used in a method, composition or apparatus set forth herein need not be nucleic acids. Other molecules can be used such as proteins, carbohydrates, small molecules, particles or the like. Probes can be a combination of a nucleic acid component (e.g. having a barcode, primer binding site, cleavage site and/or other sequence element set forth herein) and another moiety (e.g. a moiety that captures or modifies a target nucleic acid).

A method set forth herein can further include a step of acquiring an image of a biological specimen that is in contact with a solid support. The solid support can be in any of a variety of states set forth herein. For example, the solid support can include attached nucleic acid probes or clusters derived from attached nucleic acid probes. Alternatively, the solid support may not include nucleic acid probes, instead being in a state that precedes attachment of nucleic acid probes or in a state that follows removal of nucleic acid probes from the solid support. Accordingly, an image can be obtained at any of a variety of points in a method set forth herein.

An image can be obtained using detection devices known in the art.

Examples include microscopes configured for light, bright field, dark field, phase contrast, fluorescence, reflection, interference, or confocal imaging. A biological specimen can be stained prior to imaging to provide contrast between different regions or cells. In some embodiments, more than one stain can be used to image different aspects of the specimen (e.g. different regions of a tissue, different cells, specific subcellular components or the like). In other embodiments, a biological specimen can be imaged without staining.

In particular embodiments, a fluorescence microscope (e.g. a confocal fluorescent microscope) can be used to detect a biological specimen that is fluorescent, for example, by virtue of a fluorescent label. Fluorescent specimens can also be imaged using a nucleic acid sequencing device having optics for fluorescent detection such as a Genome Analyzer®, MiSeq®, NextSeq® or HiSeq® platform device commercialized by Illumina, Inc. (San Diego, Calif.); or a SOLiD™ sequencing platform commercialized by Life Technologies (Carlsbad, Calif.). Other imaging optics that can be used include those that are found in the detection devices described in Bentley et al., Nature 456:53-59 (2008), PCT Publ. Nos. WO 91/06678, WO 04/018497 or WO 07/123744; U.S. Pat. Nos. 7,057,026, 7,329,492, 7,211, 414, 7,315,019 or 7,405,281, and US Pat. App. Publ. No. 2008/0108082, each of which is incorporated herein by reference.

An image of a biological specimen can be obtained at a desired resolution, for example, to distinguish tissues, cells or subcellular components. Accordingly, the resolution can be sufficient to distinguish components of a biological specimen that are separated by at least 0.5 µm, 1 µm, 5 µm, 10 µm, 50 µm, 100 µm, 500 µm, 1 mm or more. Alternatively or additionally, the resolution can be set to distinguish components of a biological specimen that are separated by at least 1 mm, 500 µm, 100 µm, 50 µm, 10 µm, 5 µm, 1 µm, 0.5 µm or less.

A method set forth herein can include a step of correlating locations in an image of a biological specimen with barcode sequences of nucleic acid probes that are attached to a surface to which the biological specimen is, was or will be contacted. Accordingly, characteristics of the biological specimen that are identifiable in the image can be correlated with the nucleic acids that are found to be present in their proximity. Any of a variety of morphological characteristics can be used in such a correlation, including for example, cell shape, cell size, tissue shape, staining patterns, presence of particular proteins (e.g. as detected by immunohistochemical stains) or other characteristics that are routinely evaluated in pathology or research applications. Accordingly, the biological state of a tissue or its components as determined by visual observation can be correlated with molecular biological characteristics as determined by spatially resolved nucleic acid analysis.

A solid support upon which a biological specimen is imaged can include fiducial markers to facilitate determination of the orientation of the specimen or the image thereof in relation to probes that are attached to the solid support. Exemplary fiducials include, but are not limited to beads (with or without fluorescent moieties or moieties such as nucleic acids to which labeled probes can be bound), fluorescent molecules attached at known or determinable features, or structures that combine morphological shapes with fluorescent moieties. Exemplary fiducials are set forth in US Pat. App. Publ. No. 2002/0150909 A1 or U.S. patent application Ser. No. 14/530,299, each of which is incorporated herein by reference. One or more fiducials are preferably visible while obtaining an image of a biological specimen. Preferably, the solid support includes at least 2, 3, 4, 5, 10, 25, 50, 100 or more fiducial markers.

The fiducials can be provided in a pattern, for example, along an outer edge of a solid support or perimeter of a location where a biological specimen resides. In a preferred embodiment, one or more fiducials are detected using the same imaging conditions used to visualize a biological specimen. However if desired separate images can be obtained (e.g. one image of the biological specimen and another image of the fiducials) and the images can be aligned to each other.

Optionally, a biological specimen, can be removed from a solid support after an image has been obtained and after target nucleic acids have been captured by nucleic acid probes on the solid support. Thus, a method of the present disclosure can include a step of washing a solid support to remove cells, tissue or other materials from a biological specimen. Removal of the specimen can be performed using any suitable technique and will be dependent on the tissue sample. In some cases, the solid support can be washed with water. The water can contain various additives, such as surfactants (e.g. detergents), enzymes (e.g. proteases and collagenases), cleavage reagents, or the like, to facilitate removal of the specimen. In some embodiments, the solid support is treated with a solution comprising a proteinase enzyme. Alternatively or additionally, the solution can include cellulase, hemicelluase or chitinase enzymes (e.g. if desiring to remove a tissue sample from a plant or fungal source). In some cases, the temperature of a wash solution will be at least 30° C., 35° C., 50° C., 60° C. or 90° C. Conditions can be selected for removal of a biological specimen while not denaturing hybrid complexes formed between target nucleic acids and solid support-attached nucleic acid probes.

A method of the present disclosure can further include a step of removing one or more extended probes from a solid support. In particular embodiments, the probes will have included a cleavage site such that the product of extending the probes will also include the cleavage site. Alternatively, a cleavage site can be introduced into a probe during a modification step. For example a cleavage site can be introduced into an extended probe during the extension step.

Exemplary cleavage sites include, but are not limited to, moieties that are susceptible to a chemical, enzymatic or physical process that results in bond breakage. For example, the location can be a nucleotide sequence that is recognized by an endonuclease. Suitable endonucleases and their recognition sequences are well known in the art and in many cases are even commercially available (e.g. from New England Biolabs, Beverley Mass.; ThermoFisher, Waltham, Mass. or Sigma Aldrich, St. Louis Mo.). A particularly useful endonuclease will break a bond in a nucleic acid strand at a site that is 3'-remote to its binding site in the nucleic acid, examples of which include Type II or Type IIs restriction endonucleases. In some embodiments an endonuclease will cut only one strand in a duplex nucleic acid (e.g. a nicking enzyme). Examples of endonucleases that cleave only one strand include Nt.BstNBI and Nt.Alwl.

In some embodiments, a cleavage site is an abasic site or a nucleotide that has a base that is susceptible to being removed to create an abasic site. Examples of nucleotides that are susceptible to being removed to form an abasic site include uracil and 8-oxo-guanine. Abasic sites can be created by hydrolysis of nucleotide residues using chemical or enzymatic reagents. Once formed, abasic sites may be cleaved (e.g. by treatment with an endonuclease or other single-stranded cleaving enzyme, exposure to heat or alkali), providing a means for site-specific cleavage of a nucleic acid. An abasic site may be created at a uracil nucleotide on one strand of a nucleic acid. The enzyme uracil DNA glycosylase (UDG) may be used to remove the uracil base, generating an abasic site on the strand. The nucleic acid strand that has the abasic site may then be cleaved at the abasic site by treatment with endonuclease (e.g. EndoIV endonuclease, AP lyase, FPG glycosylase/AP lyase, EndoVIII glycosylase/AP lyase), heat or alkali. In a particular embodiment, the USER™ reagent available from New England Biolabs is used for the creation of a single nucleotide gap at a uracil base in a nucleic acid.

Abasic sites may also be generated at non-natural/modified deoxyribonucleotides other than uracil and cleaved in an analogous manner by treatment with endonuclease, heat or alkali. For example, 8-oxo-guanine can be converted to an abasic site by exposure to FPG glycosylase. Deoxyinosine can be converted to an abasic site by exposure to AlkA glycosylase. The abasic sites thus generated may then be cleaved, typically by treatment with a suitable endonuclease (e.g. EndoIV or AP lyase).

Other examples of cleavage sites and methods that can be used to cleave nucleic acids are set forth, for example, in U.S. Pat. No. 7,960,120, which is incorporated herein by reference.

Modified nucleic acid probes (e.g. extended nucleic acid probes) that are released from a solid support can be pooled to form a fluidic mixture. The mixture can include, for example, at least 10, 100, 1×103, 1×104, 1×105, 1×106, 1×107, 1×108, 1×109 or more different modified probes. Alternatively or additionally, a fluidic mixture can include at most 1×109, 1×108, 1×107, 1×106, 1×105, 1×104, 1×103, 100, 10 or fewer different modified probes. The fluidic mixture can be manipulated to allow detection of the modified nucleic acid probes. For example, the modified nucleic acid probes can be separated spatially on a second solid support (i.e. different from the solid support from which the nucleic acid probes were released after having been contacted with a biological specimen and modified), or the probes can be separated temporally in a fluid stream.

Modified nucleic acid probes (e.g. extended nucleic acid probes) can be separated on a solid support in a capture or detection method commonly employed for microarray-based techniques or nucleic acid sequencing techniques such as those set forth previously herein. For example, modified probes can be attached to a microarray by hybridization to complementary nucleic acids. The modified probes can be attached to beads or to a flow cell surface and optionally amplified as is carried out in many nucleic acid sequencing platforms. Modified probes can be separated in a fluid stream using a microfluidic device, droplet manipulation device, or flow cytometer. Typically, detection is carried out on these separation devices, but detection is not necessary in all embodiments.

A particularly useful droplet manipulation device is a droplet actuator as described for example in U.S. Pat. Nos. 8,637,242, 6,911,132, entitled "Apparatus for Manipulating Droplets by Electrowetting-Based Techniques," issued on Jun. 28, 2005; Pamula et al., U.S. Patent Pub. No. 20060194331, entitled "Apparatuses and Methods for Manipulating Droplets on a Printed Circuit Board," published on Aug. 31, 2006; Pollack et al., International Patent Pub. No. WO/2007/120241, entitled "Droplet-Based Biochemistry," published on Oct. 25, 2007; Shenderov, U.S. Pat. No. 6,773,566, entitled "Electrostatic Actuators for Microfluidics and Methods for Using Same," issued on Aug. 10, 2004; Shenderov, U.S. Pat. No. 25 6,565,727, entitled "Actuators for Microfluidics Without Moving Parts," issued on May 20, 2003; Kim et al., U.S. Patent Pub. No. 20030205632, entitled "Electrowettingdriven Micropumping," published on Nov. 6, 2003; Kim et al., U.S. Patent Pub. No. 20060164490, entitled "Method and Apparatus for Promoting the Complete Transfer of Liquid Drops from a Nozzle," published on Jul. 27, 2006; Kim et al., U.S. Patent Pub. No. 20070023292, entitled "Small Object Moving on Printed Circuit Board," published on Feb. 1, 2007; Shah et al., U.S. Patent Pub. No. 20090283407, entitled "Method for Using Magnetic Particles in Droplet Microfluidics," published on Nov. 19, 2009; Kim et al., U.S. Patent Pub. No. 20100096266, entitled "Method and Apparatus for Real-time Feedback Control of Electrical Manipulation of Droplets on Chip," published on Apr. 22, 2010; Velev, U.S. Pat. No. 7,547,380, entitled "Droplet Transportation Devices and Methods Having a Fluid Surface," issued on Jun. 16, 2009; Sterling et al., U.S. Pat. No. 7,163,612, entitled "Method, Apparatus and Article for Microfluidic Control via Electrowetting, for Chemical, Biochemical and Biological Assays and the Like," issued on Jan. 16, 2007; Becker et al., U.S. Pat. No. 7,641,779, entitled "Method and Apparatus for Programmable Fluidic Processing," issued on Jan. 5, 2010; Becker et al., U.S. Pat. No. 6,977,033, entitled "Method and Apparatus for Programmable Fluidic Processing," issued on Dec. 20, 2005; Deere et al., U.S. Pat. No. 7,328,979, entitled "System for Manipulation of a Body of Fluid," issued on Feb. 12, 2008; Yamakawa et al., U.S. Patent Pub. No. 20060039823, entitled "Chemical Analysis Apparatus," published on Feb. 23, 2006; Wu, U.S. Patent Pub. No. 20110048951, entitled "Digital Microfluidics Based Apparatus for Heat-exchanging Chemical Processes," published on Mar. 3, 2011; Fouillet et al., U.S. Patent Pub. No. 20090192044, entitled "Electrode Addressing Method," published on Jul. 30, 2009; Fouillet et al., U.S. Pat. No. 7,052,244, entitled "Device for Displacement of Small Liquid Volumes Along a Micro-catenary Line by Electrostatic Forces," issued on May 30, 2006; Marchand et al., U.S. Patent Pub. No. 20080124252, entitled "Droplet Microreactor," published on May 29, 2008; Adachi et al., U.S. Patent Pub. No. 20090321262, entitled "Liquid Transfer Device," published on Dec. 31, 2009; Roux et al., U.S. Patent Pub. No. 20050179746, entitled "Device for Controlling the Displacement of a Drop Between Two or Several Solid Substrates," published on Aug. 18, 2005; and Dhindsa et al., "Virtual Electrowetting Channels: Electronic Liquid Transport with Continuous Channel Functionality," Lab Chip, 10:832-836 (2010), each of which is incorporated herein by reference.

Modified probes (e.g. extended nucleic acid probes) can be detected, for example, following separation from a fluidic mixture using methods set forth above or known in the art. In particular embodiments, modified probes that are separated on a second solid support (i.e. a solid support that is different from the first solid support where contact was made between probes and biological specimen) can be detected using microarray-based techniques or nucleic acid sequencing techniques such as those set forth previously herein. Probes that are separated in a fluid stream can be detected using optical, electrical or other detectors that are outfitted in known microfluidic devices, droplet manipulation devices, or flow cytometers. A detection method can be used to determine target nucleic acid sequences, barcode sequences or other sequence regions of extended probes.

Several embodiments have been exemplified with regard to removing modified probes from the solid support where the probes were produced. However, it will be understood that probes on a solid support can be contacted with a biological specimen, modified on the solid support in the presence of target nucleic acids from the specimen and then the modified probes can be detected on the solid support. In such an embodiment, the biological specimen can be removed from the solid support prior to the detection step.

In particular embodiments the present disclosure provides a method for spatially tagging nucleic acids of a biological specimen that includes the steps of (a) providing a plurality of nucleic acid primers attached to a solid support, wherein the nucleic acid primers in the plurality include a universal primer sequence that is common to the nucleic acid primers in the plurality; (b) binding a population of nucleic acid probes to the plurality of nucleic acid primers, wherein the nucleic acid probes include a universal primer binding sequence that hybridizes to the universal primer sequence, a target capture sequence and a barcode sequence that differs from barcode sequences of other nucleic acid probes in the population, thereby attaching the different nucleic acid probes at randomly located positions on the solid support; (c) amplifying the different nucleic acid probes by extension of the nucleic acid primers, thereby producing nucleic acid clusters having copies of the barcode sequence and target capture sequence at the randomly located positions on the solid support; (d) performing a sequencing reaction to determine the barcode sequences at the randomly located positions on the solid support; (e) contacting a biological specimen with the nucleic acid clusters on the solid support; (f) hybridizing the target capture sequences of the clusters to target nucleic acids from portions of the biological specimen that are proximal to the clusters; and (g) extending the target capture sequences to produce extended probes that include sequences from the target nucleic acids and the copies of the barcode sequences, thereby tagging the nucleic acids of the biological specimen.

As exemplified previously herein, a plurality of nucleic acid primers can be attached to a solid support, wherein the nucleic acid primers in the plurality include a universal primer sequence that is common to the nucleic acid primers in the plurality. In this embodiment, a second plurality of nucleic acid primers can be attached to the solid support, and the nucleic acid primers in the second plurality can have a second universal primer sequence that is common to the nucleic acid primers in the second plurality. In this embodiment, a plurality of different nucleic acid probes that is contacted with the support can include a universal primer binding sequence that hybridizes to the universal primer on the solid support, as set forth above, and the different nucleic acid probes can also include a second universal primer binding sequence that hybridizes to the second universal primer sequence. This configuration of universal primers and universal primer binding sites can be particularly useful for amplifying the different nucleic acid probes via bridge amplification, wherein the nucleic acid primers in the first and second plurality are extended.

Typically, when a nucleic acid probe contains first and second universal primer binding sites, they will be located at the ends of the probe. In some embodiments it may be desirable to remove at least one of the primer binding sites from the nucleic acid probe or from amplicons produced from the probe. Accordingly, the nucleic acid probes can optionally include a cleavage site between the target capture sequence and one of the universal primer binding sequence. In this case, a cleavage reaction can be performed to separate the universal primer binding site from the target capture sequence. Generally, the portion of the probe (or its amplicons) that contains the target capture sequence will be attached to the solid support resulting in removal of the primer binding site from the solid support and retention of the target capture sequence. Thus, the cleaved probe can be used for hybridizing target nucleic acids and the cleaved probe can be extended using method set forth previously herein.

In some embodiments, a nucleic acid probe will include two different cleavage sites. A first cleavage site will be located between a first primer binding site and one or more other sequence elements of the probe. A second cleavage site can be located between a second primer binding site and the one or more other sequence elements of the probe. The cleavage sites can be reactive to different cleavage reactions such that each one can be selectively cleaved without necessarily cleaving the other. Accordingly, the first cleavage site can be cleaved prior to modifying the probe (for example, prior to producing an extended probe), thereby separating the first primer binding site from the one or more other sequence elements that remain attached to a solid support. The second cleavage site can be cleaved after modifying the probe (for example, after producing the extended probe), thereby releasing the modified probe for subsequent detection.

Alternatively, a nucleic acid probe can include the first cleavage site and a primer that is used to capture or amplify the nucleic acid probe can include the second cleavage site. In this configuration, the first cleavage site can be located between a first primer binding site and one or more other sequence elements of the probe such that cleavage separates the first primer binding site from one or more other sequence elements of the probe that remain attached to a solid support. Again, this first cleavage step will typically be carried out prior to modifying the probe (for example, prior to producing an extended probe). A second cleavage step can be carried out to cleave the second cleavage site after modifying the probe (for example, after producing the extended probe), thereby releasing the modified probe for subsequent detection.

The two embodiments above exemplify a cleavage site located between a point of attachment of a nucleic acid probe (or modified nucleic acid probe) and one or more sequences of the probe (or modified probe) that contain information such as a spatial barcode or target sequence. Thus, this cleavage site is useful for release of modified probes (e.g. extended probes) to detect the sequence information and determine what sequences are present in a biological specimen and where the sequences are present in the specimen.

In some embodiments, one or more probes that are contacted with a solid support in a method set forth herein can include a sequencing primer binding site.

Accordingly, a modified probe (e.g. extended probe) can be detected in a sequencing technique that includes a step of hybridizing a sequencing primer to the sequencing primer binding site. The sequencing primer binding site can be located in the probe such that cleavage of a modified version of the probe (e.g. an extended probe) will yield a released probe that includes the sequencing primer binding site.

The sequencing primer binding site can be a universal sequencing primer binding site such that a plurality of different probes (e.g. having different barcode and/or target sequences) will have the same sequencing primer binding site.

This disclosure further provides a method for spatially tagging nucleic acids of a biological specimen, the method including steps of (a) providing an array of beads on a solid support, wherein different nucleic acid probes are attached to different beads in the array, wherein the different nucleic acid probes each include a barcode sequence, wherein each bead includes a different barcode sequence from other beads on the solid support, and wherein each of the different nucleic acid probes includes a target capture sequence; (b) performing a decoder probe hybridization reaction on the solid support to determine the barcode sequences at the randomly located probes on the solid support; (c) contacting a biological specimen with the array of beads; (d) hybridizing the different nucleic acid probes to target nucleic acids from portions of the biological specimen that are proximal to the beads; and (e) extending the different nucleic acid probes to produce extended probes that include sequences from the target nucleic acids and the barcode sequences, thereby tagging the nucleic acids of the biological specimen.

It will be understood that manipulations of solid supports or of nucleic acids attached to solid supports can be carried out using beads as solid supports. The beads can be attached to a surface (e.g. an array of wells as in a BeadArray™ from Illumina) before or after such manipulations are carried out. For example, nucleic acid probes can be captured on beads before or after the beads are distributed on an array, nucleic acid probes can be amplified to create amplicons on beads before or after the beads are distributed on an array etc.

Example I

Spatially Tagging mRNA from a Tissue Sample Using Illumina Flow Cells

Figure 1B:
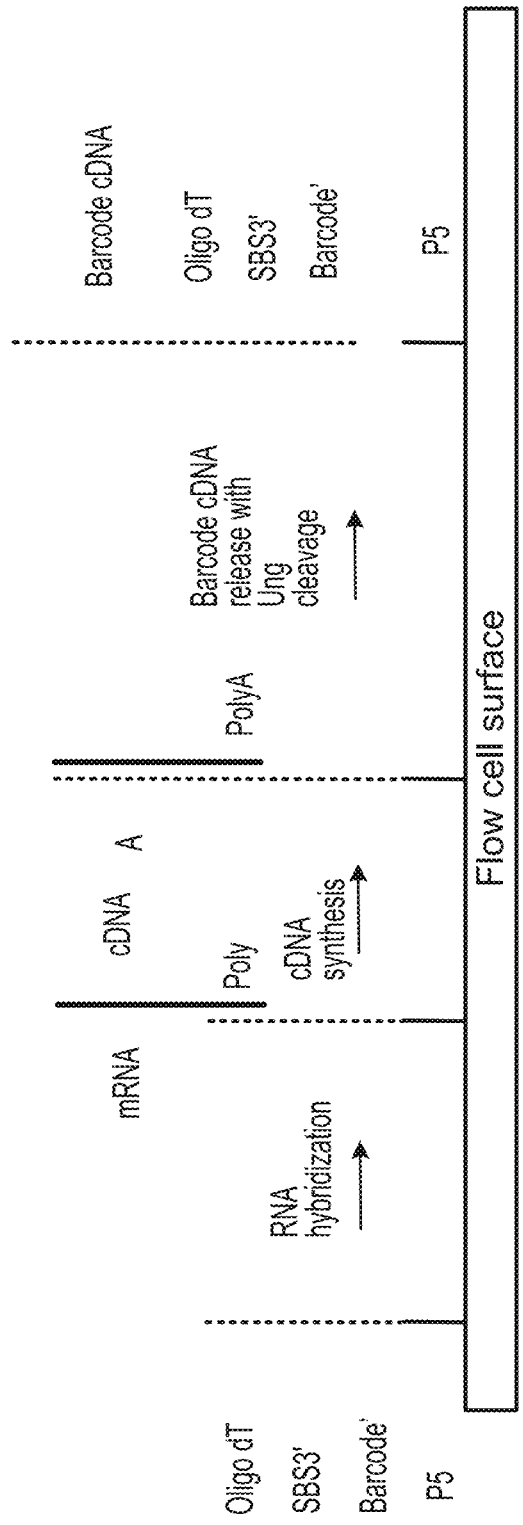
FIG. 1B shows a diagrammatic representation showing capture of mRNA with barcoded oligo dT probes, generating cDNA, and releasing the extended probes.

A method for generating barcoded oligo-dT containing clusters, then revealing the barcoded oligo-dT with a restriction enzyme digest followed by sequencing is described in FIG. 1. A library of fragments containing a single stranded, barcoded oligo-dA, P5',P7, SBS3 sequencing primer binding site and a BspHI restriction enzyme site (shown in the top panel of FIG. 1) were prepared by oligo synthesis (Integrated DNA Technologies). The barcodes were 27mers and were randomly generated during synthesis. The binding site for the SBS3 sequencing primer was included for decoding of the barcode by sequencing. An oligo-dA stretch was included to generate an oligo dT site upon clustering and linearization. Bridge amplification and clustering were performed according to standard cluster chemistry (Illumina TruSeq PE Cluster Kit v3 cBot P/N: 15037931) on an Illumina GA flow cell using manufacture's recommended protocol.

Following bridge amplification and clustering the clusters were linearized by cleavage of 8-oxo-G in P7 primer using Formamidopyrimidine DNA glycosylase (Fpg) enzyme provided in the TruSeq PE Cluster kit. This was followed by restriction enzyme digest with 200 Units/ml BspH1 (NEB Cat #R0517L at 37° C. for 1 5min to remove P7' from the PS adapter anchored strand of the cluster to unveil the oligo-dT stretch for subsequent extension in the presence of an mRNA. Enzyme concentrations in the range of 100-400 U/ml have been tested for 15 or 30 min. The de-coding of the barcode was initiated by the SBS3 sequencing primer.

As shown in the bottom panel of FIG. 1, oligo-dT sequences in the cluster were used to capture poly A+ RNA after decoding of the barcode. Barcoded cDNA was produced by extension of the oligo-dT strand of the cluster using TruSeq RNA Sample Prep Kit (Illumina P/N: 15012997) and MMLV Reverse Transcriptase 1st-Strand cDNA Synthesis Kit (Epicentre P/N: MM070150) according to the manufacturer's recommended conditions. The captured RNA was used as a template. Barcoded cDNA was released from the PS sequence of the flow cell using Illumina's Uracil Specific Excision reagents (USER) (Illumina's TruSeq PE cluster kit) liberating a barcoded cDNA library that was used for sequencing on a second Illumina flow cell.

Figure 2A:
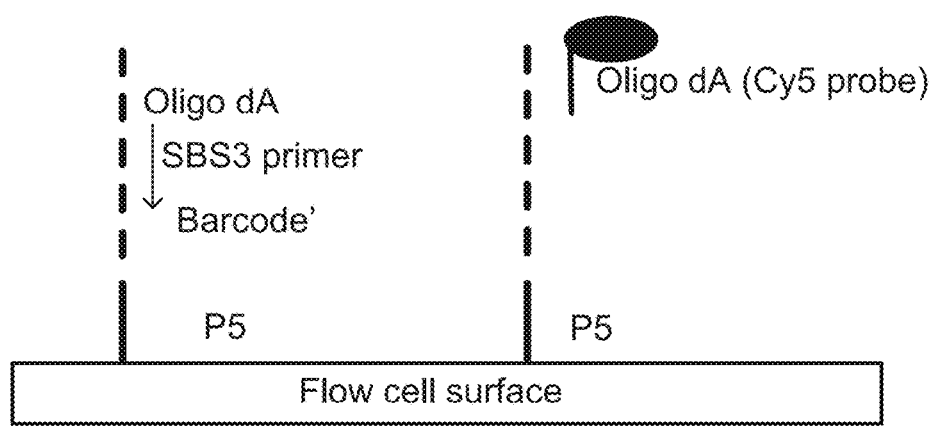
FIG. 2A shows data indicating the availability of oligo dT capture sequences on probes after bridge amplification of the probes and restriction enzyme digest with BspH1 to remove one of the primer binding sites used for bridge amplification.
Figure 2B:
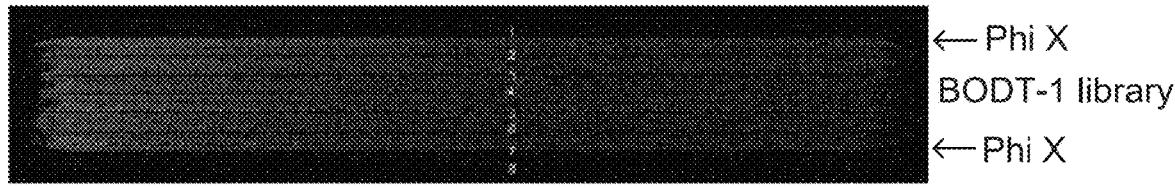
FIG. 2B shows a flow cell with Cy5 labeled poly A oligonucleotides hybridized to the oligonucleotide dT probes.
Figure 2C:
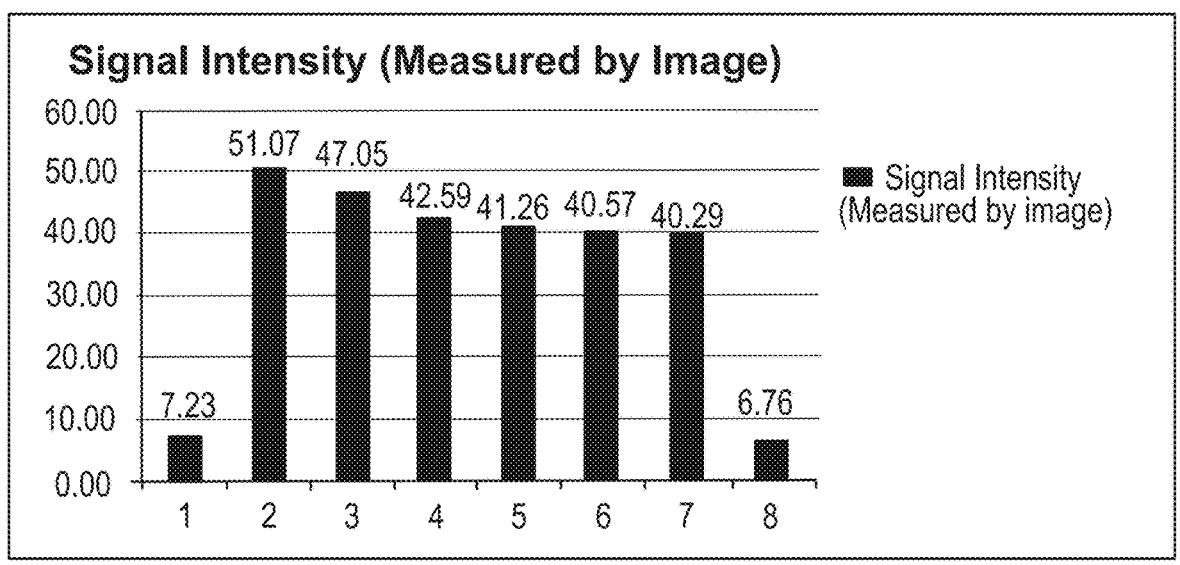
FIG. 2C is a graph showing the signal intensity from each lane in the flow cell.

The availability of oligo dT capture sequence after the restriction enzyme digest with BspH1 was confirmed by hybridizing the linearized clusters with a Cy5 labeled poly A (24mer) as diagrammed in panel A of FIG. 2. Briefly, after the restriction enzyme digestion, the clusters were treated with 0.1N NaOH and washed with HT2 low salt buffer to remove the second strand on the flow cell. Then, 500 nM of Cy5 oligo-dA (24mer) was flowed over the linearized and denatured clusters at 30 µl/min rate and incubated at 40° C. for 5 min and then imaged. Hybridization of Cy5 labeled poly A to the oligo dT was detected in lanes 2-7 of the GA flow cell where the oligo dT containing BODT-1 libraries were present (see the image of the flow cell shown in FIG. 2, Panel B). As evident from the flow cell image (Panel B), and the bargraph (Panel C), the control PhiX libraries (lanes 1 and 8 of the flow cell) were shown to have very low fluorescence in the Cy5 signal. These results demonstrated that an oligo-dT site can be created in the cluster that upon linearization can bind specifically to Cy5 poly A (24mer).

Figure 4:
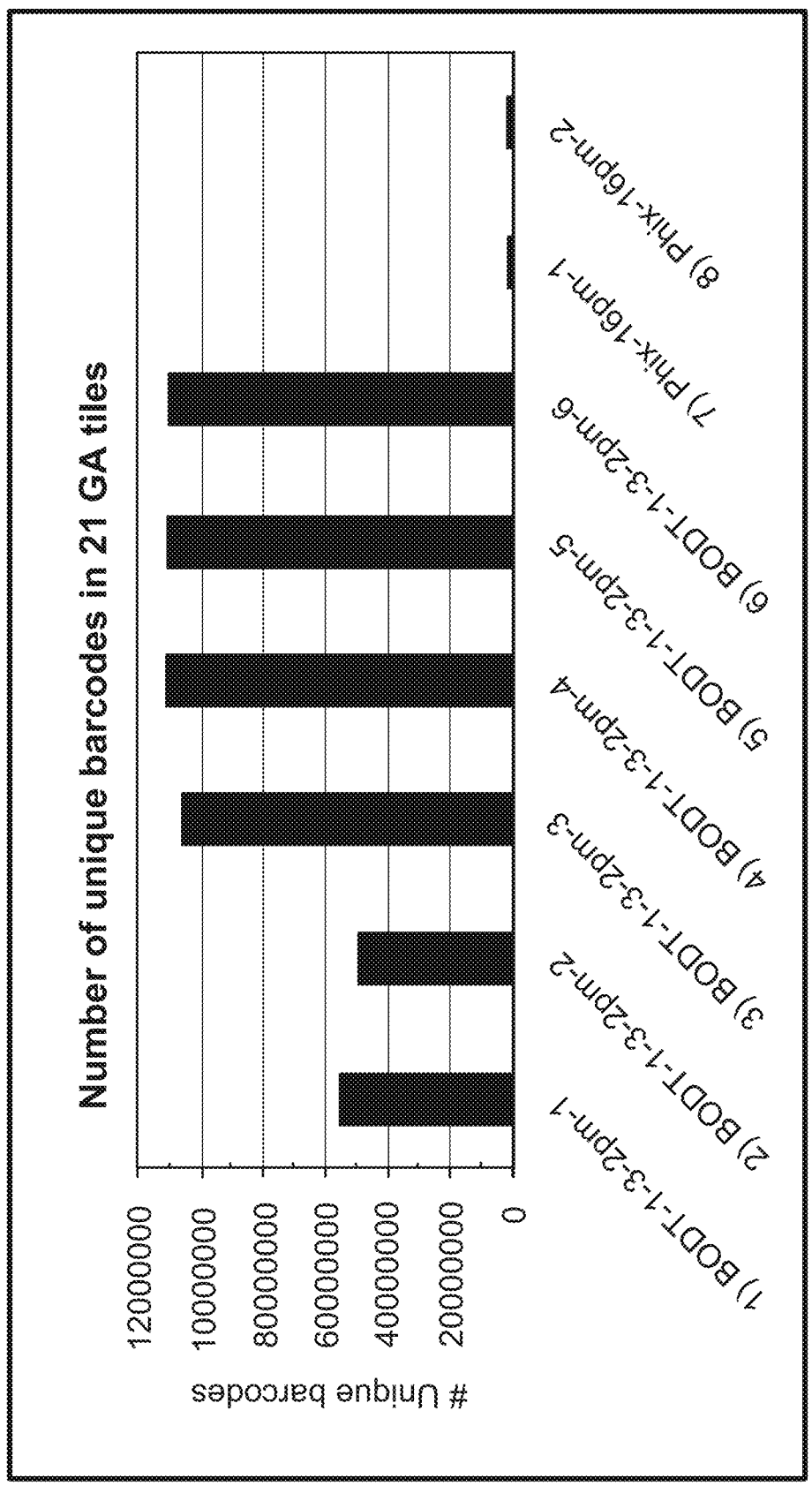
FIG. 4 the number of unique barcodes determined in 21 tiles of the flow cell described in Example 1 and shown in FIG. 2.

The sequencing metrics of the flow cell described above with 3.2 µM of BODT-1 library is given in the table shown in FIG. 3. Millions of reads were detected in 21 tiles from GA sequencing. Following sequencing, the number of unique barcodes were determined as plotted in FIG. 4. This was done by assuming that every passing filter (PF) read was a barcode and determining the number of unique reads (barcodes) in each lane. Between 5 and 11 million unique barcoded clusters were detected after sequencing tiles compared to the PhiX control libraries. These results demonstrated that sequence decoding of a library of barcoded oligo-dT sequences is feasible and generates millions of unique barcodes.

Example II

Cell Adhesion on Illumina Flow Cells Single cells were captured on a patterned flow cell (HiSeq X10 flow cell, Illumina). All reagent flow steps were performed using a peristaltic pump or the cBOT cluster generation instrument (Illumina). Briefly, nuclease free water was flowed on all lanes of the patterned flow cell followed by 30-70K Poly D Lysine Solution (100 µg/ml and 20 µg/ml) at a flow rate of 100 µl/min for 8 min. Heat inactivated Fetal Bovine Serum (Life Technologies #10082-139) was also tested as an adhesive. The adhesives were incubated on the flow cell lanes for 1 hr, followed by a 1×PBS+0.5% Pluronic F-68 (Life Technologies #24040-032) wash. Next, the cells were adhered to the coated flow cells by flowing 5 to 50 cells/µl or approximately 100-1000 cells per lane at a rate of 100 µl/min, followed by an incubation step for 60 min to bind the cells. The flow cell was washed with 1×PBS/0.5% pluronic at a rate of 75 µl/min. If cells were fixed on the flow cell, 1% Paraformaldehyde (PFA) was flowed on the flow cell after flowing the cells as described above and incubated for 1 5min followed by the 1×PBS/0.5% pluronic was step. The flow cell was removed and the number of cells per lane counted using a microscope.

Figure 5A:
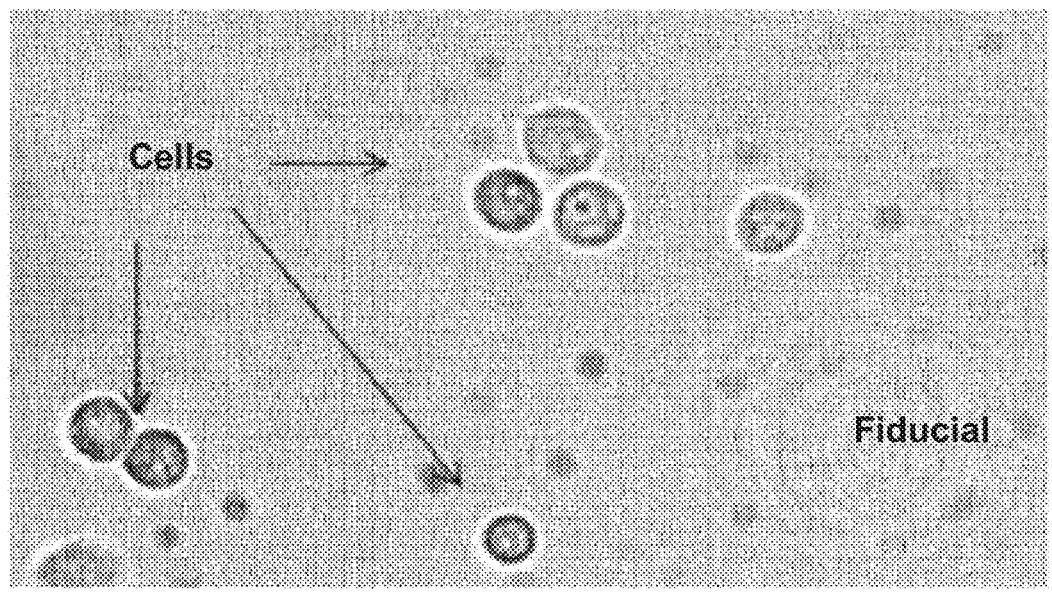
FIG. 5A shows an image of cells captured on a patterned flow cell (Panel A).
Figure 5B:
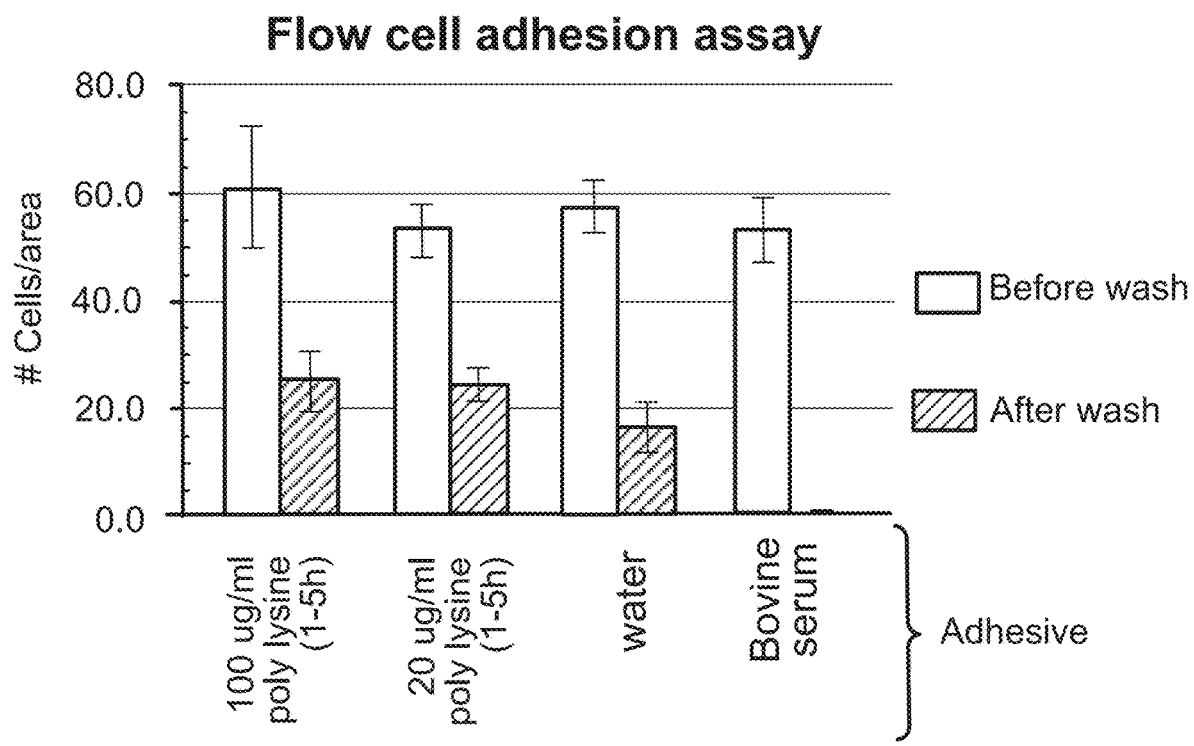
FIG. 5B is a graph showing a flow cell adhesion assay.
Figure 6:
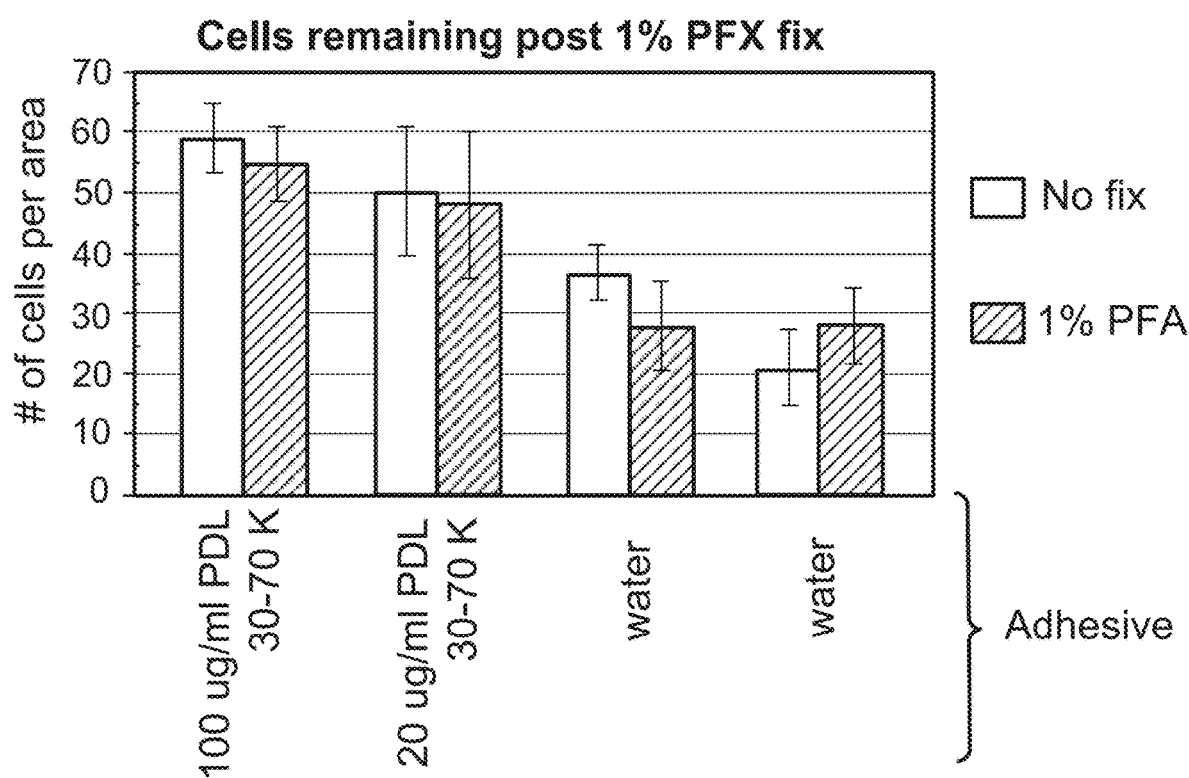
FIG. 6 shows cells that remain adhered to a flow cell in different conditions.

FIG. 5, Panel A shows an image of cells captured on the patterned flow cell. The cell count data shown in FIG. 5, Panel B confirmed that the poly D Lysine coated flow cells aided cell adherence compared to the BSA coated or no adhesive treated control. As shown in FIG. 6, the adhered cells can be successfully fixed with 1% PFA.

Example III

Spatially Localized Capture of Target mRNA by Probes Attached to a Gel Surface This example describes creation of a lawn of poly T probes on a gel coated slide, placement of tissue slices on top of a lawn of poly T probes, release of RNA from the tissue sections, capture of the released mRNA by the poly T probes, reverse transcription to Cy 3 label the poly T probes, removal of the tissue and imaging of the slide.

Figure 7A:
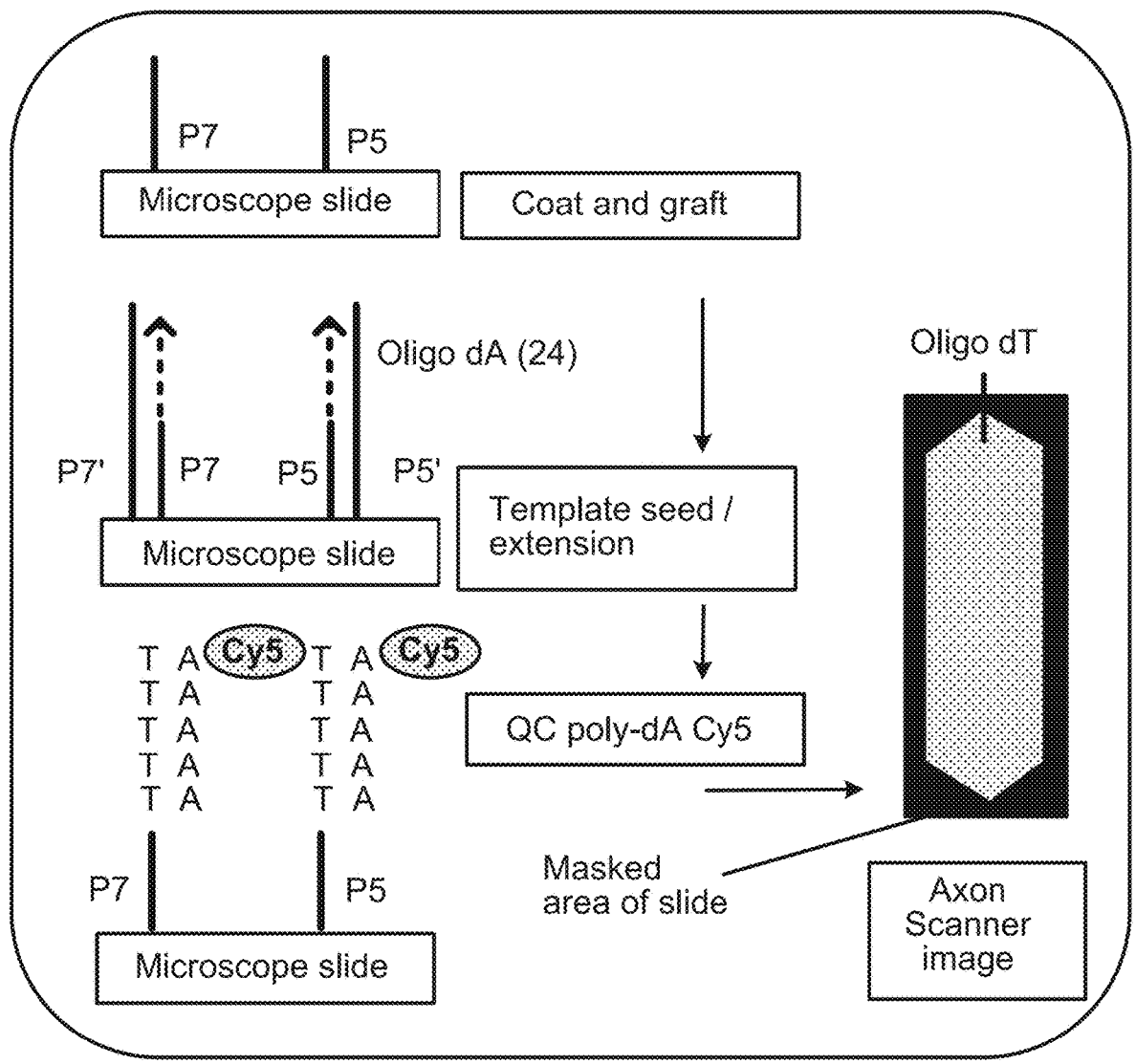
FIG. 7A shows a diagrammatic representation of steps and reagents used to create probes attached to a gel (Panel A)
Figure 7B:
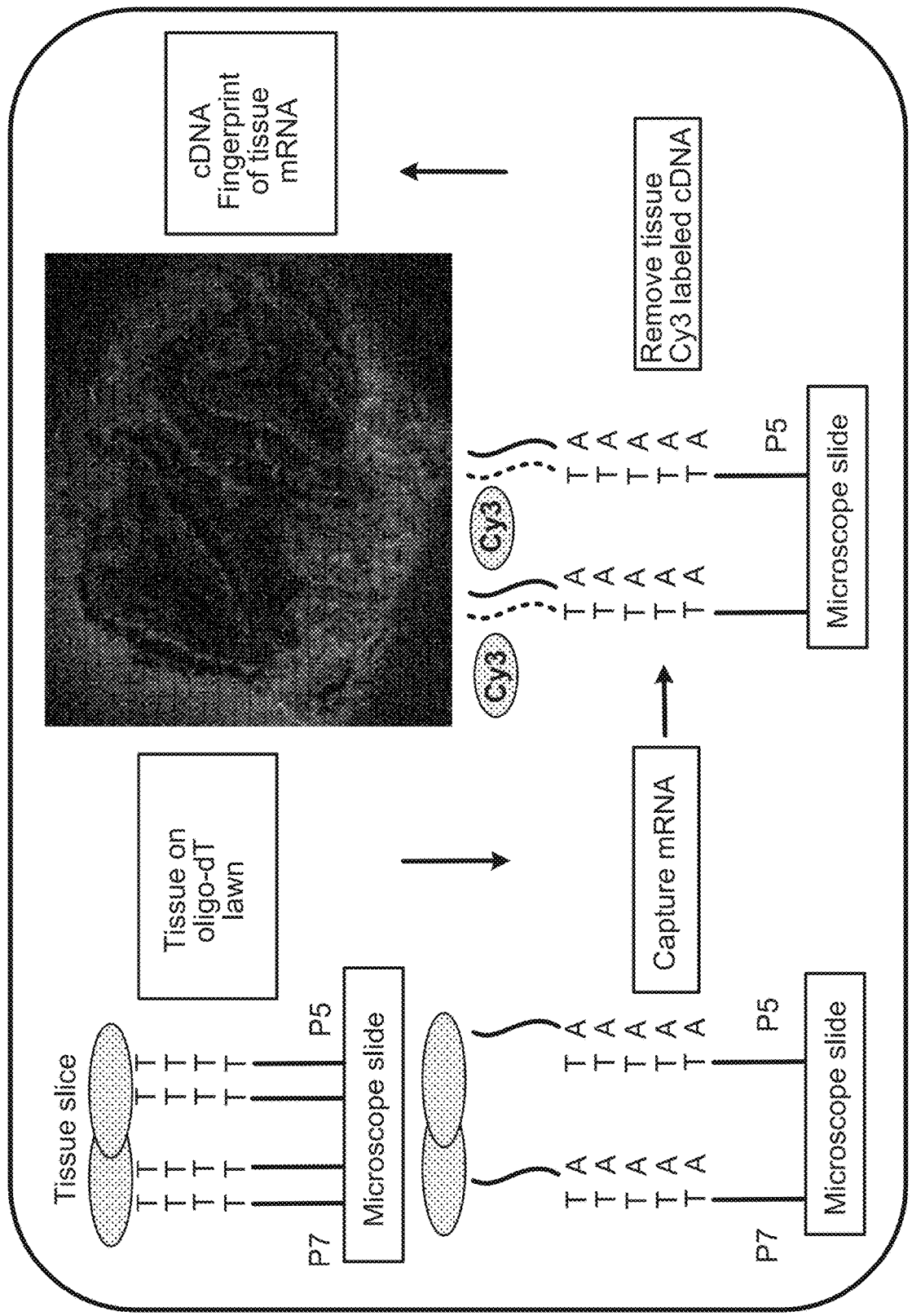
FIG. 7B shows a diagrammatic representation of steps and reagents used to capture target nucleic acids using the gel-attached probes and fluorescently label the probes (Panel B) and an image created by the fluorescently labeled target nucleic acids following capture by the probes and removal of the tissue from the gel.

FIG. 7, Panel A shows a diagrammatic representation of steps and reagents used to create probes attached to a gel. Briefly, a microscope slide was coated with silane free acrylamide (SFA), PS and P7 primers were attached (see US Pat. App. Pub. No. 2011/0059865 A1, which is incorporated herein by reference), probes having a poly A sequence and either a PS or P7 complementary sequence were hybridized to the PS and P7 primers, respectively, and the PS and P7 primers were extended to produce poly T sequence extensions. A quality control step was performed by hybridizing Cy5 labeled polyA oligonucleotides to the extended primers and imaging the surface using an Axon Imager.

As shown in Panel B of FIG. 7, a tissue section was placed on the gel having the polyT extended primers. The tissue was treated to release mRNA and poly A tails of the released mRNA were hybridized to poly T sequences of the extended primers. The poly T sequences were extended using the captured mRNAs as templates and the extended primers were selectively labeled with Cy3. The tissue was removed from the gel and the surface was imaged to detect Cy3 fluorescence.

As shown in the image of FIG. 7, areas of the gel that were proximal to areas of the tissue that released mRNA species appeared fluorescent while areas that did not release mRNA appeared dark in the image. Thus, the captured mRNA created a fingerprint-like image of the tissue.

Example IV

Spatially Localized Capture of Target mRNA by Probes Attached to a BeadArray™ Surface This example describes placement of tissue slices on top of a BeadArray™ having poly T probes, release of RNA from the tissue sections, capture of the released mRNA by the poly T probes, reverse transcription to Cy5 label the poly T probes, removal of the tissue and imaging of the BeadArray™.

Figure 8A:
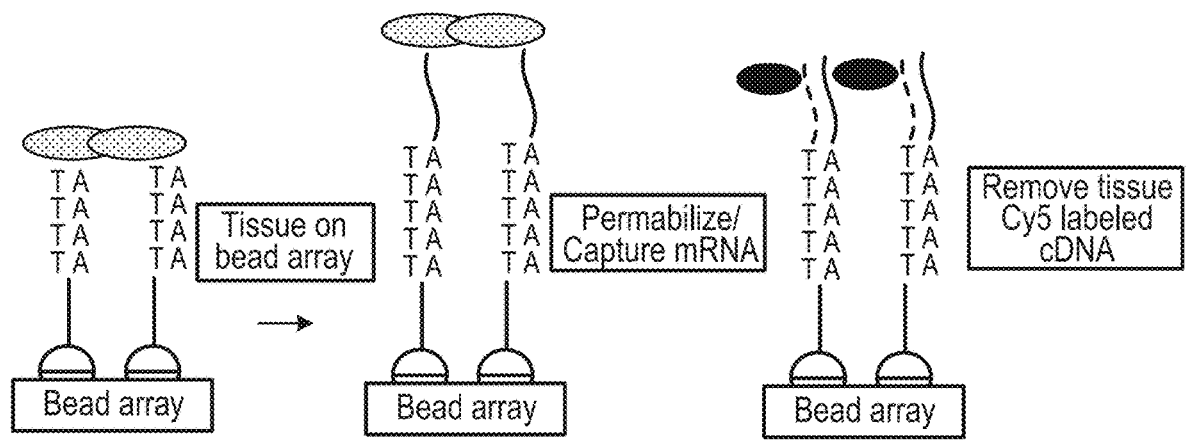
FIG. 8A shows a diagrammatic representation of steps and reagents used to capture target nucleic acids using BeadArray™-attached probes and fluorescently label the probes (Panel A).
Figure 8B:
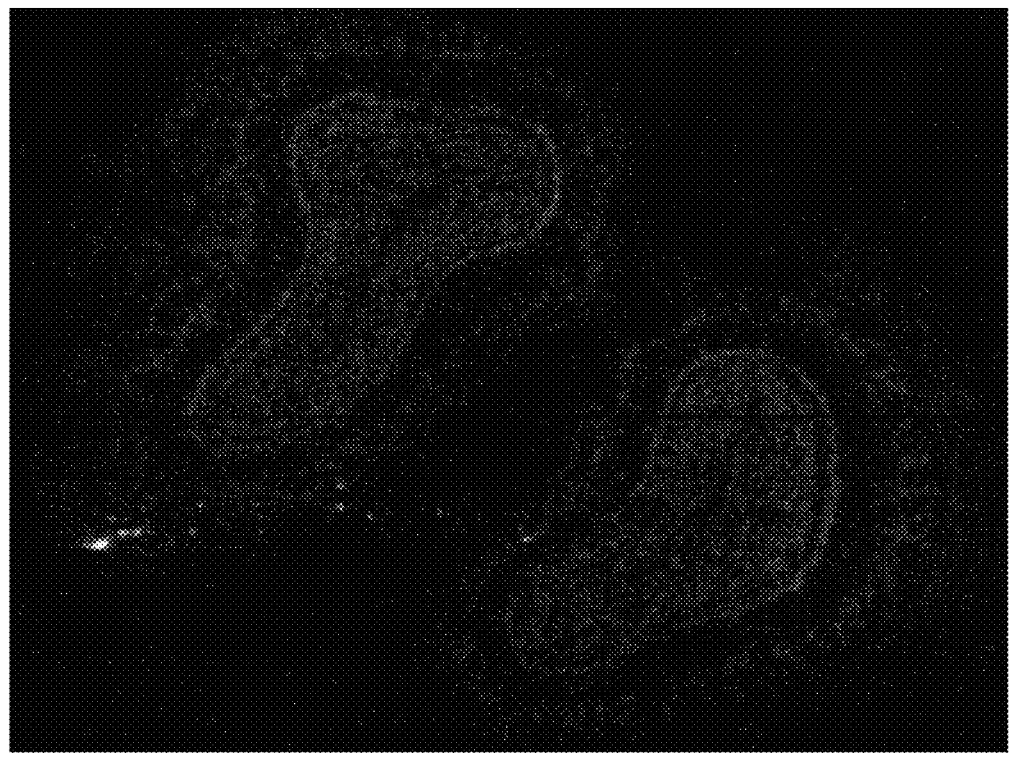
FIG. 8B shows an image created by the fluorescently labeled target nucleic acids following capture by the probes and removal of the tissue from the BeadArray™.capture of released mRNA from the tissue (Panel B).

As shown in Panel A of FIG. 8, a mouse olfactory tissue section was placed on a BeadArray™ having polyT probes. The tissue was treated to release mRNA and poly A tails of the released mRNA were hybridized to poly T sequences of the probes. The poly T sequences were extended using the captured mRNAs as templates and the extended primers were selectively labeled with Cy5. The tissue was removed from the BeadArray™ and the BeadArray™ was imaged to detect Cy5 fluorescence.

As shown in Panel B of FIG. 7, areas of the BeadArray™ that were proximal to areas of the tissue that released mRNA species appeared fluorescent while areas that did not release mRNA appeared dark in the image. Thus, the captured mRNA created a fingerprint-like image of the tissue.

Throughout this application various publications, patents or patent applications have been referenced. The disclosure of these publications in their entireties are hereby incorporated by reference in this application.

The term "comprising" is intended herein to be open-ended, including not only the recited elements, but further encompassing any additional elements.

A number of embodiments have been described. Nevertheless, it will be understood that various modifications may be made. Accordingly, other embodiments are within the scope of the following claims.

The invention claimed is:

1. A method for spatially tagging target nucleic acids of a biological specimen, comprising:
    (a) providing a solid support comprising a population of nucleic acid probes attached at randomly located positions on the solid support, wherein a nucleic acid probe in the population of nucleic acid probes comprises: (i) a target capture sequence and (ii) a spatial tag sequence that differs from spatial tag sequences of nucleic acid probes in the population at other randomly located positions on the solid support;
    (b) performing a nucleic acid detection reaction to determine the spatial tag sequences at the randomly located positions on the solid support;
    (c) contacting the biological specimen with a portion of the population of nucleic acid probes on the solid support;
    (d) hybridizing one or more of the target capture sequences of the population of nucleic acid probes to target nucleic acids from the biological specimen that are proximal to the population of nucleic acid probes; and
    (e) extending the one or more target capture sequences to produce extended probes that comprise complementary sequences to the target nucleic acids, or portions thereof, and the spatial tag sequences, thereby spatially tagging the target nucleic acids of the biological specimen.

2. The method of claim 1, wherein step (a) further comprises amplifying the population of nucleic acid probes on the solid support, thereby producing nucleic acid clusters having copies of the spatial tag sequence and the target capture sequence at the randomly located positions on the solid support.

3. The method of claim 2, wherein the nucleic acid clusters on the solid support have an average pitch of less than 10 microns and/or an average area of less than 100 microns.

4. The method of claim 1, wherein the nucleic acid detection reaction is a sequencing reaction or a decoder probe hybridization reaction.

5. The method of claim 1, wherein the solid support comprises an array of beads, where the population of nucleic acid probes are attached to beads in the array, wherein:
    (i) step (a) comprises randomly distributing the beads on the solid support such that each bead in the array of beads occupies a randomly located position on the solid support; or
    (ii) the solid support comprises wells having dimensions that accommodate no more than a single bead, wherein: the beads are attached to different spatial tag sequences and there a greater number of spatial tag sequences than number of wells, the solid support comprises at least $1 \times 10^6$ beads, the array of beads has an average pitch of less than 10 microns, and/or the beads have an average diameter of less than 10 microns.

6. The method of claim 1, wherein the solid support comprises a pattern of discrete features.

7. The method of claim 2, wherein the solid support comprises a gel coating, wherein a plurality of nucleic acid primers is attached to the gel coating, wherein a nucleic acid primer of the plurality of nucleic acid primers comprises a universal primer sequence that is common to the nucleic acid primers, and wherein a nucleic acid probe of the population of nucleic acid probes comprises a universal primer binding sequence that hybridizes to the universal primer sequence.

8. The method of claim 7, wherein a second plurality of nucleic acid primers is further attached to the gel coating, wherein a nucleic acid primer of the second plurality of nucleic acid primers comprise a second universal primer sequence that is common to the nucleic acid primers of the second plurality of nucleic acid primers, and wherein the nucleic acid probe comprises a second universal primer binding sequence that hybridizes to the second universal primer sequence, and the amplifying comprises bridge amplification.

9. The method of claim 1, wherein different nucleic acid probes of the population of nucleic acid probes hybridize to different target nucleic acids from the biological specimen.

10. The method of claim 1, wherein different nucleic acid probes of the population of nucleic acid probes comprise a common target capture sequence, and the common target capture sequence comprises a poly(T) or a poly(A) sequence.

11. The method of claim 1, wherein the method further comprises:
acquiring an image of the biological specimen in contact with the solid support; and correlating the determined spatial tag sequences at the randomly located positions on the solid support with location in the image of the biological specimen.

12. The method of claim 1, wherein the method further comprises:
removing the extended probes from the solid support; and determining the sequences of the target nucleic acids, or portions thereof, and the spatial tag sequences for the extended probes that have been removed from the solid support.

13. The method of claim 12, wherein determining the sequences of the target nucleic acids, or portions thereof, and the spatial tag sequences for the extended probes that have been removed from the solid support comprises sequencing-by-synthesis, sequencing-by-hybridization, or sequencing-by-ligation.

14. The method of claim 1, wherein the method further comprises:
removing the extended probes from the solid support; and attaching the extended probes that have been removed from the solid support to a second solid support.

15. The method of claim 14, wherein the second solid support comprises a flowcell.

16. The method of claim 1, further comprising amplifying the extended probes and the spatial tag sequence or a complement thereof, thereby generating amplification products comprising target nucleic acids or complements thereof or a portion of the target nucleic acids or complements thereof, and the spatial tag or a complement thereof.

17. The method of claim 16, wherein the amplifying is selected from the group consisting of: polymerase chain reaction, rolling circle amplification, multiple strand displacement amplification, and random prime amplification.

18. The method of claim 16, wherein the method further comprises performing a sequencing reaction on the amplification products to determine all or a portion of the target nucleic acid sequences or complements thereof, and the spatial tag sequences or complements thereof, thereby determining a spatial location of target nucleic acids in the biological specimen, wherein the sequencing reaction comprises sequencing-by-synthesis, sequencing-by-hybridization, or sequencing-by-ligation.

19. The method of claim 18, wherein determining the spatial location of target nucleic acids in the biological specimen further comprises correlating the determined sequences of the target nucleic acids or complements thereof and the spatial tag sequences or complements thereof with an acquired image of the biological specimen, wherein the acquired image was previously correlated with the randomly located spatial tag sequences on the solid support.

20. The method of claim 16, wherein the method further comprises removing the amplification products from the solid support and, pooling the amplification products to form a mixture of amplification products that have been removed from the solid support, and attaching the amplification products that have been removed from the solid support to a second solid support.

21. The method of claim 1, wherein the solid support was located in or on a flowcell during step (b), and the solid support is removed from the flow cell during step (c) or the flowcell is opened to expose the solid support during step (c).

22. The method of claim 2, wherein the method further comprises, after step (a), digesting the nucleic acid clusters with a restriction enzyme, thereby revealing the target capture sequences.

23. The method of claim 1, wherein the method further comprises a step of staining the biological specimen.

24. The method of claim 6, wherein a feature of the pattern of discrete features is selected from the group consisting of: pits, wells, channels, ridges, raised regions, pegs, posts, and beads.

25. The method of claim 24, wherein the features of the pattern of discrete features on the solid support have an average pitch of less than 1 µm.

26. The method of claim 1, wherein the biological specimen is a mixture of cells, and step (c) further comprises attaching the cells to the solid support and/or lysing the cells to release the target nucleic acids from the cells.

27. The method of claim 1, wherein the biological specimen is a tissue section, and step (c) further comprises attaching the tissue section to the solid support and/or permeabilizing the tissue section to release the target nucleic acids from the tissue.

28. The method of claim 1, wherein the solid support includes fiducial markers.

29. The method of claim 1, wherein the target nucleic acids are selected from the group consisting of mRNA, gDNA, and rRNA.

30. The method of claim 29, wherein the target nucleic acids are mRNA.

* * * * *

UNITED STATES PATENT AND TRADEMARK OFFICE
CERTIFICATE OF CORRECTION

PATENT NO. : 11,739,372 B2  
APPLICATION NO. : 18/166853  
DATED : August 29, 2023  
INVENTOR(S) : Jonas Frisen et al.

Page 1 of 1

It is certified that error appears in the above-identified patent and that said Letters Patent is hereby corrected as shown below:

On the Title Page

Column 1 (Related U.S. Application Data), Line 12, Delete "Apr. 10, 2015," and insert -- Apr. 4, 2016, --.

In the Claims

Column 34, Line 38, in Claim 3, delete "microns." and insert -- $microns^2$. --.

Signed and Sealed this  
Fifth Day of November, 2024

*Katherine Kelly Vidal*

Katherine Kelly Vidal  
*Director of the United States Patent and Trademark Office*